United States Patent
Sarthy et al.

(10) Patent No.: US 11,744,843 B2
(45) Date of Patent: Sep. 5, 2023

(54) IDENTIFICATION AND TREATMENT OF T-CELL EPITOPES OF SHORT H2A ONCOHISTONES

(71) Applicant: Fred Hutchinson Cancer Research Center, Seattle, WA (US)

(72) Inventors: Jay Francis Sarthy, Seattle, WA (US); Antoine Molaro, Clermont-Ferrand (FR); Marie Bleakley, Seattle, WA (US); Guo-Liang Chew, Singapore (SG)

(73) Assignee: Fred Hutchinson Cancer Center, Seattle, WA (US)

( * ) Notice: Subject to any disclaimer, the term of this patent is extended or adjusted under 35 U.S.C. 154(b) by 54 days.

(21) Appl. No.: 17/516,600

(22) Filed: Nov. 1, 2021

(65) Prior Publication Data

US 2022/0133760 A1   May 5, 2022

Related U.S. Application Data

(60) Provisional application No. 63/108,217, filed on Oct. 30, 2020.

(51) Int. Cl.
*A61K 31/704* (2006.01)
*A61K 31/136* (2006.01)
*A61P 35/00* (2006.01)
*C12Q 1/6886* (2018.01)

(52) U.S. Cl.
CPC .......... *A61K 31/704* (2013.01); *A61K 31/136* (2013.01); *A61P 35/00* (2018.01); *C12Q 1/6886* (2013.01); *C12Q 2600/112* (2013.01); *C12Q 2600/156* (2013.01); *C12Q 2600/158* (2013.01)

(58) Field of Classification Search
CPC ............ C12Q 1/6886; C12Q 2600/106; C12Q 2600/158; A61P 35/00
See application file for complete search history.

(56) References Cited

PUBLICATIONS

Chew (Nature Communications; 2021, 12:490; pp. 1-9).*
Anuar, Nur Diana, et al. "Gene editing of the multi-copy H2A. B gene and its importance for fertility." Genome biology 20.23 (2019): 1-16.
Bao, Yunhe, et al. "Nucleosomes containing the histone variant H2A. Bbd organize only 118 base pairs of DNA." The EMBO journal 23.16 (2004): 3314-3324.
Barretina, Jordi, et al. "The Cancer Cell Line Encyclopedia enables predictive modelling of anticancer drug sensitivity." Nature 483 (2012): 603-607.
Behan, Fiona M., et al. "Prioritization of cancer therapeutic targets using CRISPR-Cas9 screens." Nature (2019).
Bennett, Richard L., et al. "A mutation in histone H2B represents a new class of oncogenic driver." Cancer discovery 9.10 (2019): 1438-1451.
Chapuy, Bjoern, et al. "Molecular subtypes of diffuse large B cell lymphoma are associated with distinct pathogenic mechanisms and outcomes." Nature medicine 24.5 (2018): 679-690.
Chew, Guo-Liang, et al. "Short H2A histone variants are expressed in cancer." Nature communications 12.490 (2021): 1-9.
Corces, M. Ryan, et al. "The chromatin accessibility landscape of primary human cancers." Science 362.6413 (2018): eaav1898.
Doyen, Cécile-Marie, et al. "Dissection of the unusual structural and functional properties of the variant H2A. Bbd nucleosome." The EMBO journal 25.18 (2006): 4234-4244.
Dvinge, Heidi, et al. "RNA splicing factors as oncoproteins and tumour suppressors." Nature Reviews Cancer 16.7 (2016): 413-430.
Fratta, Elisabetta, et al. "The biology of cancer testis antigens: putative function, regulation and therapeutic potential." Molecular oncology 5.2 (2011): 164-182.
Glaich, Ohad, et al. "Histone H1. 5 binds over splice sites in chromatin and regulates alternative splicing." Nucleic acids research 47.12 (2019): 6145-6159.
Hoghoughi, Naghmeh, et al. "Histone variants: essential actors in male genome programming." The Journal of Biochemistry 163.2 (2018): 97-103.
Jain, Siddhant U., et al. "PFA ependymoma-associated protein EZHIP inhibits PRC2 activity through a H3 K27M-like mechanism." Nature communications 10.2146 (2019): 1-14.
Jimeno-González, Silvia, et al. "Defective histone supply causes changes in RNA polymerase II elongation rate and cotranscriptional pre-mRNA splicing." Proceedings of the National Academy of Sciences 112.48 (2015): 14840-14845.
Koh, Cheryl M., et al. "MYC regulates the core pre-mRNA splicing machinery as an essential step in lymphomagenesis." Nature 523 (2015): 96-100.
Kohestani, Havva, and Jeff Wereszczynski. "Effects of H2A. B incorporation on nucleosome structures and dynamics." bioRxiv 172130 (2020).
Lilljebjörn, Henrik, et al. "Identification of ETV6-RUNX1-like and DUX4-rearranged subtypes in paediatric B-cell precursor acute lymphoblastic leukaemia." Nature communications 7.11790 (2016): 1-13.
Liu, Yuan-Fang, et al. "Genomic profiling of adult and pediatric B-cell acute lymphoblastic leukemia." EBioMedicine 8 (2016): 173-183.
Luger, Karolin, et al. "Crystal structure of the nucleosome core particle at 2.8 Å resolution." Nature 389 (1997): 251-260.

(Continued)

*Primary Examiner* — Pancham Bakshi
(74) *Attorney, Agent, or Firm* — Christensen O'Connor Johnson Kindness, PLLC

(57) ABSTRACT

The present disclosure describes methods of treating lymphoma that expresses a short histone H2A variant. In some embodiments, the method can comprise collecting a sample from a subject having or suspected of having lymphoma, detecting a short histone H2A variant (sH2A) expression level in the sample collected from the subject, and administering to the subject a therapeutically effective dose of an anthracycline agent, if the subject has sH2A variant expression level that is detectable. In other embodiments, the sH2A is the H2A.B variant. In other embodiments, the anthracycline agent can be aclarubicin.

17 Claims, 36 Drawing Sheets

Specification includes a Sequence Listing.

(56) References Cited

PUBLICATIONS

Lundegaard, Claus, et al. "NetMHC-3.0: accurate web accessible predictions of human, mouse and monkey MHC class I affinities for peptides of length 8-11." Nucleic Acids Research. vol. 36. Web Server issue (2008): W509-W512.

Martire, Sara, et al. "Differential contribution of p300 and CBP to regulatory element acetylation in mESCs." BMC molecular and cell biology 21.1 (2020): 1-12.

Meyers, Robin M., et al. "Computational correction of copy number effect improves specificity of CRISPR-Cas9 essentiality screens in cancer cells." Nature genetics 49.12 (2017): 1779-1784.

Molaro, Antoine, Janet M. Young, and Harmit S. Malik. "Evolutionary origins and diversification of testis-specific short histone H2A variants in mammals." Genome research 28.4 (2018): 460-473.

Nacev, Benjamin A., et al. "The expanding landscape of 'oncohistone' mutations in human cancers." Nature 567 (2019): 473-478.

Nielsen, Morten, et al. "Reliable prediction of T-cell epitopes using neural networks with novel sequence representations." Protein Science 12.5 (2003): 1007-1017.

Peng, Junhui, et al. "Molecular mechanism of histone variant H2A. B on stability and assembly of nucleosome and chromatin structures." Epigenetics & chromatin 13.28 (2020): 1-14.

Piunti, Andrea, et al. "CATACOMB: An endogenous inducible gene that antagonizes H3K27 methylation activity of Polycomb repressive complex 2 via an H3K27M-like mechanism." Science advances 5.7 (2019): eaax2887.

Qian, Maoxiang, et al. "Whole-transcriptome sequencing identifies a distinct subtype of acute lymphoblastic leukemia with predominant genomic abnormalities of EP300 and CREBBP." Genome research 27.2 (2017): 185-195.

Reddy, Anupama, et al. "Genetic and functional drivers of diffuse large B cell lymphoma." Cell 171.2 (2017): 481-494.

Sansoni, Viola, et al. "The histone variant H2A. Bbd is enriched at sites of DNA synthesis." Nucleic acids research 42.10 (2014): 6405-6420.

Sarthy, Jay F., Steven Henikoff, and Kami Ahmad. "Chromatin bottlenecks in cancer." Trends in Cancer 5.3 (2019): 183-194.

Shen, Luhui, et al. "RNA transcription and splicing errors as a source of cancer frameshift neoantigens for vaccines." Scientific reports 9.14184 (2019): 1-13.

Siam, Ahmad, et al. "Regulation of alternative splicing by p300-mediated acetylation of splicing factors." Rna 25.7 (2019): 813-824.

Soboleva, Tatiana A., et al. "A new link between transcriptional initiation and pre-mRNA splicing: The RNA binding histone variant H2A. B." PLoS genetics 13.2 (2017): e1006633.

Thomas, James D., et al. "RNA isoform screens uncover the essentiality and tumor-suppressor activity of ultraconserved poison exons." Nature genetics 52.1 (2020): 84-94.

Tolstorukov, Michael Y., et al. "Histone variant H2A. Bbd is associated with active transcription and mRNA processing in human cells." Molecular cell 47.4 (2012): 596-607.

Valdés-Mora, Fátima, et al. "Acetylated histone variant H2A. Z is involved in the activation of neo-enhancers in prostate cancer." Nature Communications 8.1346 (2017): 1-17.

Valdés-Mora, Fátima, et al. "Acetylation of H2A. Z is a key epigenetic modification associated with gene deregulation and epigenetic remodeling in cancer." Genome research 22.2 (2012): 307-321.

Whitehurst, Angelique W. "Cause and consequence of cancer/testis antigen activation in cancer." Annual review of pharmacology and toxicology 54 (2014): 251-272.

Winkler, Carolin, et al. "Hodgkin's lymphoma RNA-transfected dendritic cells induce cancer/testis antigen-specific immune responses." Cancer Immunology, Immunotherapy 61.10 (2012): 1769-1779.

Xu, Jin, et al. "Free-living human cells reconfigure their chromosomes in the evolution back to uni-cellularity." Elife 6 (2017): e28070.

Yasuda, Takahiko, et al. "Recurrent DUX4 fusions in B cell acute lymphoblastic leukemia of adolescents and young adults." Nature genetics 48.5 (2016): 569-574.

\* cited by examiner

FIG. 1B

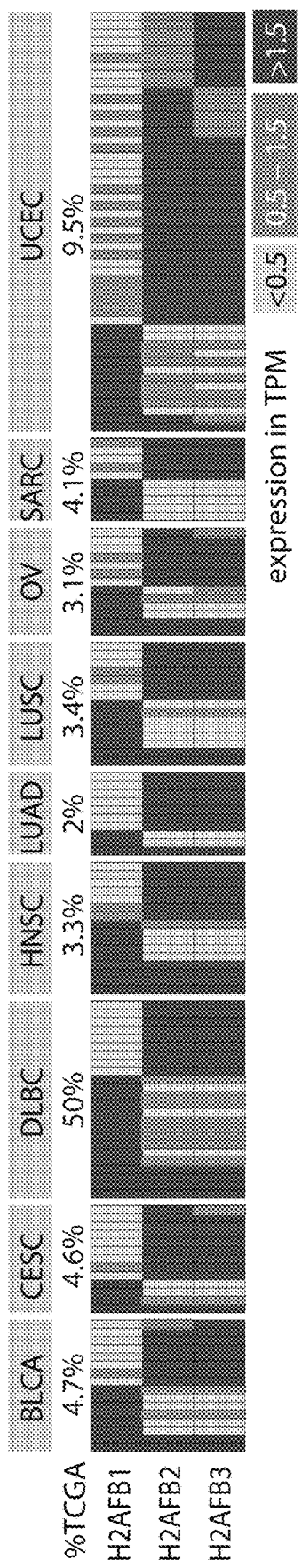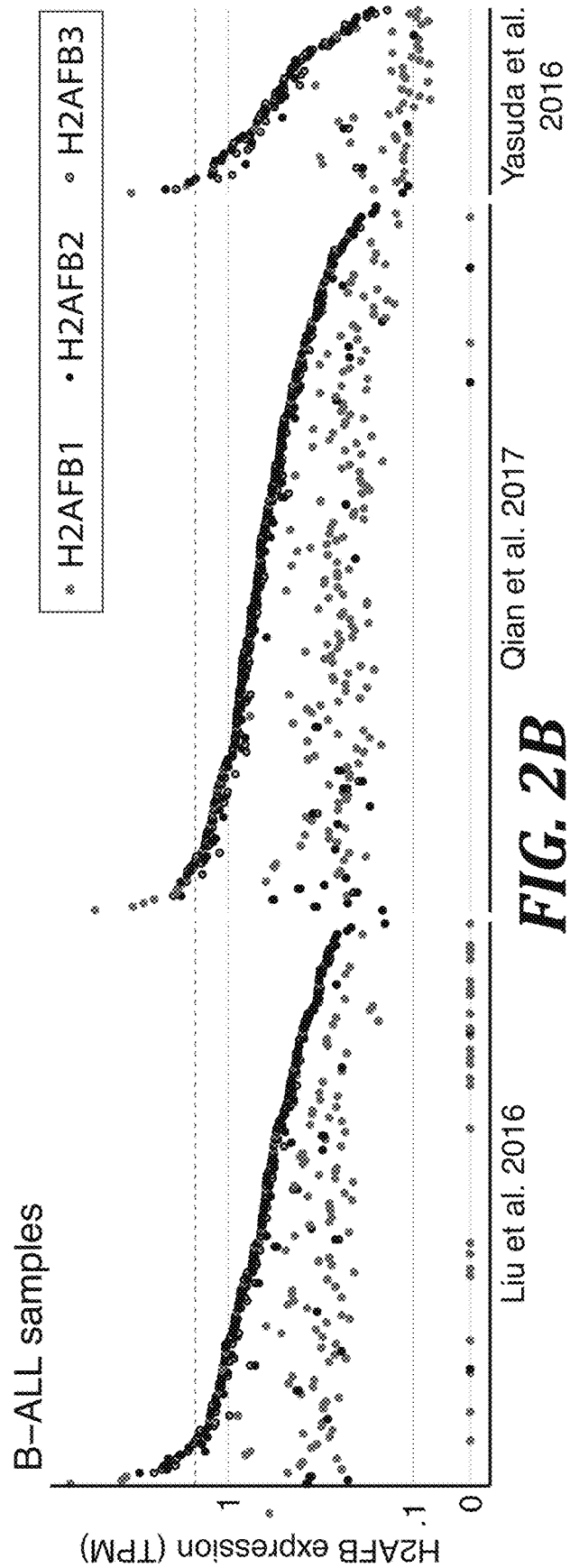
FIG. 2A
FIG. 2B

L-1236

L-428

SEQUENCE LISTING

```
<160> NUMBER OF SEQ ID NOS: 27

<210> SEQ ID NO 1
<211> LENGTH: 130
<212> TYPE: PRT
<213> ORGANISM: Homo sapiens

<400> SEQUENCE: 1

Met Ser Gly Arg Gly Lys Gln Gly Gly Lys Ala Arg Ala Lys Ala Lys
1               5                   10                  15

Ser Arg Ser Ser Arg Ala Gly Leu Gln Phe Pro Val Gly Arg Val His
                20                  25                  30

Arg Leu Leu Arg Lys Gly Asn Tyr Ser Glu Arg Val Gly Ala Gly Ala
            35                  40                  45

Pro Val Tyr Leu Ala Ala Val Leu Glu Tyr Leu Thr Ala Glu Ile Leu
        50                  55                  60

Glu Leu Ala Gly Asn Ala Ala Arg Asp Asn Lys Lys Thr Arg Ile Ile
65                  70                  75                  80

Pro Arg His Leu Gln Leu Ala Ile Arg Asn Asp Glu Glu Leu Asn Lys
                85                  90                  95

Leu Leu Gly Arg Val Thr Ile Ala Gln Gly Gly Val Leu Pro Asn Ile
            100                 105                 110

Gln Ala Val Leu Leu Pro Lys Lys Thr Glu Ser His His Lys Ala Lys
        115                 120                 125

Gly Lys
    130

<210> SEQ ID NO 2
<211> LENGTH: 131
<212> TYPE: PRT
<213> ORGANISM: Homo sapiens

<400> SEQUENCE: 2

Met Ser Gly Arg Gly Lys Gln Gly Gly Lys Ala Arg Ala Lys Ser Lys
1               5                   10                  15

Ser Arg Ser Ser Arg Ala Gly Leu Gln Phe Pro Val Gly Arg Ile His
                20                  25                  30

Arg Leu Leu Arg Lys Gly Asn Tyr Ala Glu Arg Ile Gly Ala Gly Ala
            35                  40                  45

Pro Val Tyr Leu Ala Ala Val Leu Glu Tyr Leu Thr Ala Glu Ile Leu
        50                  55                  60

Glu Leu Ala Gly Asn Ala Ser Arg Asp Asn Lys Lys Thr Arg Ile Ile
65                  70                  75                  80

Pro Arg His Leu Gln Leu Ala Ile Arg Asn Asp Glu Glu Leu Asn Lys
```

```
                   85                  90                  95

Leu Leu Gly Gly Val Thr Ile Ala Gln Gly Gly Val Leu Pro Asn Ile
            100                 105                 110

Gln Ala Val Leu Leu Pro Lys Lys Thr Glu Ser His His His Lys Ala
            115                 120                 125

Gln Ser Lys
    130

<210> SEQ ID NO 3
<211> LENGTH: 115
<212> TYPE: PRT
<213> ORGANISM: Homo sapiens

<400> SEQUENCE: 3

Met Pro Arg Arg Arg Arg Arg Gly Ser Ser Gly Ala Gly Gly Arg
1               5                   10                  15

Gly Arg Thr Cys Ser Arg Thr Val Arg Ala Glu Leu Ser Phe Ser Val
            20                  25                  30

Ser Gln Val Glu Arg Ser Leu Arg Glu Gly His Tyr Ala Gln Arg Leu
        35                  40                  45

Ser Arg Thr Ala Pro Val Tyr Leu Ala Ala Val Ile Glu Tyr Leu Thr
    50                  55                  60

Ala Lys Val Leu Glu Leu Ala Gly Asn Glu Ala Gln Asn Ser Gly Glu
65                  70                  75                  80

Arg Asn Ile Thr Pro Leu Leu Leu Asp Met Val Val His Asn Asp Arg
                85                  90                  95

Leu Leu Ser Thr Leu Phe Asn Thr Thr Thr Ile Ser Gln Val Ala Pro
            100                 105                 110

Gly Glu Asp
        115

<210> SEQ ID NO 4
<211> LENGTH: 115
<212> TYPE: PRT
<213> ORGANISM: Homo sapiens

<400> SEQUENCE: 4

Met Pro Arg Arg Arg Arg Arg Gly Ser Ser Gly Ala Gly Gly Arg
1               5                   10                  15

Gly Arg Thr Cys Ser Arg Thr Val Arg Ala Glu Leu Ser Phe Ser Val
            20                  25                  30

Ser Gln Val Glu Arg Ser Leu Arg Glu Gly His Tyr Ala Gln Arg Leu
        35                  40                  45

Ser Arg Thr Ala Pro Val Tyr Leu Ala Ala Val Ile Glu Tyr Leu Thr
    50                  55                  60

Ala Lys Val Pro Glu Leu Ala Gly Asn Glu Ala Gln Asn Ser Gly Glu
65                  70                  75                  80

Arg Asn Ile Thr Pro Leu Leu Leu Asp Met Val Val His Asn Asp Arg
                85                  90                  95

Leu Leu Ser Thr Leu Phe Asn Thr Thr Thr Ile Ser Gln Val Ala Pro
            100                 105                 110

Gly Glu Asp
        115

<210> SEQ ID NO 5
<211> LENGTH: 115
<212> TYPE: PRT
```

<213> ORGANISM: Pan troglodytes

<400> SEQUENCE: 5

Met Pro Arg Arg Arg His Arg Gly Ser Ser Gly Ala Gly Gly Arg
1               5                   10                  15

Gly Arg Thr Cys Ser Arg Thr Val Arg Ala Glu Leu Ser Phe Ser Val
            20                  25                  30

Ser Gln Val Glu Arg Ser Leu Arg Glu Gly Gln Tyr Ala Gln Arg Leu
        35                  40                  45

Ser Arg Thr Ala Pro Val Tyr Leu Ala Ala Val Ile Glu Tyr Leu Thr
    50                  55                  60

Ala Lys Val Leu Glu Leu Ala Gly Asn Glu Ala Gln Asn Ser Gly Ala
65                  70                  75                  80

Arg Asn Ile Thr Pro Leu Leu Leu Asp Met Val Val His Asn Asp Arg
                85                  90                  95

Leu Leu Ser Thr Leu Phe Asn Thr Thr Thr Ile Ser Gln Val Ala Pro
            100                 105                 110

Gly Glu Asp
        115

<210> SEQ ID NO 6
<211> LENGTH: 117
<212> TYPE: PRT
<213> ORGANISM: Pan paniscus

<400> SEQUENCE: 6

Met Pro Arg Arg Arg His Arg Gly Ser Ser Gly Ala Gly Gly Arg
1               5                   10                  15

Gly Arg Thr Cys Ser Arg Thr Val Arg Ala Glu Leu Ser Phe Ser Val
            20                  25                  30

Ser Gln Val Glu Arg Ser Leu Arg Glu Gly Gln Tyr Ala Gln Arg Leu
        35                  40                  45

Ser Arg Thr Ala Pro Val Tyr Leu Ala Ala Val Ile Glu Tyr Leu Thr
    50                  55                  60

Ala Lys Val Leu Glu Leu Ala Gly Asn Glu Ala Gln Asn Ser Gly Ala
65                  70                  75                  80

Arg Asn Ile Thr Pro Leu Leu Leu Asp Met Val Val His Asn Asp Arg
                85                  90                  95

Leu Leu Ser Thr Leu Phe Asn Thr Thr Thr Ile Ser Gln Val Ala Pro
            100                 105                 110

Ala Arg Thr Ser Phe
        115

<210> SEQ ID NO 7
<211> LENGTH: 115
<212> TYPE: PRT
<213> ORGANISM: Pan paniscus

<400> SEQUENCE: 7

Met Pro Arg Arg Arg His Arg Gly Ser Ser Gly Ala Gly Gly Arg
1               5                   10                  15

Gly Arg Thr Cys Ser Arg Thr Val Arg Ala Glu Leu Ser Phe Ser Val
            20                  25                  30

Ser Gln Val Glu Arg Ser Leu Arg Glu Gly Gln Tyr Ala Gln Arg Leu
        35                  40                  45

Ser Arg Thr Ala Pro Val Tyr Leu Ala Ala Val Ile Glu Tyr Leu Thr
    50                  55                  60

```
Ala Lys Val Leu Glu Leu Ala Gly Asn Glu Ala Gln Asn Ser Gly Ala
 65                  70                  75                  80

Arg Asn Ile Thr Pro Leu Leu Leu Asp Met Val Val His Asn Asp Arg
                 85                  90                  95

Leu Leu Ser Thr Leu Phe Asn Thr Thr Thr Ile Ser Gln Val Ala Pro
                100                 105                 110

Gly Glu Asp
        115

<210> SEQ ID NO 8
<211> LENGTH: 115
<212> TYPE: PRT
<213> ORGANISM: Gorilla

<400> SEQUENCE: 8

Met Pro Arg Arg Arg His Arg Gly Ser Gly Ala Gly Gly Arg
 1               5                  10                  15

Gly Arg Thr Cys Ser Arg Ala Val Arg Ala Glu Leu Ser Phe Ser Val
                 20                  25                  30

Ser Gln Val Glu Arg Ser Leu Arg Glu Gly His Tyr Ala Gln Arg Leu
             35                  40                  45

Ser Arg Thr Ala Pro Val Tyr Leu Ala Ala Val Ile Glu Tyr Leu Thr
         50                  55                  60

Ala Lys Val Leu Glu Leu Ala Gly Asn Glu Ala Gln Asn Ser Gly Glu
 65                  70                  75                  80

Arg Asn Ile Thr Pro Leu Leu Leu Asp Met Ala Val His Asn Asp Arg
                 85                  90                  95

Leu Leu Ser Thr Leu Phe Ser Ser Thr Thr Ile Ser Gln Ala Ala Pro
                100                 105                 110

Gly Glu Asp
        115

<210> SEQ ID NO 9
<211> LENGTH: 115
<212> TYPE: PRT
<213> ORGANISM: Pongo

<400> SEQUENCE: 9

Met Pro Arg Arg Arg Ser His Arg Gly Ser Ser Gly Ala Gly Gly Arg
 1               5                  10                  15

Gly Arg Thr Cys Ser Arg Thr Val Arg Ala Glu Leu Ser Phe Ser Val
                 20                  25                  30

Ser Gln Val Glu Arg Ser Leu Arg Glu Gly His Tyr Ala Gln Arg Leu
             35                  40                  45

Ser Arg Thr Ala Pro Val Tyr Leu Ala Ala Val Ile Glu Tyr Leu Thr
         50                  55                  60

Ala Lys Val Leu Glu Leu Ala Gly Asn Glu Ala Gln Asn Asn Gly Glu
 65                  70                  75                  80

Arg Asn Ile Thr Pro Leu Leu Leu Asp Met Val Val His Asn Asn Arg
                 85                  90                  95

Leu Leu Ser Thr Leu Phe Asp Thr Thr Thr Ile Ser Gln Val Ala Pro
                100                 105                 110

Gly Gly Asp
        115

<210> SEQ ID NO 10
```

```
<211> LENGTH: 115
<212> TYPE: PRT
<213> ORGANISM: Hylobatidae

<400> SEQUENCE: 10

Met Pro Arg Arg Arg Ser His Arg Gly Ser Ser Gly Ala Gly Gly Arg
1               5                   10                  15

Gly Arg Thr Cys Ser Arg Thr Val Arg Ala Glu Leu Ser Phe Ser Val
            20                  25                  30

Ser Gln Val Glu Arg Gly Leu Arg Glu Gly His Tyr Ala Gln Arg Leu
        35                  40                  45

Ser Arg Thr Ala Pro Val Tyr Leu Ala Ala Val Ile Glu Tyr Leu Thr
    50                  55                  60

Ala Lys Val Leu Glu Leu Ala Gly Asn Glu Ala Gln Asn Asn Gly Glu
65                  70                  75                  80

Arg Asn Ile Thr Pro Leu Leu Leu Asp Met Val Val His Asn Asn Arg
                85                  90                  95

Leu Leu Ser Thr Leu Phe His Thr Thr Thr Ile Ser Arg Val Ala Pro
            100                 105                 110

Gly Gly Asp
        115

<210> SEQ ID NO 11
<211> LENGTH: 115
<212> TYPE: PRT
<213> ORGANISM: Macaca

<400> SEQUENCE: 11

Met Ser Glu Arg Arg Ser His Arg Arg Ser Ser Arg Ala Gly Gly Arg
1               5                   10                  15

Gly Arg Thr Arg Ser Arg Thr Val Arg Ala Glu Leu Ser Phe Ser Val
            20                  25                  30

Ser Gln Val Glu Arg Gly Leu Arg Glu Gly His Tyr Ala Gln Arg Leu
        35                  40                  45

Ser Pro Thr Ala Pro Val Tyr Leu Ala Ala Val Ile Glu Tyr Leu Thr
    50                  55                  60

Ala Lys Val Leu Glu Leu Ala Gly Asn Glu Ala Gln Asn Asn Gly Glu
65                  70                  75                  80

Arg Asn Ile Thr Pro Leu Leu Leu Asp Met Ala Val His Asn Asn Arg
                85                  90                  95

Leu Leu Ser Thr Leu Phe Asp Thr Thr Thr Ile Ser Gln Val Ala Pro
            100                 105                 110

Gly Gly Asp
        115

<210> SEQ ID NO 12
<211> LENGTH: 115
<212> TYPE: PRT
<213> ORGANISM: Papio

<400> SEQUENCE: 12

Met Ser Gly Arg Arg Ser His Arg Arg Ser Ser Gly Ala Gly Gly Arg
1               5                   10                  15

Gly Gln Thr Arg Ser Arg Thr Val Arg Ala Glu Leu Ser Phe Ser Val
            20                  25                  30

Ser Gln Val Glu Arg Gly Leu Arg Glu Gly His Tyr Ala Gln Arg Leu
        35                  40                  45
```

Ser Pro Thr Ala Pro Val Tyr Leu Ala Ala Val Ile Glu Tyr Leu Thr
 50                  55                  60

Ala Lys Val Leu Glu Leu Ala Gly Asn Glu Ala Gln Asp Asn Gly Glu
65                  70                  75                  80

Arg Thr Ile Thr Pro Leu Leu Leu Asp Arg Ala Val His Asn Asn Arg
                85                  90                  95

Leu Leu Ser Thr Leu Phe Asp Thr Thr Ile Ile Ser Gln Val Ala Pro
            100                 105                 110

Gly Gly Asp
        115

<210> SEQ ID NO 13
<211> LENGTH: 115
<212> TYPE: PRT
<213> ORGANISM: Callithrix jacchus

<400> SEQUENCE: 13

Met Ser Glu Arg Arg Ser Arg Arg Gly Ser Ser Ala Ala Gly Arg Arg
1               5                   10                  15

Gly His Thr Arg Ser Arg Thr Ala Arg Ala Glu Leu Ile Phe Ser Val
            20                  25                  30

Ser Gln Met Glu Arg Gly Leu Trp Glu Gly His Tyr Ala Gln Arg Leu
        35                  40                  45

Ser Asp Asn Ala Pro Val Tyr Leu Ala Ala Val Ile Gln Tyr Leu Thr
 50                  55                  60

Ala Lys Ile Leu Glu Leu Ala Ala Lys Glu Ala Asp Asn Arg Gly Glu
65                  70                  75                  80

Arg Ile Ile Thr Pro Arg Leu Leu Asp Met Ala Val His Asn Asp Gly
                85                  90                  95

Leu Leu Ser Thr Leu Phe His Ala Ile Thr Ile Ser Gln Val Gly Pro
            100                 105                 110

Gly Pro Asn
        115

<210> SEQ ID NO 14
<211> LENGTH: 115
<212> TYPE: PRT
<213> ORGANISM: Callithrix jacchus

<400> SEQUENCE: 14

Met Leu Gly Arg Arg Ser Arg Arg Gly Ser Ser Gly Ala Gly Gly Arg
1               5                   10                  15

Gly His Thr Leu Ser Arg Thr Ala Arg Gly Glu Leu Leu Phe Ser Val
            20                  25                  30

Ser Glu Val Glu Arg Ser Leu Gln Glu Gly Gln Cys Ala Gln Arg Leu
        35                  40                  45

Ser Pro Ser Ala Pro Val Tyr Leu Ala Ala Val Ile Gln Tyr Leu Thr
 50                  55                  60

Ala Gln Ile Leu Glu Leu Ala Gly Lys Glu Ala His Asn Asn Gly Glu
65                  70                  75                  80

Arg Thr Ile Thr Pro Gln Pro Leu Asp Met Ala Val His Asp Asn Ala
                85                  90                  95

Leu Leu Ser Thr Leu Phe Asp Thr Thr Thr Val Ser Gln Val Val Pro
            100                 105                 110

Gly Arg Asp
        115

<210> SEQ ID NO 15
<211> LENGTH: 117
<212> TYPE: PRT
<213> ORGANISM: Homo sapiens

<400> SEQUENCE: 15

Met Ser Glu Lys Lys Asn Cys Lys Asn Ser Ser Thr Asn Asn Asn Gln
1               5                   10                  15

Thr Gln Asp Pro Ser Arg Asn Glu Leu Gln Val Pro Arg Ser Phe Val
            20                  25                  30

Asp Arg Val Val Gln Asp Glu Arg Asp Val Gln Ser Gln Ser Ser Ser
        35                  40                  45

Thr Ile Asn Thr Leu Leu Thr Leu Leu Asp Cys Leu Ala Asp Tyr Ile
    50                  55                  60

Met Glu Arg Val Gly Leu Glu Ala Ser Asn Asn Gly Ser Met Arg Asn
65                  70                  75                  80

Thr Ser Gln Asp Arg Glu Arg Glu Val Asp Asn Asn Arg Glu Pro His
                85                  90                  95

Ser Ala Glu Ser Asp Val Thr Arg Phe Leu Phe Asp Glu Met Pro Lys
            100                 105                 110

Ser Arg Lys Asn Asp
        115

<210> SEQ ID NO 16
<211> LENGTH: 117
<212> TYPE: PRT
<213> ORGANISM: Pan troglodytes

<400> SEQUENCE: 16

Met Ser Glu Lys Lys Asn Cys Lys Asn Ser Ser Thr Asn Asn Asn Gln
1               5                   10                  15

Thr Gln Asp Pro Ser Arg Asn Glu Leu Gln Val Pro Met Ser Phe Val
            20                  25                  30

Asp Arg Val Val Gln Asp Glu Arg Asp Val Gln Ser Gln Ser Ser Ser
        35                  40                  45

Thr Ile Asn Thr Leu Leu Thr Leu Leu Asp Cys Leu Ala Asp Tyr Ile
    50                  55                  60

Met Glu Arg Val Gly Leu Glu Ala Ser Asn Asn Gly Ser Met Arg Asn
65                  70                  75                  80

Thr Ser Gln Asp Arg Glu Arg Glu Val Asp Asn Asn Arg Glu Pro His
                85                  90                  95

Ser Ala Glu Ser Asp Val Thr Arg Phe Leu Phe Asp Glu Met Pro Lys
            100                 105                 110

Ser Arg Lys Asn Asp
        115

<210> SEQ ID NO 17
<211> LENGTH: 117
<212> TYPE: PRT
<213> ORGANISM: Papio

<400> SEQUENCE: 17

Met Ser Glu Lys Asn Asn Arg Lys Asn Ser Ser Thr Asn Asn Asn Gln
1               5                   10                  15

Thr Gln Asp Arg Ser Arg Asn Glu Leu Arg Val Pro Met Ser Phe Val
            20                  25                  30

Asp Arg Val Val Gln Asp Glu Gln Asp Ala Gln Ser Gln Ser Ser Ser

```
                35                  40                  45
Thr Ile Asn Ile Leu Leu Thr Leu Leu Asp Cys Leu Ala Asp Tyr Ile
                50                  55                  60
Met Glu Gln Val Gly Leu Glu Val Ile Asn Asn Gly Arg Met Arg Asn
 65                  70                  75                  80
Thr Ser Gln Asp Gly Glu Arg Glu Val Asp Asn His His Glu Pro His
                 85                  90                  95
Arg Thr Glu Ser Asp Gly Thr Arg Phe Val Phe Asp Glu Met Pro Lys
                100                 105                 110
Ser Gly Lys Asn Asp
            115

<210> SEQ ID NO 18
<211> LENGTH: 117
<212> TYPE: PRT
<213> ORGANISM: Callithrix jacchus

<400> SEQUENCE: 18

Met Ser Glu Thr Glu Asn Cys Lys Asn Ser Pro Thr Asn Asn Asn Gln
 1               5                  10                  15
Asn Gln Glu Pro Ser Arg Asn Glu Pro Gln Val Pro Arg Thr Phe Val
                20                  25                  30
Asp Arg Leu Leu Gln Asp Glu Arg Asp Ala Gln Ser Gln Thr Ser Ser
                35                  40                  45
Met Ile Asn Ser Leu Leu Thr Leu Leu Asp Cys Leu Gly Asp Phe Ile
                50                  55                  60
Met Glu Gln Val Gly Leu Glu Ala Ser His Asn Asp Ser Met Asn Asn
 65                  70                  75                  80
Thr Ser Gln Asp Ala Glu Arg Glu Val Asp Asn Asn Arg Glu Pro His
                 85                  90                  95
Cys Leu Glu Ser Asp Ile Thr Cys Phe Leu Leu Asp Gly Met Pro Lys
                100                 105                 110
Ser Glu Lys Asn Gly
            115

<210> SEQ ID NO 19
<211> LENGTH: 99
<212> TYPE: PRT
<213> ORGANISM: Homo sapiens

<400> SEQUENCE: 19

Met Phe Ser Lys Arg Arg Gln Arg Ser Ser Tyr Arg Cys Arg Asn Gln
 1               5                  10                  15
Thr Phe Ser Tyr Ser Ile Arg Ala Lys Gln Gln Phe Leu Leu Ser Cys
                20                  25                  30
Val His Cys Leu Leu Trp Lys Asn His Cys Pro Arg Pro Glu Leu Val
                35                  40                  45
His Tyr Phe Gln Ile Leu Gly Gly Asn Ile Leu Glu Leu Met Gly Asn
                50                  55                  60
Lys Val His Lys Asn Tyr Arg Met His Ile Thr Pro Lys Tyr Val Glu
 65                  70                  75                  80
Arg Val Val Asp Asn Asn Pro Leu Leu Ser His Leu Phe Glu Gly Asp
                 85                  90                  95
Thr Asn Ser

<210> SEQ ID NO 20
```

```
<211> LENGTH: 99
<212> TYPE: PRT
<213> ORGANISM: Pan troglodytes

<400> SEQUENCE: 20

Met Phe Trp Lys Arg Arg Gln Arg Ser Ser Tyr Arg Cys Arg Asn Gln
1               5                   10                  15

Thr Phe Ser Tyr Ser Ile Arg Ala Lys Gln Gln Phe Leu Leu Ser Cys
            20                  25                  30

Val His Cys Leu Leu Trp Lys Asn His Cys Pro Arg Pro Glu Leu Val
        35                  40                  45

His Tyr Phe Gln Ile Leu Gly Gly Asn Ile Leu Glu Leu Met Gly Asn
    50                  55                  60

Lys Val His Lys Asn Tyr Arg Met His Ile Thr Pro Lys Tyr Val Glu
65                  70                  75                  80

Arg Val Val Asp Asn Asn Pro Leu Leu Ser His Leu Phe Glu Gly Asp
                85                  90                  95

Arg Asn Ser

<210> SEQ ID NO 21
<211> LENGTH: 98
<212> TYPE: PRT
<213> ORGANISM: Papio

<400> SEQUENCE: 21

Met Phe Trp Lys Arg Arg Gln Arg Ser Tyr Arg Cys Arg Asn Gln
1               5                   10                  15

Thr Phe Ser Tyr Ser Ile Lys Ala Lys Gln Gln Phe Pro Leu Ser Cys
            20                  25                  30

Val His Cys Leu Leu Trp Lys Asn His Cys Pro Arg Gln Glu Leu Val
        35                  40                  45

His Tyr Phe Gln Ile Leu Gly Gly Asn Ile Leu Glu Leu Met Gly Asn
    50                  55                  60

Lys Val His Lys Asn Tyr Arg Met His Ile Thr Pro Lys Tyr Val Glu
65                  70                  75                  80

Arg Ala Val Asp Asn Asn Ser Leu Ile Ser His Leu Phe Glu Gly Asp
                85                  90                  95

Thr Asn

<210> SEQ ID NO 22
<211> LENGTH: 29
<212> TYPE: PRT
<213> ORGANISM: Callithrix jacchus

<400> SEQUENCE: 22

Met Phe Trp Lys Arg Ser Gln Arg Ser Ser Tyr Arg Cys Arg Asn Gln
1               5                   10                  15

Thr Phe Ser Tyr Ser Ile Arg Val Arg Gln Gln Phe Pro
            20                  25

<210> SEQ ID NO 23
<211> LENGTH: 57
<212> TYPE: PRT
<213> ORGANISM: Callithrix jacchus

<400> SEQUENCE: 23

Ser Cys Val His Cys Leu Leu Trp Lys Asn His Cys Pro Arg Pro Glu
1               5                   10                  15
```

Ile Val His His Val Gln Ile Leu Gly Gly Asn Ile Leu Glu Leu Met
               20                  25                  30

Ser Asn Lys Leu His Lys Asn Tyr Arg Met His Val Thr Pro Lys Tyr
           35                  40                  45

Val Glu Arg Val Val Asp Asn Asn Ser
       50                  55

<210> SEQ ID NO 24
<211> LENGTH: 11
<212> TYPE: PRT
<213> ORGANISM: Callithrix jacchus

<400> SEQUENCE: 24

Leu Ser His Leu Phe Glu Gly Asp Ile Asn Ser
1               5                   10

<210> SEQ ID NO 25
<211> LENGTH: 587
<212> TYPE: DNA
<213> ORGANISM: Artificial sequence
<220> FEATURE:
<223> OTHER INFORMATION: Synthetic

<400> SEQUENCE: 25
actggacgcg gtaactgtcc tcttgagagc catcttgcct agctgggcca agccgagata     60
gcacactcaa cgcccagcat gccgaggagg aggagacgcc gagggtcctc cggtgctggc    120
ggccgggggc ggacctgctc tcgcaccgtc cgagcggagc tttcgttttc agtgagccag    180
gtggagcgca gtctacggga gggccactac gctcagcgcc tgagtcgcac ggcgccggtc    240
tacctcgctg cggttattga gtacctgacg gccaaggtcc cggagctggc gggcaacgag    300
gcccagaaca gcggagagcg gaacatcact cccctgctgc tggacatggt ggttcacaac    360
gacaggctac tgagcaccct tttcaacacg accaccatct ctcaagtggc cctggcgag    420
gactagcttc tgcacccgg ccctgggac ctgacaggtc cactcgtcca cccacccggc     480
cccaaatccc ccggcctgaa ccccggcct aaacaccct ccccccacaa cccaggcccc      540
aaagtcttgg gccttcatta attctgtcaa taaaatgttt caaggaa                 587

<210> SEQ ID NO 26
<211> LENGTH: 591
<212> TYPE: DNA
<213> ORGANISM: Artificial sequence
<220> FEATURE:
<223> OTHER INFORMATION: Synthetic

<400> SEQUENCE: 26
actggacgcg gtaactgtcc tcttgagagc catcttgcct agctgggcca agccgagata     60
gcacactcaa cgcccagcat gccgaggagg aggagacgcc gagggtcctc cggtgctggc    120
ggccgggggc ggacctgctc tcgcaccgtc cgagcggagc tttcgttttc agtgagccag    180
gtggagcgca gtctacggga gggccactac gctcagcgcc tgagtcgcac ggcgccggtc    240
tacctcgctg cggttattga gtacctgacg gccaaggtcc tggagctggc gggcaacgag    300
gcccagaaca gcggagagcg gaacatcact cccctgctgc tggacatggt ggttcacaac    360
gacaggctac tgagcaccct tttcaacacg accaccatct ctcaagtggc cctggcgag    420
gactagcttc tgcacccgg ccctgggac ctgacaggtc cactcgtcca cccacccggc     480
cccaaatccc ccggcctgaa ccccggcct aaacaccct ccccccacaa cccaggcccc      540
aaagtcttgg gccttcatta attctgtcaa taaaatgttt caaggaagcc a            591

```
<210> SEQ ID NO 27
<211> LENGTH: 591
<212> TYPE: DNA
<213> ORGANISM: Artificial sequence
<220> FEATURE:
<223> OTHER INFORMATION: Synthetic

<400> SEQUENCE: 27
actggacgcg gtaactgtcc tcttgagagc catcttgcct agctgggcca agccgagata        60
gcacactcaa cgcccagcat gccgaggagg aggagacgcc gagggtcctc cggtgctggc       120
ggccgggggc ggacctgctc tcgcaccgtc cgagcgagc tttcgttttc agtgagccag        180
gtggagcgca gtctacggga gggccactac gctcagcgcc tgagtcgcac ggcgccggtc       240
tacctcgctg cggttattga gtacctgacg gccaaggtcc tggagctggc gggcaacgag       300
gcccagaaca gcggagagcg gaacatcact cccctgctgc tggacatggt ggttcacaac       360
gacaggctac tgagcaccct tttcaacacg accaccatct ctcaagtggc ccctggcgag       420
gactagcttc tgacacccgg cccctgggac ctgacaggtc cactcgtcca cccacccggc       480
cccaaatccc ccggcctgaa ccccgggcct taaacaccct ccccccacaa cccaggcccc       540
aaagtcttgg gccttcatta attctgtcaa taaaatgttt caaggaagcc a                591
```

IDENTIFICATION AND TREATMENT OF T-CELL EPITOPES OF SHORT H2A ONCOHISTONES

CROSS-REFERENCE(S) TO RELATED APPLICATION(S)

This application claims the benefit of U.S. Provisional Application No. 63/108,217, filed Oct. 30, 2020, the disclosure of which is hereby incorporated by reference in its entirety.

STATEMENT OF GOVERNMENT LICENSE RIGHTS

This invention was made with Government support under GM074108 awarded by the National Institutes of Health. The Government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is 1896-P44US_Seq_List_FINAL_20211029_ST25.txt. The text file is 26 KB; was created on Oct. 29, 2021 and is being submitted via EFS-Web with the filing of the specification.

BACKGROUND

Nucleosomes, the fundamental subunit of chromatin, consist of octamers of histones (H2A, H2B, H3, and H4) that wrap 147 bp of DNA. Single allele mutations in histones, termed "oncohistones", are found in many different malignancies. Oncohistones comprise small percentages of the total histone pool and rarely cause cancer by themselves. Instead, they synergize with other oncogenes to facilitate development of neoplastic chromatin landscapes. Recent large-scale cancer genome analyses identified recurrent mutations in histones within the highly conserved histone fold domain (HFD) in many common cancers. These HFDs mutations, including the well-characterized H2B-E76K substitution, reduce nucleosome stability in vitro and perturb chromatin in vivo. Similarly, most H2A HFD oncohistone mutations disrupt either contact sites with DNA (R29Q) or inter-nucleosomal interactions (acidic patch) (FIG. 1A). Cells co-expressing H2B-E76K and a PI3KCA oncogene showed increased transformation capacity, consistent with nucleosome instability enhancing the cancerogenic potential of other oncogenes.

Short histone H2A variants (sH2A) are a class of histone variants expressed during mammalian spermatogenesis. Regulation of sH2A expression in normal testis is unknown. Unlike other histone variants, sH2As are rapidly evolving and possess highly divergent HFDs, mutated acidic patches and truncated C-termini, all of which impact nucleosome stability. The best characterized of these variants, H2A.B, forms unique nucleosomes that wrap ~120 bp of DNA both in vitro and in vivo. In testis, H2A.B is incorporated into nucleosomes during meiosis and has been shown to interact with splicing factors at actively transcribed genes. Germline disruption of H2A.B-encoding genes in mice revealed that H2A.B loss is associated with chromatin dysfunction and splicing changes in testis.

Though a role for sH2As in cancer has yet to be determined, the emerging literature on nucleosome instability as a cancer driver along with H2A.B's potent ability to destabilize nucleosomes prompted the inventors to investigate whether sH2As can contribute to cancer. Previous work showed that expression of H2A.B causes increased sensitivity to DNA damaging agents, shortens S-phase and alters splicing, each of which are associated with oncogenesis. Additional evidence for a role for H2A.B in cancer comes from Hodgkin's lymphoma (HL), where, H2A.B transcripts have been detected and HL cells expressing H2A.B grow faster than H2A.B-negative cells. Here, through comparative analyses of germline short H2A sequences and oncohistone mutations in canonical H2A, short H2As were shown to inherently possess oncohistone features. Several cancer datasets were explored, and it was found that H2A.B is expressed in a diverse array of malignancies; and many of these cancers possess unique splicing signatures. The inventors propose that the nucleosome-destabilizing characteristics sH2As evolved for their role in testis result in oncohistone activity in other tissues.

Therefore, based on the knowledge that H2A.B is expressed in a variety of malignancies, a new need is revealed for the identification and treatment of H2A.B expressing malignancies. The present disclosure addresses these and related needs.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

Disclosed herein are embodiments of a method for treating a subject with lymphoma. In some embodiments, the method can comprise collecting a sample from a subject having or suspected of having lymphoma; detecting a short histone H2A variant (sH2A) expression level in the sample collected from the subject; and administering to the subject a therapeutically effective dose of an anthracycline agent, if the subject has sH2A variant expression level that is detectable.

In some embodiments, the sample can comprise blood, serum, plasma, or components thereof. In some embodiments, the sH2A variant can be the H2A.B variant. In some embodiments, the H2A.B variant has SEQ ID NO:3. In some embodiments, the H2A.B variant has a SEQ ID NO:4. In still other embodiments, the anthracycline agent can be selected from the group of daunorubicin, doxorubicin, epirubicin, idarubicin, mitoxantrone, valrubicin, and aclarubicin. In some embodiments, the anthracycline agent can be aclarubicin. In still other embodiments, the lymphoma can be Hodgkin's lymphoma.

Disclosed herein are embodiments of a method of inducing cytotoxicity in a lymphoma cell expressing a short histone H2A (sH2A) variant. In some embodiments, the method can comprise administering to a subject in need thereof a pharmaceutical composition comprising a therapeutically effective dose of an anthracycline agent.

In some embodiments, the subject can have Hodgkin's lymphoma. In some embodiments, the anthracycline agent can be selected from the group of daunorubicin, doxorubicin, epirubicin, idarubicin, mitoxantrone, valrubicin, and aclarubicin. In still other embodiments, the anthracycline agent can be aclarubicin. In some embodiments, the sH2A variant can be the H2A.B variant. In some embodiments, the H2A.B variant has SEQ ID NO:3. In some embodiments, the H2A.B variant has a SEQ ID NO:4. In still other embodiments, the H2A.B variant can be a protein encoded by histone H2A-Barr body-deficient type 1 (H2AFB1) (SEQ ID NO:25). In some embodiments, the H2A.B variant can be a protein encoded by histone H2A-Barr body-deficient type 2 (H2AFB2) (SEQ ID NO:26). In some embodiments, the H2A.B variant can be a protein encoded by histone H2A-Barr body-deficient type 3 (H2AFB3) (SEQ ID NO:27).

Disclosed herein are embodiments of a method to inhibit cancer cell proliferation. The method can comprise, collecting a sample from a subject having or suspected of having lymphoma; detecting a short histone H2A variant (sH2A) expression level in the sample collected from the subject; and administering to the subject a therapeutically effective dose of an anthracycline agent, if the subject has sH2A variant expression level that is detectable.

In some embodiments, the lymphoma can be selected from the group of diffuse large B-cell lymphomas (DLBCL), anaplastic large cell lymphoma (ALCL), and Hodgkin's lymphoma. In some embodiments, the lymphoma can be Hodgkin's lymphoma. In some embodiments, the sample can comprise blood, serum, plasma, or components thereof. In still other embodiments, the sH2A variant can be the H2A.B variant. In some embodiments, the H2A.B variant has SEQ ID NO:3. In some embodiments, the H2A.B variant has a SEQ ID NO:4. In some embodiments, the anthracycline agent can be selected from the group of daunorubicin, doxorubicin, epirubicin, idarubicin, mitoxantrone, valrubicin, and aclarubicin. In some embodiments, the anthracycline agent can be aclarubicin.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

Figure 1B:
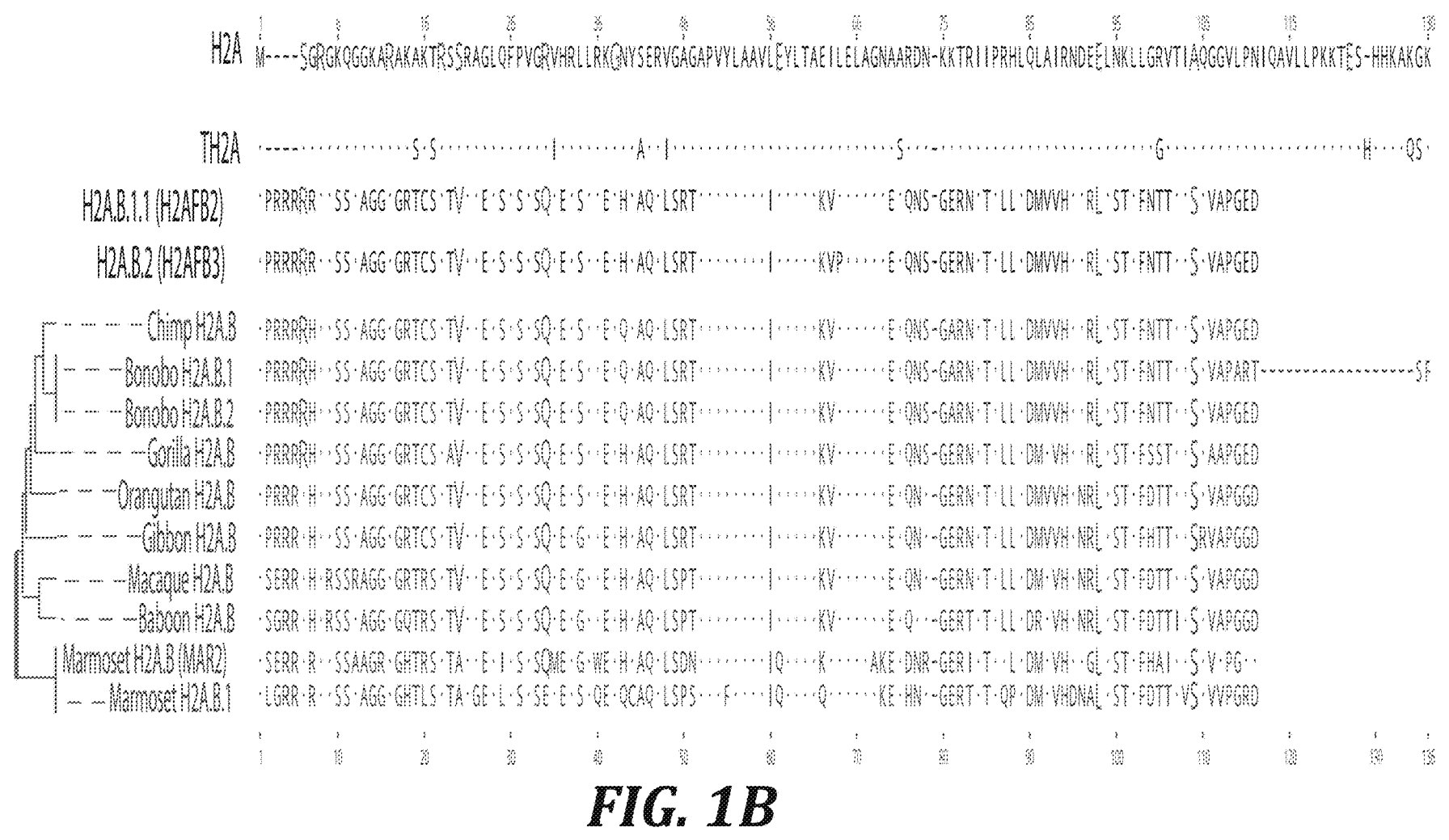

FIGS. 1A to 1B. H2A.B possesses oncohistone features that are conserved throughout primates. FIG. 1A. Schematic of common oncomutations found in human core H2A and their status in H2A.B. Marked sites on core H2A show WT amino acid position followed by its most common cancer-specific substitution in TCGA (H2A, vertical bars). Associated sites found in WT short H2As are shown in H2A.B as vertical bars. FIG. 1B. Protein alignment of core H2A, testis-specific H2A (TH2A), and H2A.B paralogs from Human and representative primates. Substitutions corresponding to oncohistone mutations in H2A (see FIG. 1A) are shown as larger font. Sequence identifiers for the sequences listed in FIG. 1B: H2A (SEQ ID NO:1); TH2A (SEQ ID NO:2); H2A.B.1.1 (H2AFB2) (SEQ ID NO:3); H2A.B.2 (H2AFB3) (SEQ ID NO:4); Chimp H2A.B (SEQ ID NO:5); Bonobo H2A.B.1 (SEQ ID NO:6); Bonobo H2A.B.2 (SEQ ID NO:7); Gorilla H2A.B (SEQ ID NO:8); Orangutan H2A.B (SEQ ID NO:9); Gibbon H2A.B (SEQ ID NO:10); Macaque H2A.B (SEQ ID NO:11); Baboon H2A.B (SEQ ID NO:12); Marmoset H2A.B (MAR2) (SEQ ID NO:13); Marmoset H2A.B.1 (SEQ ID NO:14);

FIGS. 2A to 2C. H2A.B is expressed in a broad array of cancers. FIG. 2A. Heat map illustrating the co-expression of H2A.B paralogues in individual tumors that express any one H2A.B paralogue (at >1.5 TPM as measured by RNA-seq), for cancer types with at least 10 tumors expressing any H2A.B paralogue. Percentages of tumors for each cancer type that express any H2A.B paralogue are shown. FIG. 2B. Expression levels (TPM) of H2A.B-encoding transcripts in three independent B-acute lymphoblastic leukemia data sets, horizontal line demarcates 1.5 TPM as measured by RNA-seq. Only samples with non-zero expression of any H2A.B paralog are shown: 18, 5, and 1 samples are omitted from Liu, Y. F. et al. (Genomic profiling of adult and pediatric B-cell acute lymphoblastic leukemia. *EBioMedicine* 8, 173-183 (2016)), Qian, M. et al. (Whole-transcriptome sequencing identifies a distinct subtype of acute lymphoblastic leukemia with predominant genomic abnormalities of EP300 and CREBBP. *Genome Res.* 27, 185-195 (2017)), and Yasuda, T. et al. (Recurrent DUX4 fusions in B cell acute lymphoblastic leukemia of adolescents and young adults. *Nat. Genet.* 48, 569-574 (2016)), respectively. FIG. 2C. As in FIG. 2B, but for cancer cell lines from CCLE, grouped by their lineage. Only lineages with any sample >1.5 TPM, and samples with non-zero expression of any H2A.B paralog are shown.

FIG. 3A. Scatter plot of gene expression differences (expressed as fold-change), comparing H2AFB1-positive against negative tumors (x axes), and H2AFB2/3-positive against negative tumors (y axes). The borders show genes that are commonly up- or downregulated at >1.19-fold. Pearson correlation coefficient is also shown. FIG. 3B. Boxplots comparing levels of H2A.Z (H2AFZ), H3.3 (H3F3A), H2A.X (H2AFX), and NAP1 (NAP1L1) transcripts in H2A.B-positive (under each column, the boxplot on the right) vs negative (under each column, the boxplot of the left) cancers from TCGA and B-ALL data sets. Asterisks show the statistical significance of the difference in TPMs by a two-sided Mann-Whitney U test. *$p<0.05$; $p<0.01$; **$p<0.000001$; *****$p<0.0000001$. Number of cancer samples in each group are listed in Table 2. Boxplots indicate the 1st quartile, median and 3rd quartile, whereas the whiskers extend from the box-ends to values no larger/smaller than 1.5 times of the inter-quartile range. All data points are additionally plotted. FIG. 3C Boxplots as in FIG. 3B, comparing CTAs scores in H2A.B-positive (under each column, the boxplot on the right) and negative (under each column, the boxplot of the left) cancers in TCGA and B-ALL cancers. For each tumor, the expression of CTAs is summarized as a CTA score: the sum Z-normalized log expression of the top 40 most variably expressed CTAs (within each cancer type). Asterisks show the statistical significance of the difference in CTA scores by a one-sided Mann-Whitney U test. *$p<0.05$; **$p<0.01$. Outlier points beyond the whiskers are additionally plotted.

FIG. 4A. Bar graphs showing the percentage of up- and downregulated splicing events (constitutive and alternative) when comparing H2A.B-positive to negative tumors, for cancer types with at least 10 tumors expressing any H2A.B paralogue. FIG. 4B. Scatter plots of alternative cassette exon inclusion for various cancers, comparing individual events from H2A.B-positive (y-axes) to negative tumors (x-axes). Axes units are fraction of transcripts that include the alternative cassette exon (Psi). Points above the shaded area and points below the shaded area indicate events that are significantly up- or downregulated (respectively) in H2A.B-positive tumors, at a threshold of $p<0.05$ (one-sided Mann-Whitney test) and the difference in Psi>0.1. The number of significantly up- and downregulated events are tallied in the bottom of each panel. FIG. 4C. As in FIG. 4A, but for B-ALL data sets.

FIG. 5A. Schematic of common oncomutations found in human core H2A and their status in H2A.P and H2A.Q. FIG. 5B. Protein alignment of canonical H2A and H2A.P from human and representative primates. Substitutions corresponding to oncohistone mutations in H2A (see FIG. 1A) are shown in larger font. FIG. 5C. Protein alignment of canonical H2A and H2A.Q from human and representative primates. Substitutions corresponding to oncohistone mutations in H2A (see FIG. 1A) are shown in larger font. Sequence identifiers for the sequences listed in FIG. 5B: H2A (SEQ ID NO:1); H2A.P (SEQ ID NO:15); Chimp H2A.P (SEQ ID NO:16); Baboon H2A.P (SEQ ID NO:17); Marmoset H2A.P (SEQ ID NO:18). Sequence identifiers for the sequences listed in FIG. 5C: H2A (SEQ ID NO:1); H2A.Q (SEQ ID NO:19); Chimp H2A.Q (SEQ ID NO:20); Baboon H2A.Q (SEQ ID NO:21); Marmoset H2A.Q (P) (amino acids 1-29 SEQ ID NO:22; amino acids 31-94 SEQ ID NO:23; amino acids 96-106 SEQ ID NO:24).

FIG. 6A. Mean expression of genes on autosomes (above) and the X-chromosome (below) in various cancers (columns) comparing tumors with reactivated (gray line) or silent (black line) H2A.B, plotted as a cumulative distribution. Only genes with non-zero mean expression (in both reactivated and silent tumors) are shown. Apart from minor differences in the low range that may be explained by differences in group sizes, there is no substantive difference in the distribution of gene expression magnitude comparing H2A.B-positive vs negative tumors. FIG. 6B. Expression of genes that lie within positions 154-155 Mb of chromosome X (hg19 assembly), which include H2AFB1/2/3. Expression of H2A.B reactivated (dotted line) and silent (solid line) tumors are compared. Positions of individual genes are indicated as vertical gridlines. Shaded area represents 95% confidence interval from a LOESS fit. Apart from the specific upregulation of H2A.B in H2A.B-positive samples, there is no evidence of broad regional activation of gene expression that may explain the expression of H2A.B paralogues. FIG. 6C. As in FIG. 2B, but for the Lilljebjorn et al. 2016 (Lilljebjorn, H. et al. Identification of ETV6-RUNX1-like and DUX4-rearranged subtypes in paediatric B-cell precursor acute lymphoblastic leukaemia. Nat. Commun. 7, 11790 (2016)) B-acute lymphoblastic leukemia dataset. The reduced sequencing depth of this dataset (averaging ~23 million mapped reads per sample by TopHat) contributes to greater stochasticity in the estimation of gene expression at the low ranges, and thus while more samples exhibit expression of H2A.B paralogues (~13%), this may in part be explained by underlying stochasticity.

FIG. 8A. As in FIG. 4A, but comparing H2AFB1 (left) or H2AFB2/3 (right)-positive to negative tumors, for cancer types with at least 5 tumors each expressing either H2AFB1 or H2AFB2/3. FIG. 8B. As in FIG. 4B, but for bladder (BLCA) and endometrial (UCEC) cancers, when comparing H2AFB1 (left) or H2AFB2/3 (right)-positive to negative tumors. FIG. 8C. RNA-seq coverage plots at an alternative cassette exon event at HDLBP, comparing H2A.B-positive samples with H2A.B-negative samples from bladder cancers. FIG. 8D. As in FIG. 8C, but at MCL1. FIG. 8E. As in FIG. 8C, but in endometrial cancers at ENC1. FIG. 8F. As in FIG. 8E, but at MATR3.

FIG. 9A. cDNA panel shows that H2A.B expression is restricted to testes in normal cells, i.e., non-malignant cells. For example, as illustrated in FIG. 9A, H2A.B is not expressed in normal cells from colon, leukocytes, ovary, prostate, small intestine, spleen, and thymus. FIG. 9B. cDNA panel shows that H2A.B expression is restricted to testes in normal cells, i.e., non-malignant cells. For example, as illustrated in FIG. 9B, H2A.B is not expressed in normal cells from heart, brain, placenta, lung, liver, skeletal muscle, kidney, and pancreas.

FIG. 10A illustrates cancer cell growth experiments showing relative proliferation after 4 days of growth. Specifically, as illustrated in FIG. 10A, shRNA-induced loss of H2A.B expression causes reduced growth in the following cell lines: the SU-DHL-8 cell line (diffuse large B-cell lymphoma); the L-428 cell line (Hodgkin's lymphoma); and the SU-DHL-1 cell line (anaplastic large cell lymphoma). However, there was no effect observed in the IM-9 cell line (lymphoblastoid cell line). *denotes $<p=0.05$ by Student's two-tailed t-test. FIG. 10B illustrates RT-PCR from control or shRNA-transduced lymphoma cell lines (described in FIG. 10A) for H2A.B and actin. As a control, Western blotting for H2A and H3 shows no off-target H2A reduction.

FIG. 11A illustrates a Western blot gel depicting marker expression following a 72 hour treatment with aclarubicin, etoposide, and doxorubicin. The markers are listed on the y-axis. The specific agents and amounts were added according to the labeling on the x-axis, which is fully described in the figure legend. FIG. 11B illustrates graphs of the relative band intensity taken from the Western blot and plotted according to drug concentration. The band intensity of PARP was used as an indicator of agent cytotoxicity. The band intensity of γ-H2A.X was used as an indicator of DNA damage (side effect). The band intensity of tubulin was used as a control.

FIG. 12A illustrates a Western blot gel as described in FIG. 11A. FIG. 12B illustrates graphs of the relative band intensity taken from the Western blot as described in FIG. 11B.

FIG. 13A illustrates a Western blot gel as described in FIG. 11A. FIG. 13B illustrates graphs of the relative band intensity taken from the Western blot as described in FIG. 11B.

DETAILED DESCRIPTION

Figure 1A:
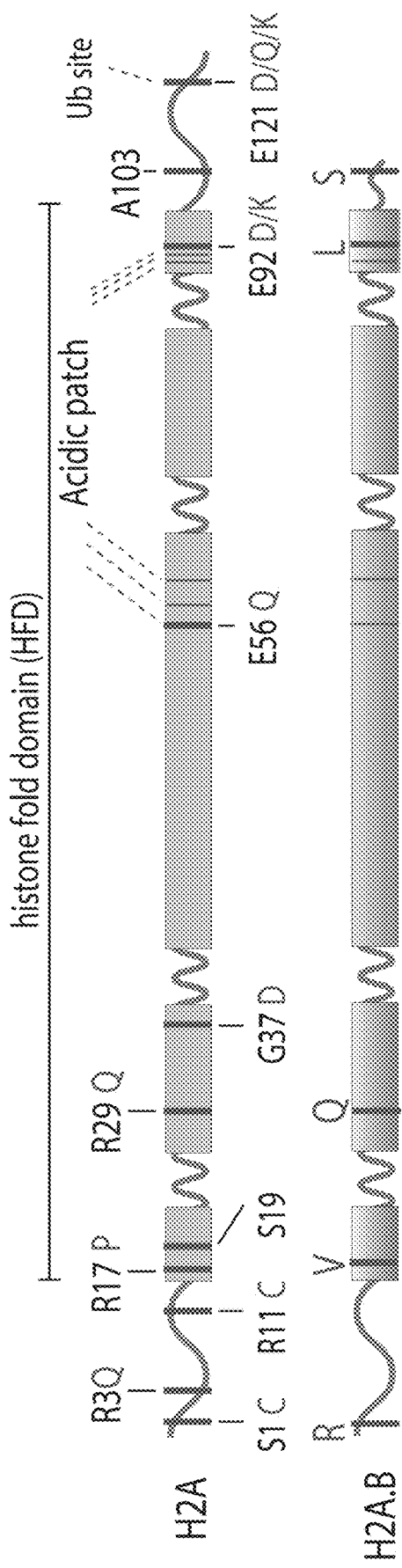

Short H2A (sH2A) histone variants are primarily expressed in the testes of placental mammals. Their incorporation into chromatin is associated with nucleosome destabilization and modulation of alternate splicing. As described in more detail in Example 1, sH2As innately possess features similar to recurrent oncohistone mutations associated with nucleosome instability. Through analyses of existing cancer genomics datasets, aberrant sH2A upregulation is found in a broad array of cancers, which manifest splicing patterns consistent with global nucleosome destabilization. The inventors posit that short H2As are a novel class of "readymade" oncohistones, whose inappropriate expression contributes to chromatin dysfunction in cancer.

In accordance with the foregoing, in one aspect the disclosure provides for a method for treating a subject with lymphoma. As used herein, the term "lymphoma" refers to a cancer of the lymphatic system. Specifically, lymphoma can be a malignant growth of B or T cells in the lymphatic system. In some embodiments, the disclosed methods can be used to treat any of the large number of lymphomas. For example, specific embodiments of lymphoma include but are not limited to Hodgkin's lymphoma, non-Hodgkin's lymphoma, diffuse large B-cell lymphoma (DLBCL), anaplastic large cell lymphoma (ALCL), and the like.

In preferred embodiments, the disclosed methods can be used to treat Hodgkin's lymphoma. In some embodiments, the Hodgkin's lymphoma is advanced Hodgkin's lymphoma. In some embodiments, the Hodgkin's lymphoma is metastatic Hodgkin's lymphoma. In some embodiments, the Hodgkin's lymphoma is MSI-H Hodgkin's lymphoma. In other embodiments, the Hodgkin's lymphoma is MSS Hodgkin's lymphoma. In still other embodiments, the Hodgkin's lymphoma is POLE-mutant Hodgkin's lymphoma. In some embodiments, the Hodgkin's lymphoma is POLD-mutant Hodgkin's lymphoma. In some embodiments, the Hodgkin's lymphoma is associated with homologous recombination repair deficiency/homologous repair deficiency (HRD).

In still other embodiments, the disclosed methods can be used for adult or childhood forms of lymphoma. In some embodiments, the disclosed methods can be used to treat lymphoma at any stage, e.g., stage I, II, III, or IV. The various types of lymphomas that can be treated with the disclosed methods are well known to those of skill in the art.

In some embodiments, the method can comprise collecting a sample from a subject having or suspected of having lymphoma; detecting a short histone H2A variant (sH2A) expression level in the sample collected from the subject; and administering to the subject a therapeutically effective dose of an anthracycline agent, if the subject has sH2A variant expression level that is detectable.

In some embodiments, the sH2A variant can be the H2A.B variant. In some embodiments, the H2A.B variant has amino acid sequence represented by SEQ ID NO:3. In some embodiments, the H2A.B variant has amino acid sequence represented by SEQ ID NO:4. In still other embodiments, the H2A.B variant is a protein encoded by histone H2A-Barr body-deficient type 1 (H2AFB1) (SEQ ID NO: 25). In some embodiments, the H2A.B variant is a protein encoded by histone H2A-Barr body-deficient type 2 (H2AFB2) (SEQ ID NO:26). In still other embodiments, the H2A.B variant is a protein encoded by histone H2A-Barr body-deficient type 3 (H2AFB3) (SEQ ID NO:27).

As used herein, the meaning of the terms "having" or "suspected of having" lymphoma is consistent with their ordinary usage as understood by one of ordinary skill in the art. For example, having lymphoma can mean but is not limited to one who is or has been diagnosed with a type of lymphoma. One who is suspected of having lymphoma can mean but is not limited to one who has symptoms of a type of lymphoma but has not been diagnosed.

In some embodiments, the sample can comprise blood, serum, plasma, or components thereof. In some embodiments, the blood sample can comprise a whole blood sample, or a blood fraction sample. In still other embodiments, the sample can comprise a tissue sample removed at surgery or by biopsy.

As used herein, detecting a short histone H2A variant (sH2A) expression level refers to identifying whether a sample collected from a subject has any level of expression of a sH2A variant, such as, for example, the H2A.B variant. As described in FIG. 9, H2A.B expression is limited to testis in normal cells, i.e., H2A.B is not expressed outside testis in non-malignant cells. In some embodiments, detecting an H2A.B expression level can comprise detecting any increase in H2A.B expression as determined by standard assays well known to one of ordinary skill in the art that can be used for quantifying histone expression. For example, it is well known that histone variants have been studied, both in vivo and in vitro, using a variety of techniques such as knockdown studies of the gene encoding a particular variant, differential gene expression and splice event analysis, chromatin immunoprecipitation, stable isotope labeling of amino acids, quantitative mass spectrometry proteomics, immunohistochemistry, Western Blotting, RT-PCR, and Enzyme-Linked ImmunoSorbant Assay (ELISA).

As used herein, the phrase "sH2A variant expression level that is detectable," refers to quantifying any amount of sH2A expression, such as the H2A.B variant, from a sample taken from a subject. The threshold for detection would depend on the method used to assay sH2A expression. For example, in some embodiments differential gene expression and splice event analysis can be used to detect H2A.B expression, wherein a threshold of >1.5 transcript per million (TPM) can be used to determine whether H2A.B can be expressed in a sample. In some embodiments, a threshold of <0.5 TPM can be used to determine whether H2A.B is not expressed in a sample. In still other embodiments, samples comprising a threshold between >0.5 TPM but <1.5 TPM would not be used in the analysis. For example, in still other embodiments, RT-PCR can be used to detect H2A.B expression, wherein a positive staining intensity can be used to determine that the sample expresses the H2A.B variant. In some embodiments, a negative staining intensity can be used to determine that the sample does not express the H2A.B variant. As used here, "positive" and "negative" staining intensity refer to the band intensity from, for example RT-PCR. Band intensity is determined by methods and standards well known to one of ordinary skill in the art.

One of ordinary skill in the art is well suited to identify the best method for detecting sH2A variant, e.g., H2A.B, expression in a sample taken from a subject. Additionally, based on the detection method used, one of ordinary skill in the art is well suited to identify the threshold for detection that would indicate that the H2A.B variant is expressed in a sample taken from a subject.

In some embodiments, if the subject has a detectable sH2A, e.g., H2A.B, expression level, as determined by one of ordinary skill in the art following any well-known method for assaying histone expression, that subject would be administered a therapeutically effective dose of an anthracycline agent. In some embodiments, if the subject has no detectable sH2A, e.g., H2A.B, expression level, as determined by one of ordinary skill in the art following any well-known method for assaying histone expression, that subject would not be administered a therapeutically effective dose of an anthracycline agent.

In some embodiments, the cytotoxic agent is an anthracycline agent. Anthracyclines are a class of drugs commonly used in cancer chemotherapy, which are also antibiotics. Structurally, all anthracyclines share a tetracyclic 7, 8, 9, 10-tetrahydrotetracene-5, 12-quinone structure and usually require glycosylation at specific sites. In some embodiments, anthracyclines refer to a class of compounds that share a tetracyclic 7, 8, 9, 10-tetrahydrotetracene-5, 12-quinone structure, including analogs and derivatives, pharmaceutically acceptable salts, hydrates, esters, conjugates, and prodrugs thereof.

Anthracyclines preferably undergo one or more of the following mechanisms of action: 1. inhibition of DNA and RNA synthesis by insertion between base pairs of the DNA/RNA strand, thereby preventing replication of rapidly growing cancer cells; 2. inhibition of topoisomerase II, preventing supercoiled DNA relaxation and thereby blocking DNA transcription and replication; 3. free oxygen radicals are generated which damage DNA and cell membranes mediated by iron; and 4. promote histone eviction, which is associated with attenuated DNA repair. In some embodiments, histone eviction deregulates the transcriptome in cancer cells and organs such as the heart and can drive apoptosis of topoisomerase-negative acute myeloid leukemia blasts in patients.

In some embodiments, examples of anthracyclines and anthracycline analogs include, but are not limited to, daunorubicin (daunorubicin), doxorubicin (adriamycin), epirubicin, idarubicin, daunorubicin, pyrarubicin (pyrarubicin), valrubicin, N-trifluoro-acetyl doxorubicin-14-valerate, aclarubicin, morpholino doxorubicin (morpholino-DOX), cyanomorpholino doxorubicin (cyanomorpholino-DOX), 2-pyrroline doxorubicin (2-PDOX), 5-iminodaunorubicin, mitoxantrone, aclarubicin A (aclarubicin), and the like.

In some embodiments, a therapeutically effective dose of an anthracycline agent can be any dose, as determined by one of ordinary skill in the art, that can be cytotoxic to the cancer cell. In some embodiments, the anthracycline agent can be administered as a single dose. In some embodiments, a single dose of an anthracycline agent can include but is not limited to between 40 to 75 mg/m$^2$ given every 21 days. In some embodiments, one of ordinary skill in the art can determine the dose of an anthracycline agent that can provide for a specific plasma concentration. In some embodiments, a single dose can be administered that can provide for a specific concentration of at least 100 nM. In some embodiments, a single dose can be administered that can provide for a specific concentration of at least 500 nM. In some embodiments, a single dose can be administered that can provide for a specific concentration of at least 1 µM. In still other embodiments, a single dose can be administered that can provide for a specific concentration of at least 5 µM.

In some embodiments, the anthracycline agent can be administered as multiple divided doses based on a particular dosing schedule. One of ordinary skill in the art can determine the proper dosing schedule and adjust the dosing schedule to achieve the desired effect. In some embodiments, the dosing schedule can include but is not limited to 25 mg/m$^2$ administered every other week for 12 weeks. In some embodiments, the dosing schedule can include but is not limited to 25 mg/m$^2$ administered on day 1 and day 15 repeated every 28 days as needed.

In some embodiments, the anthracycline agent can be administered according to any route of administration as determined by one of ordinary skill in the art. In some embodiments, the route of administration can include but is not limited to injectable, intravenous, intraarterial, intravesical, and the like.

In another aspect, the disclosure provides for a method of inducing cytotoxicity in a lymphoma cell expressing a short histone H2A (sH2A) variant. In some embodiments, the method can comprise administering to a subject in need thereof a pharmaceutical composition comprising a therapeutically effective dose of an anthracycline agent.

As used herein, "cytotoxicity" refers to the toxicity cased due to the action of an anthracycline agent on a lymphoma cell.

In another aspect, the disclosure provides for a method to inhibit cancer cell proliferation. In some embodiments, the method can comprise, collecting a sample from a subject having or suspected of having lymphoma; detecting a short histone H2A variant (sH2A) expression level in the sample collected from the subject; and administering to the subject a therapeutically effective dose of an anthracycline agent, if the subject has sH2A variant expression level that is detectable.

As used herein, cancer cell proliferation refers to how quickly a cancer cell copies its DNA and divides into 2 cells. The faster a cancer cells divides, the faster the cancer cell is growing. Standards methods well-known to one of ordinary skill in the art can be used to assess cancer cell growth.

Additional Definitions

Unless specifically defined herein, all terms used herein have the same meaning as they would to one skilled in the art of the present invention. Practitioners are particularly directed to Sambrook J., et al. (eds.), *Molecular Cloning: A Laboratory Manual*, 3rd ed., Cold Spring Harbor Press, Plainsview, N.Y. (2001); Ausubel, F. M., et al. (eds.), *Current Protocols in Molecular Biology*, John Wiley & Sons, New York (2010); Ran, F. A., et al., Genome engineering using the CRISPR-Cas9 system, *Nature Protocols*, 8:2281-2308 (2013), and Jiang, F. and Doudna, J. A., CRISPR-Cas9 Structures and Mechanisms, *Annual Review of Biophysics*, 46:505-529 (2017) for definitions and terms of art.

The use of the term "or" in the claims is used to mean "and/or" unless explicitly indicated to refer to alternatives only or the alternatives are mutually exclusive, although the disclosure supports a definition that refers to only alternatives and "and/or."

Following long-standing patent law, the words "a" and "an," when used in conjunction with the word "comprising" in the claims or specification, denotes one or more, unless specifically noted.

Unless the context clearly requires otherwise, throughout the description and the claims, the words "comprise," "comprising," and the like, are to be construed in an inclusive sense as opposed to an exclusive or exhaustive sense; that is to indicate, in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application. The word "about" indicates a number within range of minor variation above or below the stated reference number. For example, "about" can refer to a number within a range of 10%, 9%, 8%, 7%, 6%, 5%, 4%, 3%, 2%, or 1% above or below the indicated reference number.

The terms "subject," "individual," and "patient" are used interchangeably herein to refer to a mammal being assessed for treatment and/or being treated. In certain embodiments, the mammal is a human. The terms "subject," "individual," and "patient" encompass, without limitation, individuals having cancer. While subjects may be human, the term also encompasses other mammals, particularly those mammals useful as laboratory models for human disease, e.g., mouse, rat, dog, non-human primate, and the like.

The term "treating" and grammatical variants thereof may refer to any indicia of success in the treatment or amelioration or prevention of a disease or condition (e.g., a cancer, infectious disease, or autoimmune disease), including any objective or subjective parameter such as abatement; remission; diminishing of symptoms or making the disease condition more tolerable to the patient; slowing in the rate of degeneration or decline; or making the final point of degeneration less debilitating.

The treatment or amelioration of symptoms can be based on objective or subjective parameters; including the results of an examination by a physician. Accordingly, the term "treating" includes the administration of the compounds or agents of the present disclosure to prevent or delay, to alleviate, to improve clinical outcomes, to decrease occurrence of symptoms, to improve quality of life, to lengthen disease-free status, to stabilize, to prolong survival, to arrest or inhibit development of the symptoms or conditions associated with a disease or condition (e.g., a cancer), or any combination thereof. The term "therapeutic effect" refers to the reduction, elimination, or prevention of the disease or condition, symptoms of the disease or condition, or side effects of the disease or condition in the subject.

Reference to sequence identity addresses the degree of similarity of two polymeric sequences, such as nucleic acid or protein sequences. Determination of sequence identity can be readily accomplished by persons of ordinary skill in the art using accepted algorithms and/or techniques. Sequence identity is typically determined by comparing two optimally aligned sequences over a comparison window, where the portion of the peptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. Various software driven algorithms are readily available, such as BLAST N or BLAST P to perform such comparisons.

Publications cited herein and the subject matter for which they are cited are hereby specifically incorporated by reference in their entireties. The publication by Chew et al., entitled "Short H2A histone variants are expressed in cancer," *Nature Communications,* 2021 Jan. 20; 12(1):490 and all of its figures, supplementary figures, supplementary tables, and supplementary data 1-7 are herein incorporated by reference.

EXAMPLES

The following examples are set forth so as to provide those of ordinary skill in the art with a complete disclosure and description of how to make and use the present invention, and are not intended to limit the scope of what the inventors regard as their invention nor are they intended to represent that the experiments below are all or the only experiments performed.

Example 1

This Example describes that short H2A histone variants are expressed in cancer. Specifically, in this Example, specific embodiments are provided that describe aberrant sH2A upregulations were observed in a broad array of cancers, which manifest splicing patterns consistent with global nucleosome destabilization.

Results sH2As have Evolved Oncohistone Features

Figure 5A:
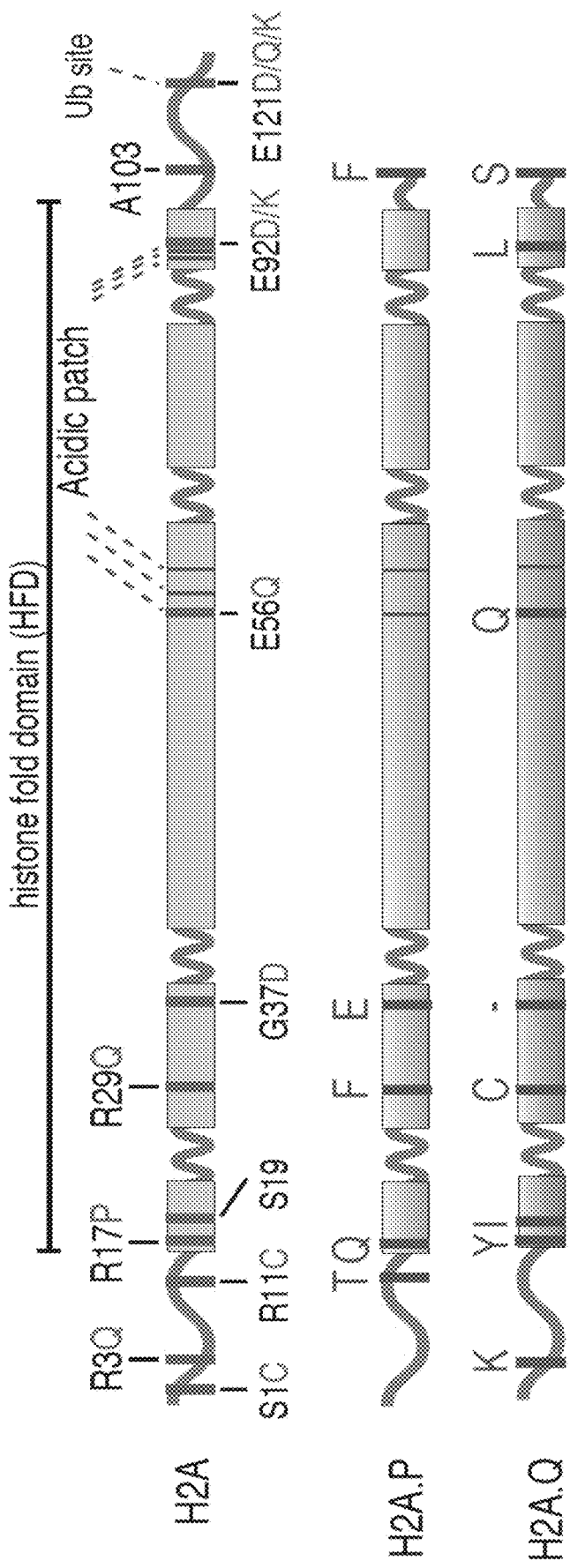
FIGS. 5A to 5C. Other short H2A variants possess oncohistone features that are conserved throughout primates.
Figure 5B:
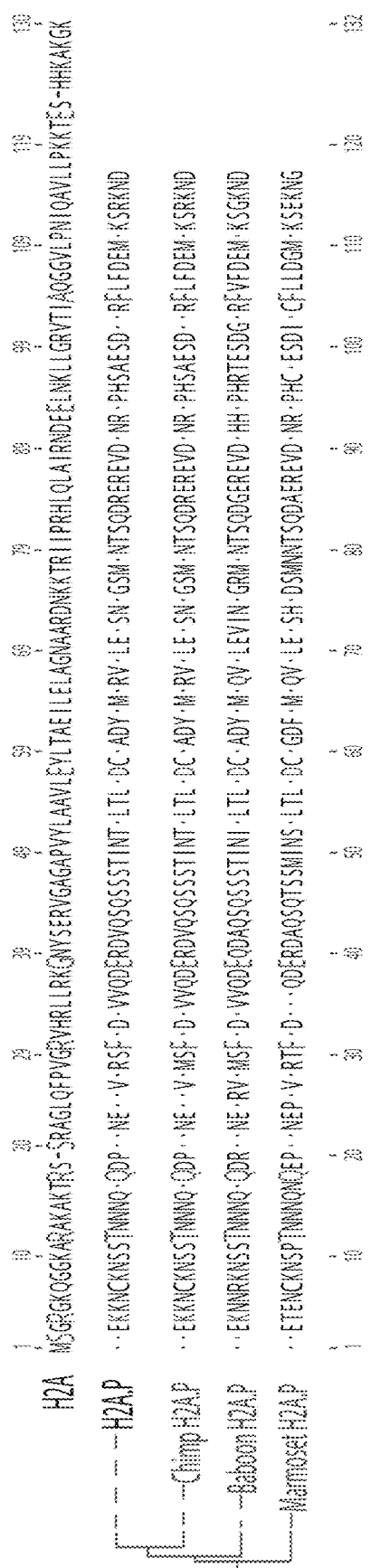
Figure 5C:
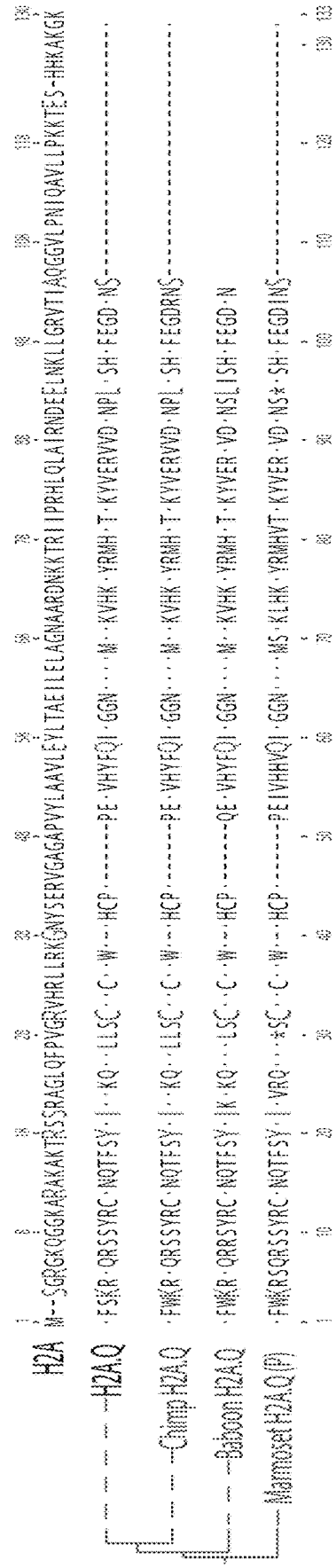

There are five X-linked sH2A genes in humans: H2A.B.1.1 (H2AFB2), H2A.B.1.2 (H2AFB3), H2A.B.2 (H2AFB1), H2A.P (HYPM) and H2A.Q (unannotated) (Molaro, A., Young, J. M. & Malik, H. S. Evolutionary origins and diversification of testis-specific short histone H2A variants in mammals. *Genome Res* 28, 460-473 (2018)). The amino acid sequences of sH2As were compared to canonical H2A to assess whether their rapid evolution resulted in oncohistone-like changes. This analysis revealed that many of the most common cancer-associated mutations in canonical H2A are already present in all wildtype sH2A sequences (FIGS. 1A, 5A, and 5B). This includes R29Q/F substitutions that correspond to the second most frequent mutation in canonical H2A (FIGS. 1A, 5A, and 5B) (Bennett, R. L. et al. A Mutation in Histone H2B Represents a New Class of Oncogenic Driver. *Cancer Discov* (2019); Nacev, B. A. et al. The expanding landscape of 'oncohistone' mutations in human cancers. *Nature* 567, 473-478 (2019)). In addition, all wildtype sH2As have a C-terminal truncation that removes E121, the most common mutation in canonical H2A (FIGS. 1A, 5A, 5B) (Bennett, R. L. et al. A Mutation in Histone H2B Represents a New Class of Oncogenic Driver. *Cancer Discov* (2019); Nacev, B. A. et al. The expanding landscape of 'oncohistone' mutations in human cancers. *Nature* 567, 473-478 (2019)). Phylogenetic analyses in primates showed that despite their rapid evolution, these oncohistone-like changes are highly conserved (FIGS. 1B and 5A-5C) (Molaro, A., Young, J. M. & Malik, H. S. Evolutionary origins and diversification of testis-specific short histone H2A variants in mammals. *Genome Res* 28, 460-473 (2018)). This conservation implies functional consequences as many of these residues are critical contact points for histone-DNA or histone-histone interactions (Luger, K., Mader, A. W., Richmond, R. K., Sargent, D. F. & Richmond, T. J. Crystal structure of the nucleosome core particle at 2.8 A resolution. *Nature* 389, 251-60 (1997); Kohestani, H. & Wereszczynski, J. Effects of H2A.B incorporation on nucleosome structures and dynamics. *bioRxiv,* 2020.06.25.172130 (2020); Peng, J., Yuan, C., Hua, X. & Zhang, Z. Molecular mechanism of histone variant H2A.B on stability and assembly of nucleosome and chromatin structures. *Epigenetics Chromatin* 13, 28 (2020); Bao, Y. et al. Nucleosomes containing the histone variant H2A.Bbd organize only 118 base pairs of DNA. *EMBO J* 23, 3314-24 (2004); Doyen, C. M. et al. Dissection of the unusual structural and functional properties of the variant H2A.Bbd nucleosome. *EMBO J* 25, 4234-44 (2006)). These data show that sH2As contain oncohistone features similar to canonical H2A mutations in cancers.

H2A.Bs are Reactivated in a Broad Array of Cancers

The oncohistone properties inherent in sH2As indicate that they may play a role in cancer simply through upregulation. The inventors focused on expression of H2A.B paralogs, since they are well annotated and have been shown to impact both nucleosome stability and cell cycle progression (Sansoni, V. et al. The histone variant H2A.Bbd is enriched at sites of DNA synthesis. *Nucleic Acids Res* 42, 6405-20 (2014)). To investigate whether H2A.Bs are reactivated in different cancers, transcriptomic data was first used from The Cancer Genome Atlas (TCGA). This analysis showed that H2A.B paralogs are activated (at a threshold of >1.5 transcripts per million (TPM)) in numerous individual tumors across cancer types (FIG. 2A and Supplementary Data 1 and 2), but never in adjacent normal tissue (Supplementary Data 1), and very rarely (<1.5%) in non-testes tissue samples from the Genotype-Tissue Expression database (GTEx) (Table 1).

TABLE 1

Expression of H2AFB1/2/3 in GTEx normal tissue

| GTEx Tissue | Number with H2AFB1/2/3 reactivated | Total Number | Percentage Reactivated |
|---|---|---|---|
| Other | 0 | 7900 | 0.00 |
| Brain | 4 | 2541 | 0.16 |
| Colon | 1 | 571 | 0.18 |
| Thyroid | 1 | 508 | 0.2 |
| Blood vessel | 3 | 1320 | 0.23 |
| Esophagus | 6 | 1364 | 0.44 |
| Prostate | 1 | 160 | 0.63 |
| Uterus | 1 | 128 | 0.78 |
| Spleen | 3 | 202 | 1.49 |
| Blood | 14 | 929 | 1.51 |
| Testis | 152 | 252 | 60.32 |

Table 1 lists numbers and percentages of samples with H2AFB1, H2AFB2, or H2AFB3 reactivation (expression >1.5 TPM) from the GTEx dataset of normal tissues, by various tissue types.

The range of expression varies widely, with H2A.B-encoding transcripts present at >100 TPMs in two specimens (Supplementary Data 2). Although many tumors reactivate H2AFB1 alone, most tumors that express H2AFB2 also express H2AFB3 (FIG. 2A). This finding may result from transcriptional co-regulation due to their genomic proximity (FIG. 6B) or inability to distinguish these near-identical paralogs by short read mapping (Molaro, A., Young, J. M. & Malik, H. S. Evolutionary origins and diversification of testis-specific short histone H2A variants in mammals. *Genome Res* 28, 460-473 (2018)). Despite their similarity, the inventors were able to distinguish these two genes in a few tumor samples (FIG. 2A).

Across the TCGA dataset, diffuse large B-cell lymphomas (DLBCLs) showed the highest frequency of aberrant H2A.B expression at 50% (FIG. 2A). A recent analysis of DLBCL genomes identified five distinct molecular subtypes (Chapuy, B. et al. Molecular subtypes of diffuse large B cell lymphoma are associated with distinct pathogenic mechanisms and outcomes. *Nat Med* 24, 679-690 (2018)) including a favorable prognosis-germinal center (FP-GC) subtype associated with histone mutations. In some embodiments, it was determined whether H2A.B expression was restricted to the FP-GC subtype. In some embodiments, 37 DLBCL samples were queried for mutations associated with the FP-GC subtype including linker H1 and core histones, immune evasion genes, PI3K, NF-κB, and JAK/STAT/RAS pathway components (Chapuy, B. et al. Molecular subtypes of diffuse large B cell lymphoma are associated with distinct pathogenic mechanisms and outcomes. *Nat Med* 24, 679-690 (2018)). Twenty-five samples had a mutation in at least one of these genes (Supplementary Data 3), including 15 different samples with histone mutations (Supplementary Data 3). H2A.B was expressed in 13 samples with any FP-GC mutation, and in 6 of the 10 FP-GC samples without histone mutations (Supplementary Data 3). To contrast this with another DLBCL subtype, in some embodiments, H2A.B expression was analyzed in the poorer prognosis-germinal center subtype associated with mutations in chromatin modifiers EZH2, CREBBP, EP300, KMT2D and BCL11A mutations (Chapuy, B. et al. Molecular subtypes of diffuse large B cell lymphoma are associated with distinct pathogenic mechanisms and outcomes. *Nat Med* 24, 679-690 (2018)). Though the analysis did not identify any EZH2 mutations, 15 samples had mutations in at least one chromatin modifier gene. Nine of these samples also had H2A.B upregulation. These analyses indicate that H2A.B expression occurs in multiple DLBCL subtypes.

Other cancers in the TCGA dataset with H2A.B aberrant expression include uterine corpus endometrial carcinomas (UCEC) (9.5%), urothelial bladder carcinomas (BLCA) (4.7%), and cervical squamous cell carcinomas and endocervical carcinomas (CESC) (4.5%) (FIG. 2a). These same cancers were previously identified as having the highest frequencies of core histone mutations in the TCGA dataset, ranging from 5-8% (Bennett, R. L. et al. A Mutation in Histone H2B Represents a New Class of Oncogenic Driver. *Cancer Discov* (2019)). A few specimens were found with both recurrent H2A mutations and H2A.B expression (Supplementary Data 4), however, the low numbers of specimens that share both of these features hinders meaningful correlative analyses.

Figure 2C:
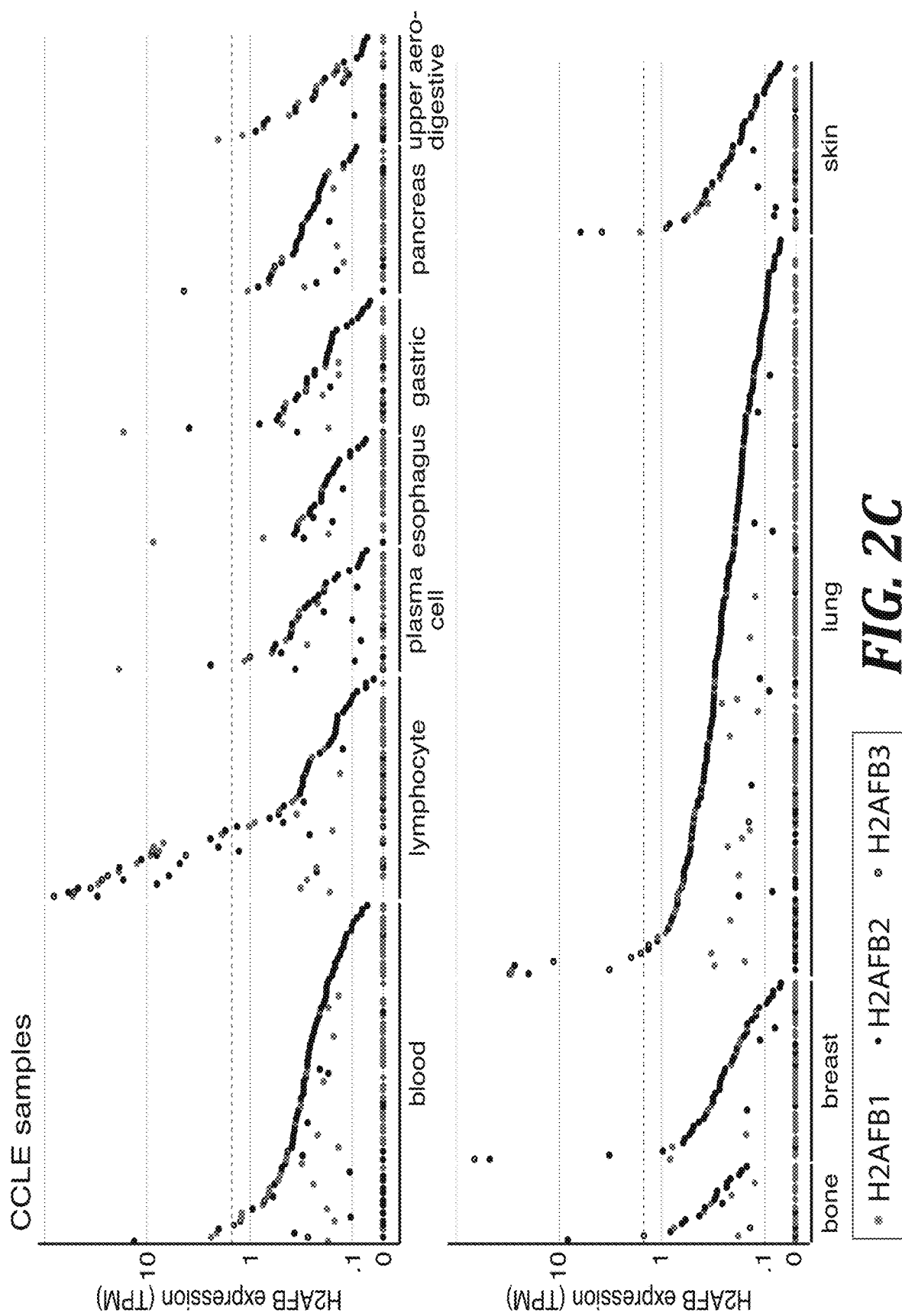

Upregulation of H2A.B in HL (Winkler, C. et al. Hodgkin's lymphoma RNA-transfected dendritic cells induce cancer/testis antigen-specific immune responses. *Cancer Immunol Immunother* 61, 1769-79 (2012)) and DLBCLs (FIG. 2A) prompted analysis of datasets from other lymphoid lineage-derived, low mutation cancers for aberrant H2A.B expression. Four separate B-acute lymphoblastic leukemia (B-ALL) datasets were queried and found 6-7% of specimens with H2A.B-encoding transcripts at >1.5 TPM (FIG. 2B) in three of the datasets (Liu, Y. F. et al. Genomic Profiling of Adult and Pediatric B-cell Acute Lymphoblastic Leukemia. *EBioMedicine* 8, 173-183 (2016); Qian, M. et al. Whole-transcriptome sequencing identifies a distinct subtype of acute lymphoblastic leukemia with predominant genomic abnormalities of EP300 and CREBBP. *Genome Res* 27, 185-195 (2017); Yasuda, T. et al. Recurrent DUX4 fusions in B cell acute lymphoblastic leukemia of adolescents and young adults. *Nat Genet* 48, 569-74 (2016)), and 13% in the fourth (Supp. FIG. 2c) (Lilljebjorn, H. et al. Identification of ETV6-RUNX1-like and DUX4-rearranged subtypes in pediatric B-cell precursor acute lymphoblastic leukemia. *Nat Commun* 7, 11790 (2016)). Because of the diversity of liquid and solid cancers with H2A.B expression, we searched the Cancer Cell Line Encyclopedia (CCLE) database (Barretina, J. et al. The Cancer Cell Line Encyclopedia enables predictive modelling of anticancer drug sensitivity. *Nature* 483, 603-7 (2012)) was searched for cell lines with H2A.B expression at >1.5 TPM. Consistent with high frequency H2A.B expression in TCGA DLBCLs, lymphomas demonstrated the highest percentage of H2A.B-positive cell lines (FIG. 2C), with 70% of Hodgkin's lymphoma and 25% of non-Hodgkin's lymphoma cell lines expressing H2A.B. The spectrum of H2A.B expression across other cancers was also similar between CCLE and TCGA datasets (FIG. 2C). From these results, it can be concluded that H2A.B is aberrantly expressed in a broad array of cancers.

Figure 6A:
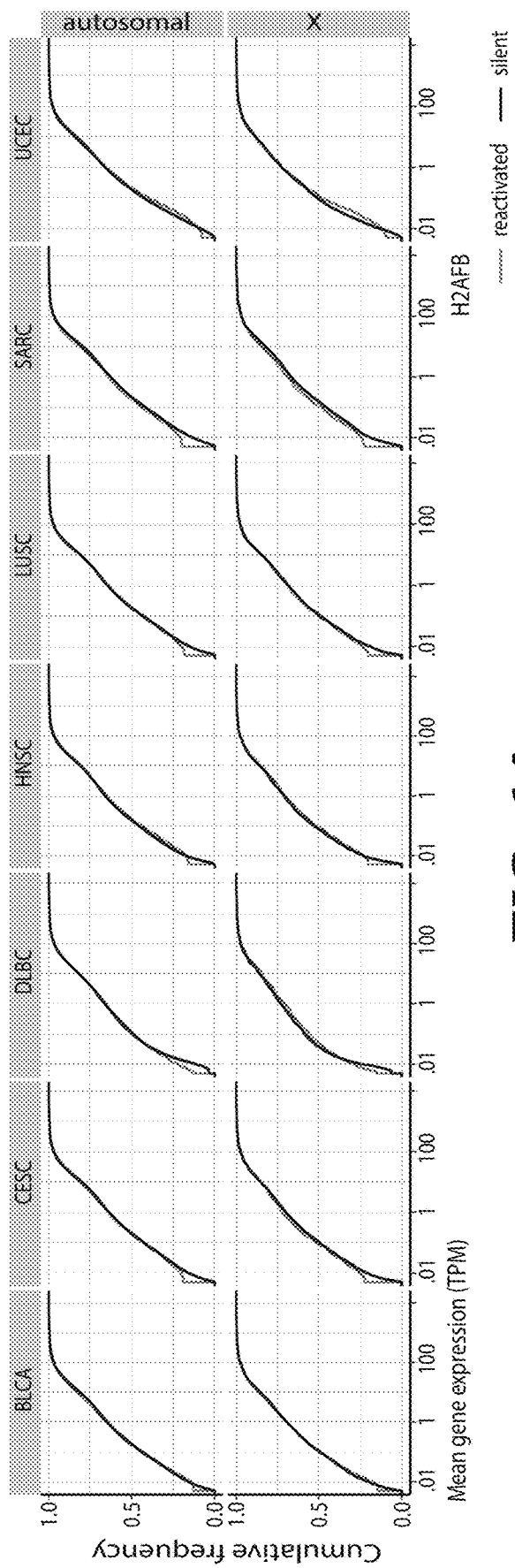
FIGS. 6A to 6C.
Figure 6B:
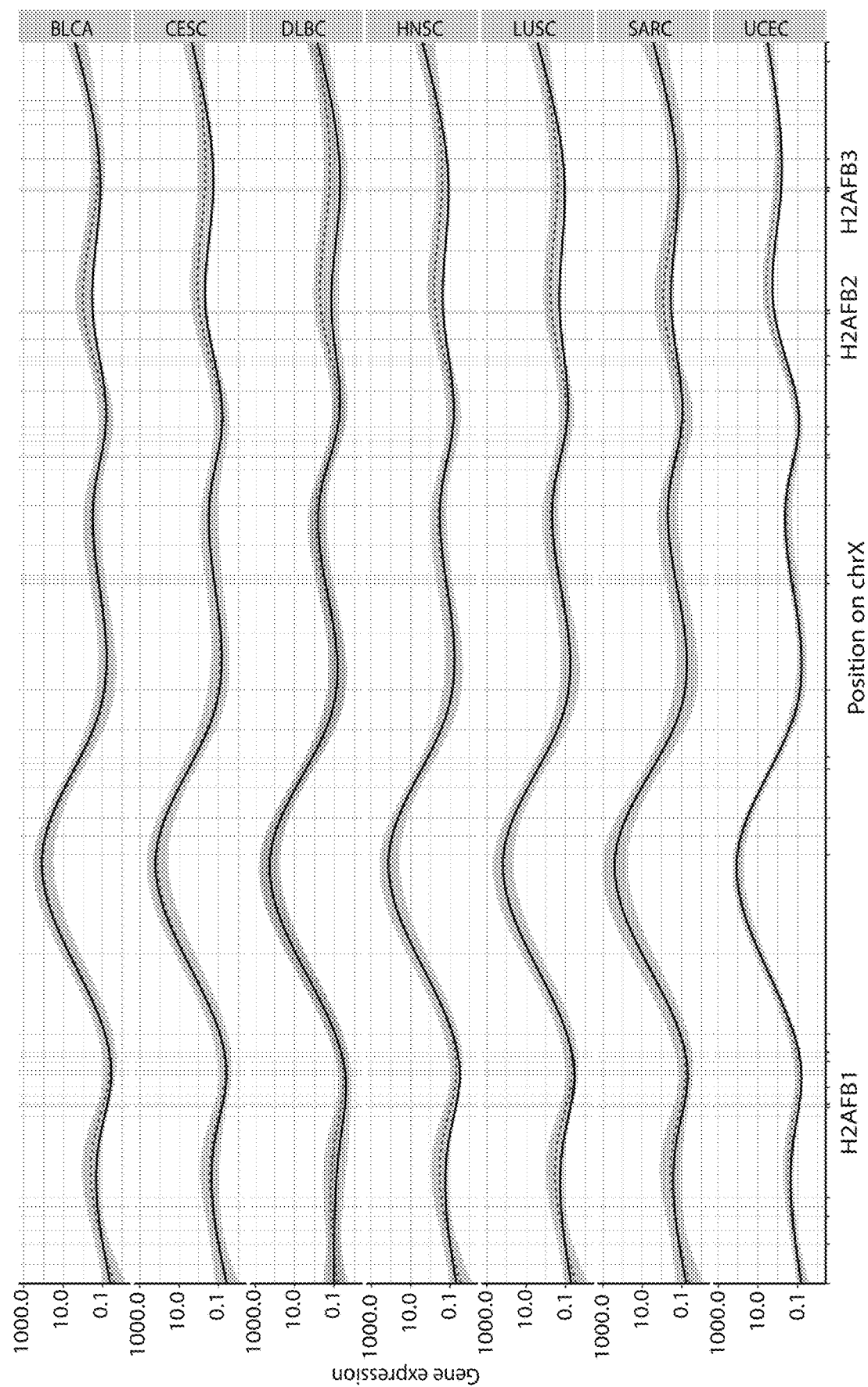
Figure 6C:
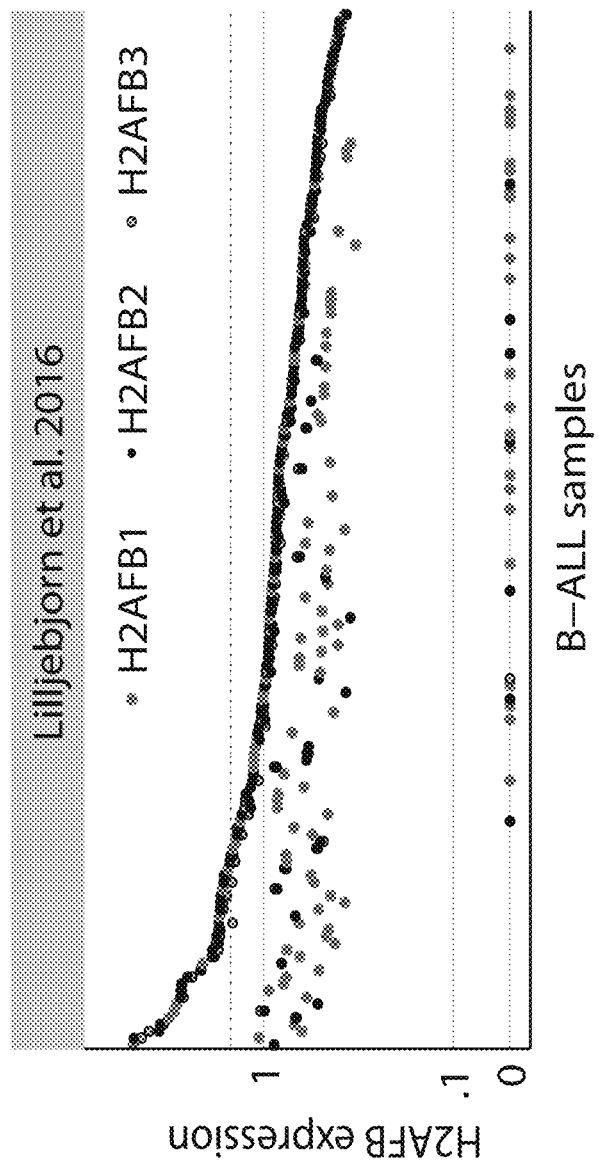

In some embodiments, the potential causes of H2A.B induction in cancer was investigated. While little is known about the transcriptional regulation of H2A.B-encoding loci in testis, changes in X-chromosome ploidy are associated with increased fitness in cancer cells (Xu, J. et al. Free-living human cells reconfigure their chromosomes in the evolution back to uni-cellularity. *Elife* 6 (2017). In some embodiments, investigation of whether H2A.B expression in cancer may result from global derepression of large domains, amplifications, or gain of an additional X chromosome in these samples. In some embodiments, levels of X—was compared to autosome-linked transcripts in H2A.B-expressing and silent samples and found no significant differences (FIG. 6A). In some embodiments, the expression profiles of individual H2AFB loci and their surrounding regions was investigated, and from this investigation, it was found that upregulation was limited to each individual H2A.B-encoding locus without upregulation of neighboring loci (FIG. 6B). These results are consistent with findings in the TCGA dataset, where median H2A.B expression for the 232 H2A.B-positive samples is approximately 3 TPM (Supplementary Data 2), corresponding to 49th percentile of all expressed genes. This level of expression is more likely the result of local, specific activation of individual H2AFB paralogues than recurrent amplifications or broader X-chromosome dysfunction.

Figure 3A:
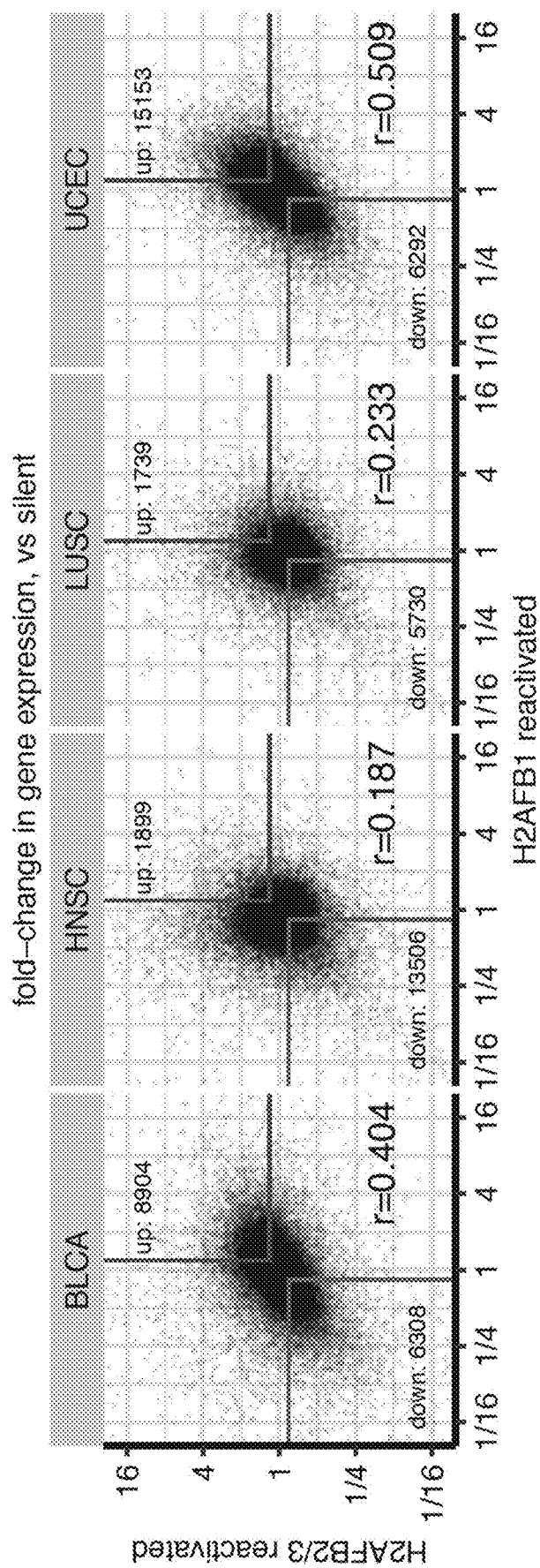
FIGS. 3A to 3C. Gene expression analyses in H2A.B-reactivated cancers.

H2A.Bs are Associated with Cancer-Specific, Rather than Pan-Cancer Gene Expression Programs H2A.B proteins encoded by H2AFB1 and H2AFB2/3 are nearly identical in sequence. Nevertheless, the independent reactivation of H2AFB1 and H2AFB2/3 in different cancer specimens raised the possibility that these closely-related paralogues may be associated with distinct global gene expression programs. To explore this, in some embodiments, transcriptomes were compared from H2AFB1-reactivated samples versus those from H2AFB2/3-reactivated samples within the same cancer types. From the comparison, it was found that thousands of genes that were commonly up- or downregulated in UCEC, HNSC, LUSC and BLCA (FIG. 3A), suggesting that different H2A.B paralogues operate in similar gene expression contexts.

Figure 3B:
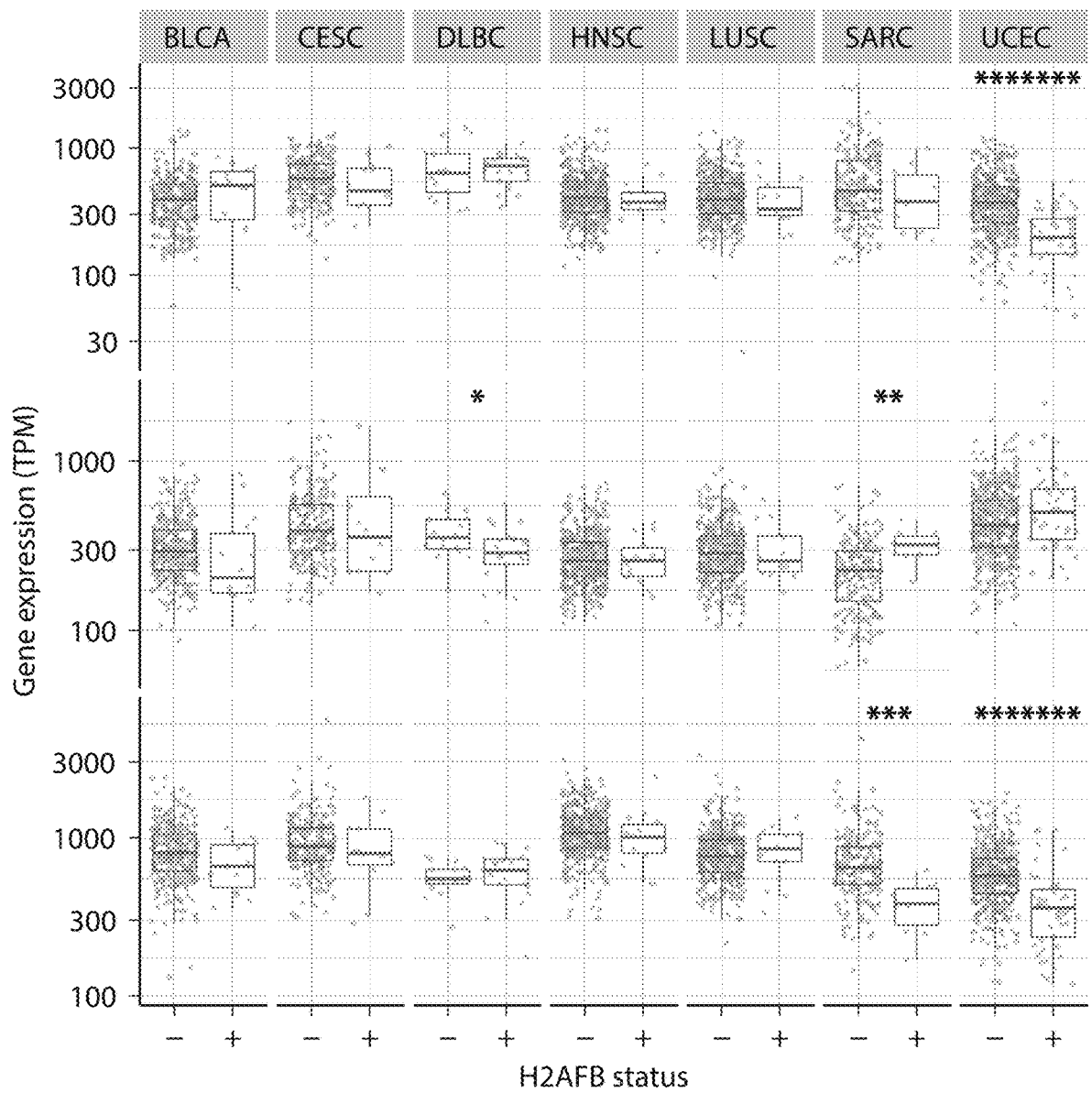
Figure 3B:
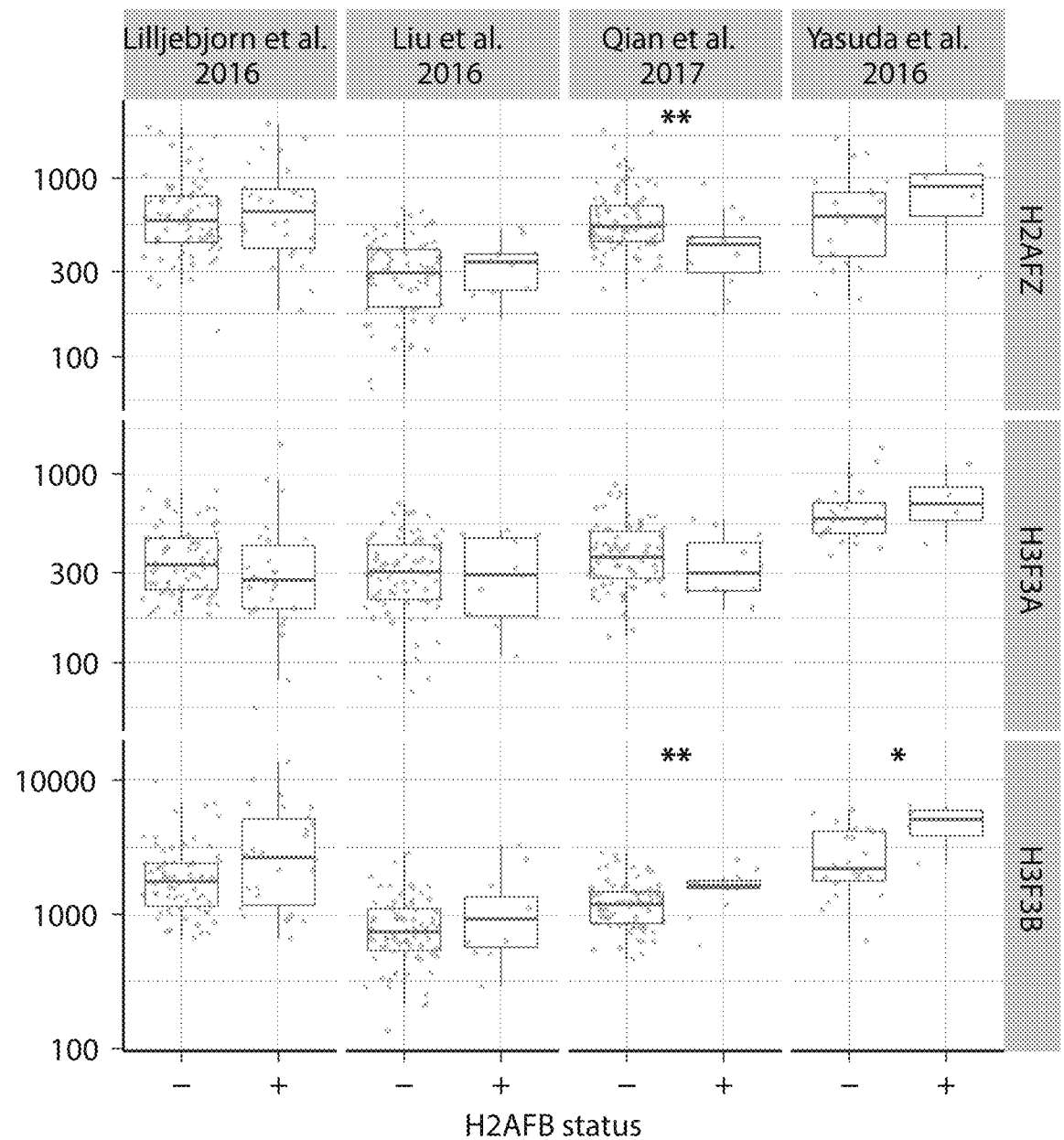

In some embodiments, it was investigated whether expression of other genes was consistently associated with H2A.B expression. In this investigation, it was found that 146 genes were upregulated and 90 downregulated across H2A.B-positive cancers (Supplementary Data 5). Further, this investigation did not identify co-upregulation of other testis-specific histone variants such as H2A.1 (TH2A) or H2B.1 (TH2B) (Hoghoughi, N., Barral, S., Vargas, A., Rousseaux, S. & Khochbin, S. Histone variants: essential actors in male genome programming. *J Biochem* 163, 97-103 (2018)) (Supplementary Data 5) in H2A.B-expressing cancers. Three histone variants with broad tissue distributions, H2A.Z, H2A.X and H3.3, also did not show consistent differences between H2A.B-positive and negative cancers, except for lower H2A.Z and H2A.X in UCEC (FIG. 3B). H2A.X levels, it should be noted, are similar to maximum values for H2A.B (FIG. 3B, Supplementary Data 1). In some embodiments, expression of the histone chaperone NAP1 was examined, which can assemble H2A.B-containing nucleosomes (Bao, Y. et al. Nucleosomes containing the histone variant H2A.Bbd organize only 118 base pairs of DNA. *EMBO J* 23, 3314-24 (2004); Martire, S., Nguyen, J., Sundaresan, A. & Banaszynski, L. A. Differential contribution of p300 and CBP to regulatory element acetylation in mESCs. *BMC Mol Cell Biol* 21, 55 (2020)). NAP1-encoding transcripts were detected in all TCGA cancers, with DLBCLs expressing the highest levels (FIG. 3B, Table 2).

TABLE 2

Number of H2AFB1/2/3 reactivated and silent samples in The Cancer Genome Atlas (TCGA) and Acute B Lymphoblastic Leukemia (B-ALL) datasets.

| Cancer Dataset | Reactivated | Silent |
|---|---|---|
| BLCA | 16 | 280 |
| CESC | 13 | 231 |
| DLBCL | 24 | 17 |
| HNSC | 16 | 442 |
| LUAD | 10 | 476 |
| LUSC | 15 | 409 |
| SARC | 10 | 199 |
| UCEC | 51 | 280 |
| Lilijebjorn* | 26 | 69 |
| Liu* | 11 | 74 |
| Qian* | 13 | 77 |
| Yasuda* | 4 | 24 |

Table 2 lists the number of cancer samples in TCGA and B-ALL datasets used for gene expression and cancer testes antigen analyses (FIG. 3A and 3B).
*Lilljebjorn, H. et al. Identification of ETV6-RUNX1-like and DUX4-rearranged subtypes in paediatric B-cell precursor acute lymphoblastic leukaemia. *Nat. Commun.* 7, 11790 (2016).
*Liu, Y. F. et al. Genomic profiling of adult and pediatric B-cell acute lymphoblastic leukemia. *EBioMedicine* 8, 173-183 (2016).
*Qian, M. et al. Whole-transcriptome sequencing identifies a distinct subtype of acute lymphoblastic leukemia with predominant genomic abnormalities of EP300 and CREBBP. *Genome Res.* 27, 185-195 (2017).
*Yasuda, T. et al. Recurrent DUX4 fusions in B cell acute lymphoblastic leukemia of adolescents and young adults. *Nat. Genet.* 48, 569-574 (2016).
BLCA (bladder cancer); CESC (cervical squamous cell carcinoma and endocervical adenocarcinoma); DLBC (diffuse large B-cell lymphoma); HNSC (head and neck squamous cell carcinoma); LUAD (lung adenocarcinoma); LUSC (lung squamous cell carcinoma); SARC (sarcoma); UCEC (uterine corpus endometrial carcinoma).

The chromatin consequences of this correlation i.e., whether higher NAP1 levels result in increased incorporation of H2A.B in chromatin are unknown.

Figure 3C:
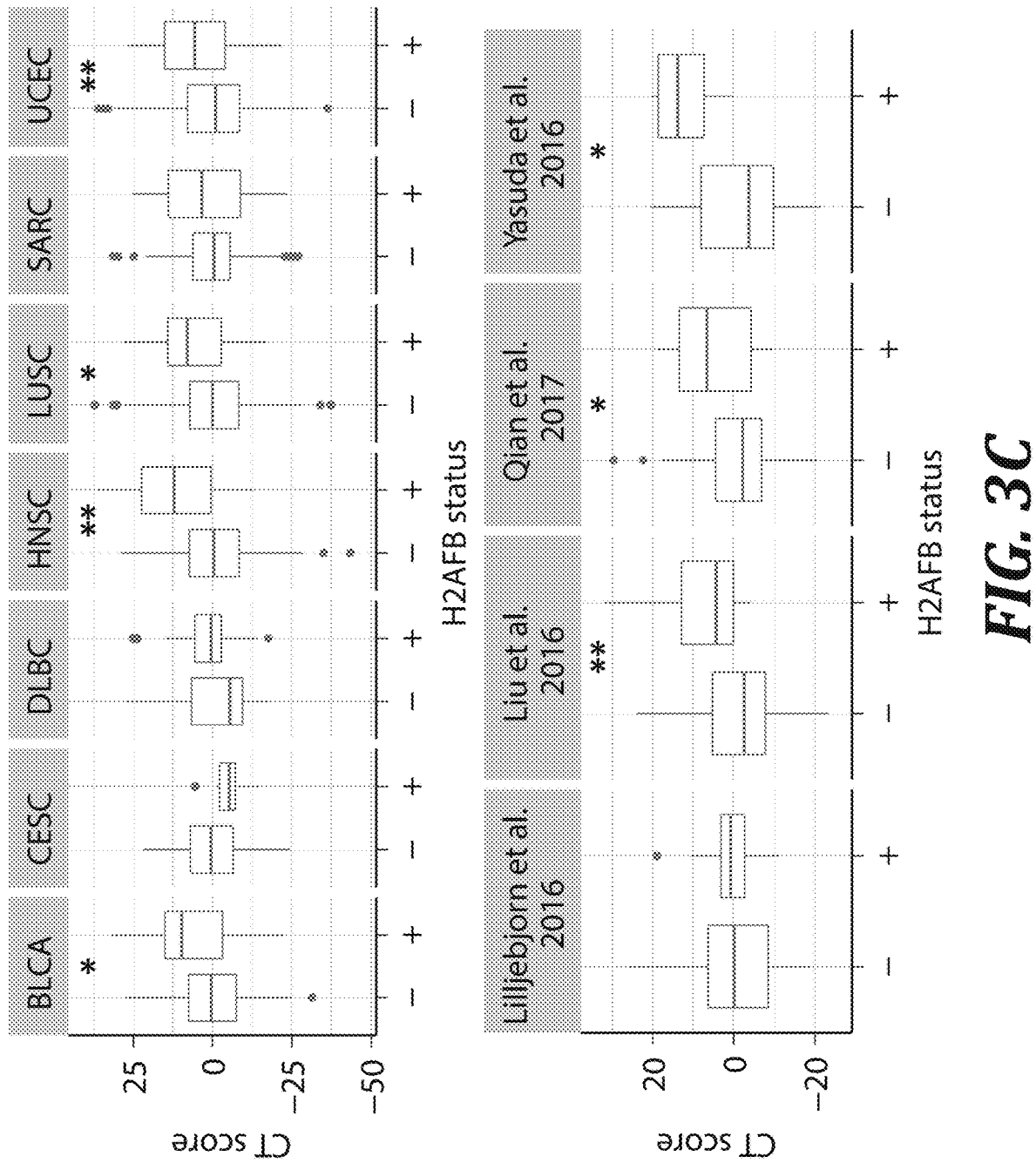

The inventors noted that 12/146 of the commonly-upregulated genes are Cancer-Testis Antigens. Since H2AFB1 was previously shown to be co-expressed with a subset of Cancer-Testis Antigens (CTAs) in HL (Winkler, C. et al. Hodgkin's lymphoma RNA-transfected dendritic cells induce cancer/testis antigen-specific immune responses. *Cancer Immunol Immunother* 61, 1769-79 (2012)), it was determined whether H2A.B-reactivated cancers are generally associated with CTA upregulation. The expression of individual CTAs was summarized into a composite "CTA score" for each tumor and compared scores between H2A.B-reactivated and silent samples (FIG. 3C). Although H2A.B-expressing HNSCs, LUSCs and UCECs showed statistically significant CTA enrichment, DLBCLs and SARCs did not (FIG. 3C). In some embodiments, the four B-ALL datasets were examined and found that H2A.B expression was associated with CTA upregulation (FIG. 3C). However, individual CTAs such as NY-ESO-1 (CTAG1B) and CT45A5 were variably expressed across cancers (Supplementary Data 5), consistent with well-recognized transcriptional heterogeneity of this class of genes (Fratta, E. et al. The biology of cancer testis antigens: putative function, regulation and therapeutic potential. *Mol Oncol* 5, 164-82 (2011); Whitehurst, A. W. Cause and consequence of cancer/testis antigen activation in cancer. *Annu Rev Pharmacol Toxicol* 54, 251-72 (2014)). These data indicate that H2A.B expression is associated with CTA expression in several cancer types.

Figure 7:
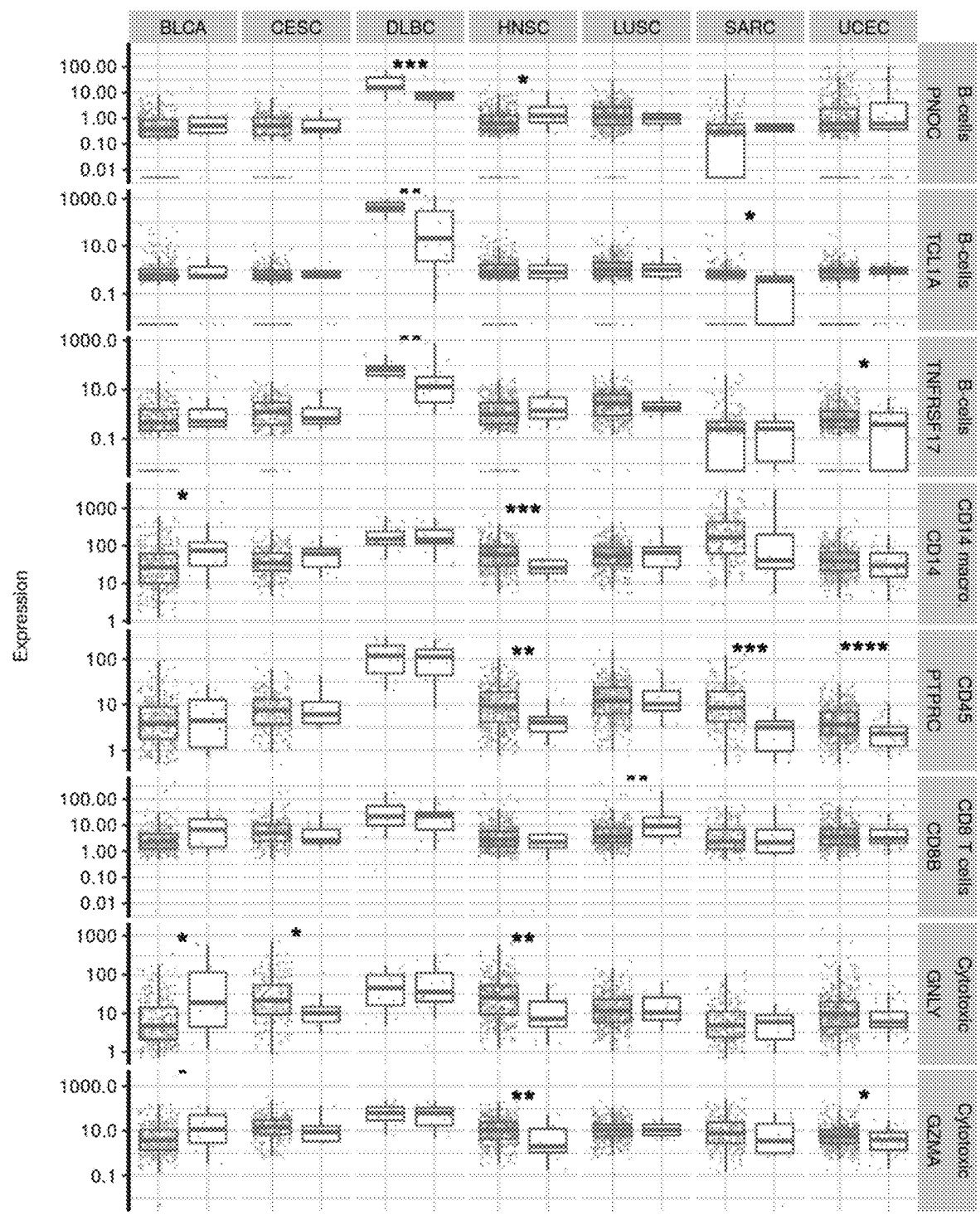
FIG. 7. Box and scatter plots of gene expression (by RNA-seq) of various immune cell markers (rows) in H2A.B positive (under each column, the boxplot of the right) and negative (under each column, the boxplot of the left) tumors in various TCGA cancers (columns). Asterisks show the statistical significance of the difference in marker gene expression by a two-sided Mann-Whitney U test—*: $p<0.05$; : $p<0.01$; *: $p<0.001$; ****: $p<0.0001$ etc. Only immune marker genes where at least one cancer type shows a statistically significant difference in gene expression (at $p<0.01$) are depicted. Boxplots indicate the 1*quartile, median and $3_{rd}$ quartile, while the whiskers extend from the box-ends to values no larger/smaller than 1.5 times of the inter-quartile range. All data points are additionally plotted.
Figure 7:
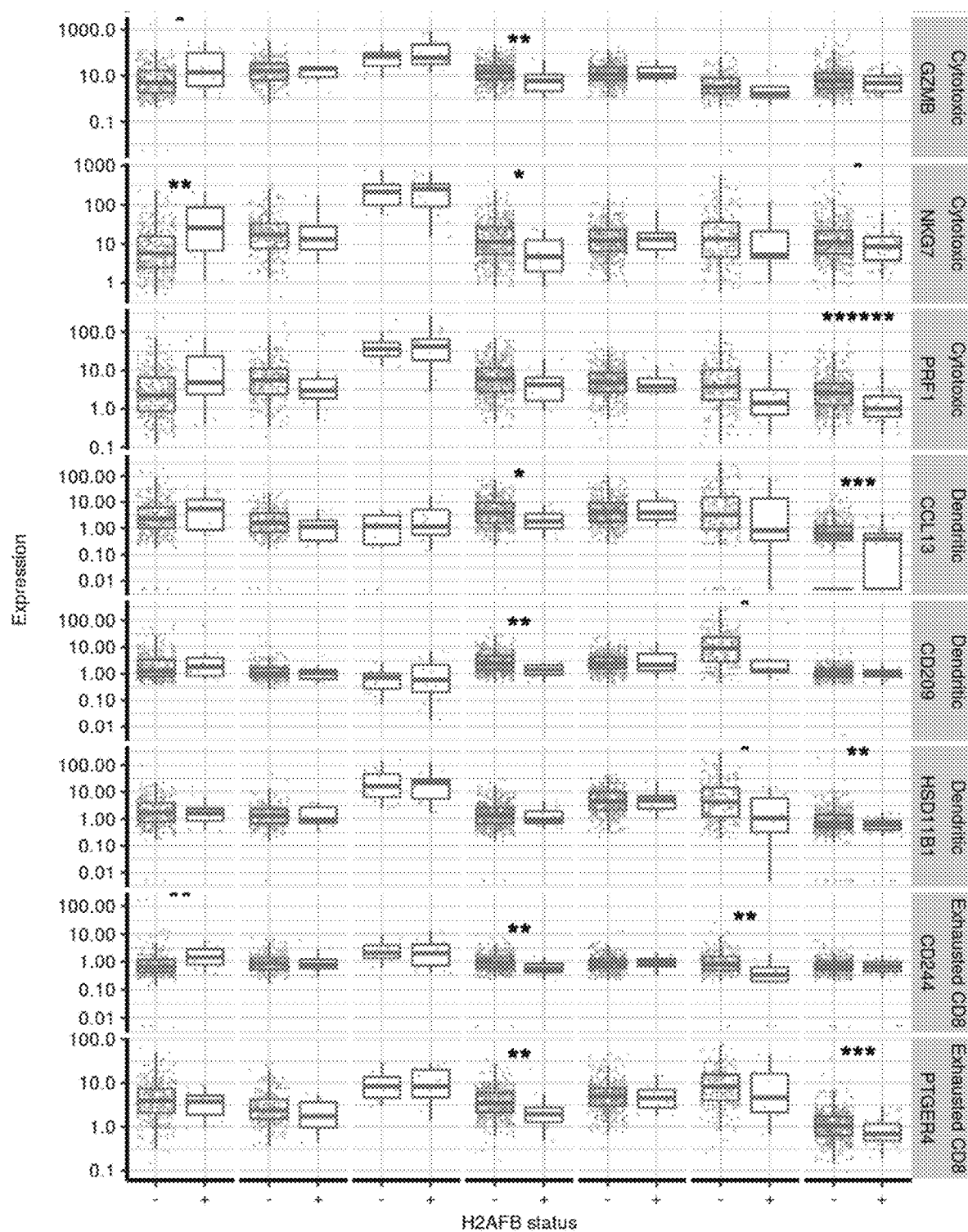
Figure 7:
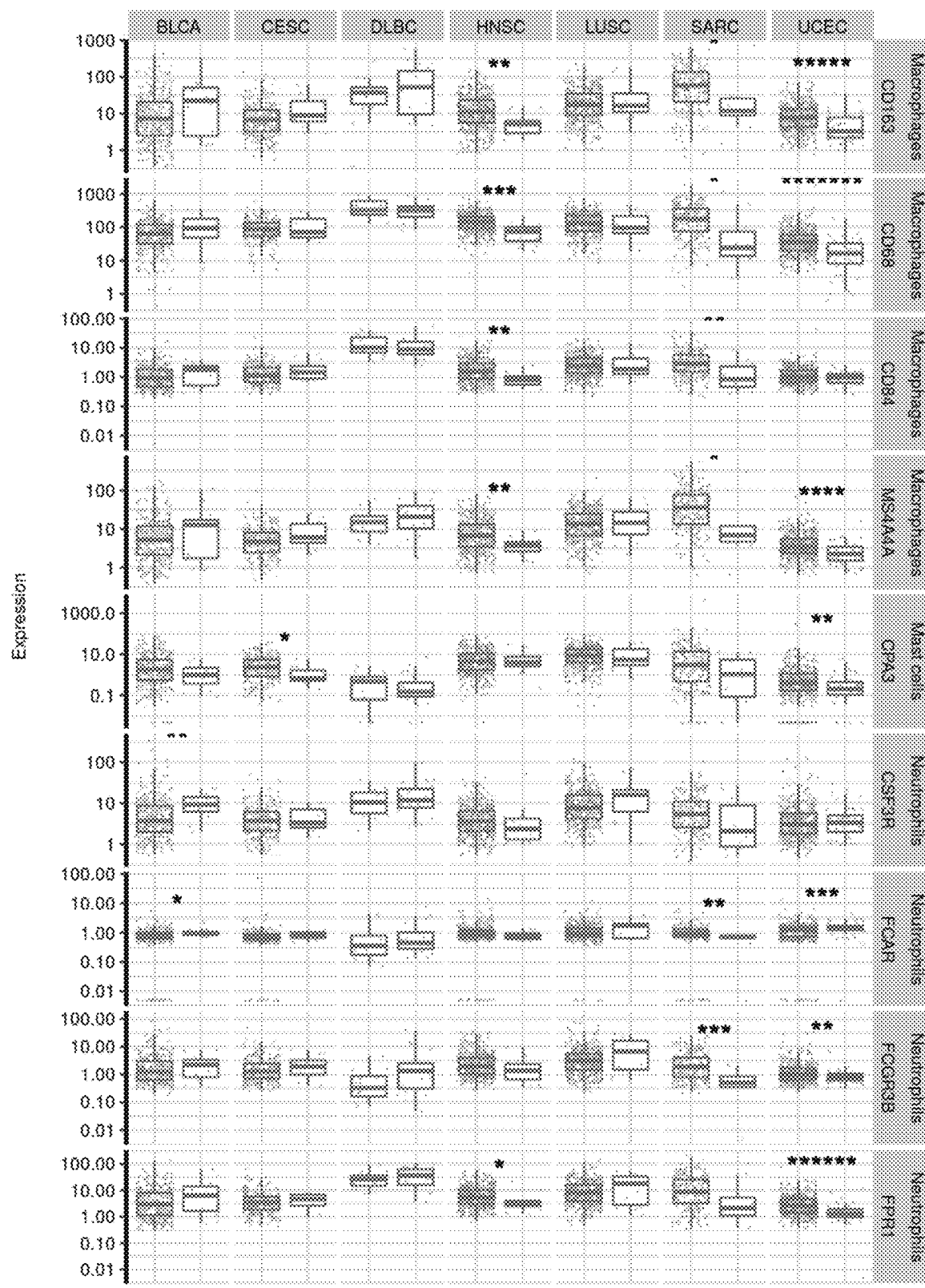
Figure 7:
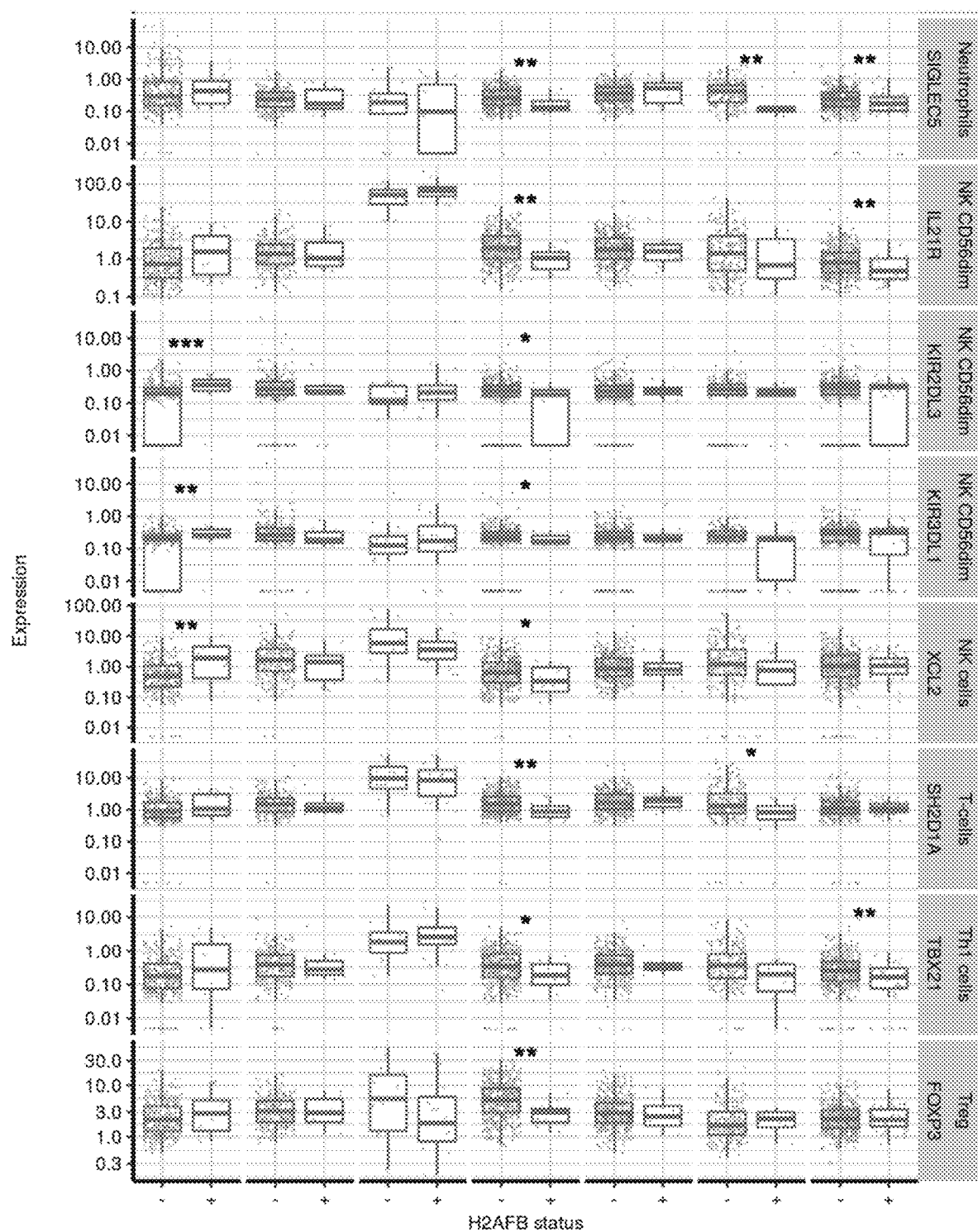

CTAs are subject to endogenous immunosurveillance mechanisms (Winkler, C. et al. Hodgkin's lymphoma RNA-transfected dendritic cells induce cancer/testis antigen-specific immune responses. *Cancer Immunol Immunother* 61, 1769-79 (2012)) and TCGA tumor samples are known to contain variable amounts of immune infiltrates (Corces, M. R. et al. The chromatin accessibility landscape of primary human cancers. *Science* 362 (2018)). In some embodiments, it was investigated whether H2A.B expression was associated with immune infiltrates, as this could confound our transcriptome analyses. It was found that transcript levels for markers of B-cells, T-cell subsets, NK cells, monocytes and activated macrophages did not show consistent enrichment across H2A.B-expressing tumors (FIG. 7). In fact, UCEC displayed a statistically significant decrease in PRF1 expression as well as several macrophage and neutrophil markers. Several sH2A-derived peptides are predicted to bind HLA molecules (Lundegaard, C. et al. NetMHC-3.0: accurate web accessible predictions of human, mouse and monkey MHC class I affinities for peptides of length 8-11. *Nucleic Acids Res* 36, W509-12 (2008); Nielsen, M. et al. Reliable prediction of T-cell epitopes using neural networks with novel sequence representations. *Protein Sci* 12, 1007-17 (2003)) (Supplementary Data 6), suggesting an immunosuppressive microenvironment may contribute to sustained H2A.B expression in UCEC. The lack of excess immune infiltrates in H2A.B-positive TCGA specimens and the identification of H2A.B-positive cancer cell lines (FIG. 2C) support H2A.B upregulation in cancer cells, though a contribution from surrounding stroma in patient specimens cannot be excluded.

H2A.B-Expressing Cancers have Distinct Splicing Patterns

Figure 4A:
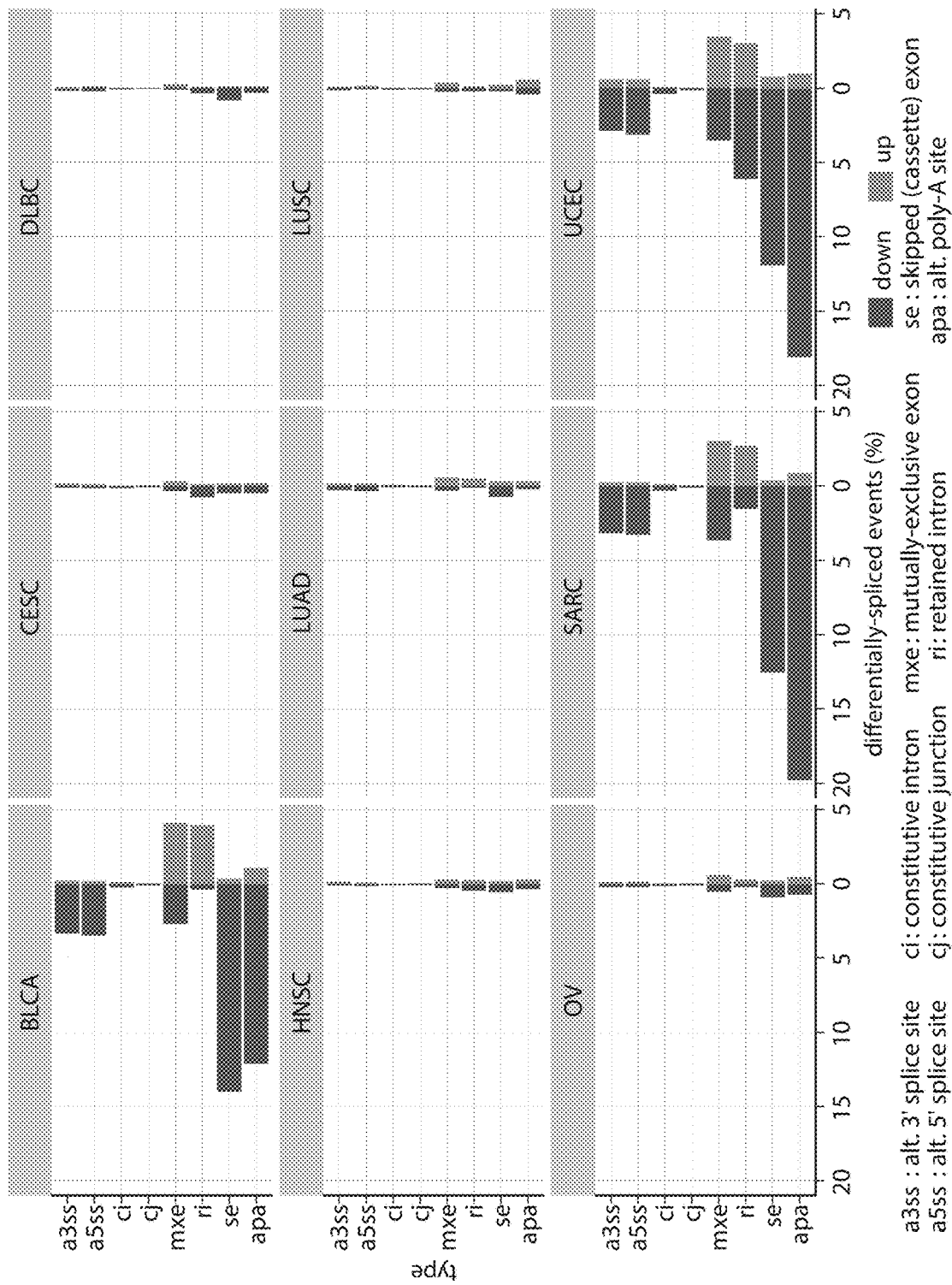
FIGS. 4A to 4C. Splicing analyses in H2A.B-reactivated cancers.
Figure 4B:
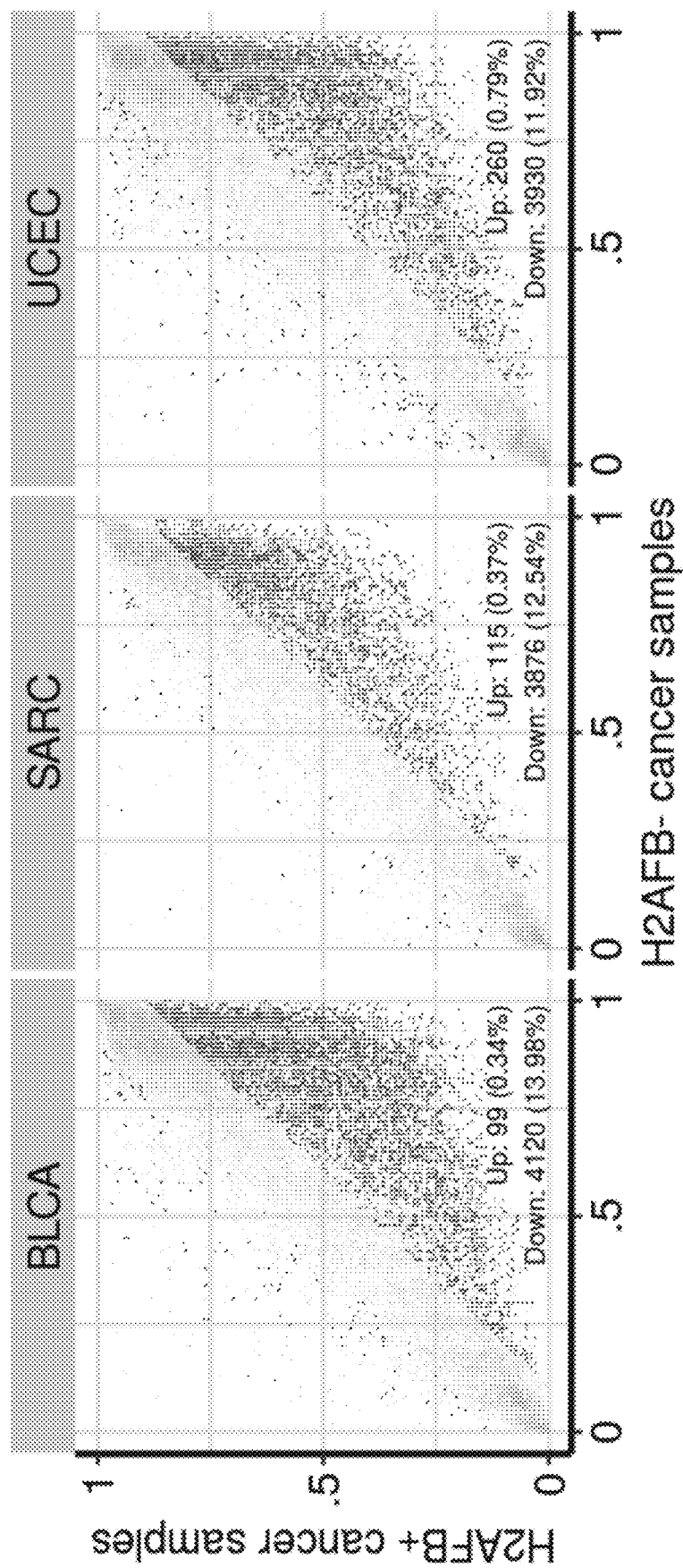
Figure 8A:
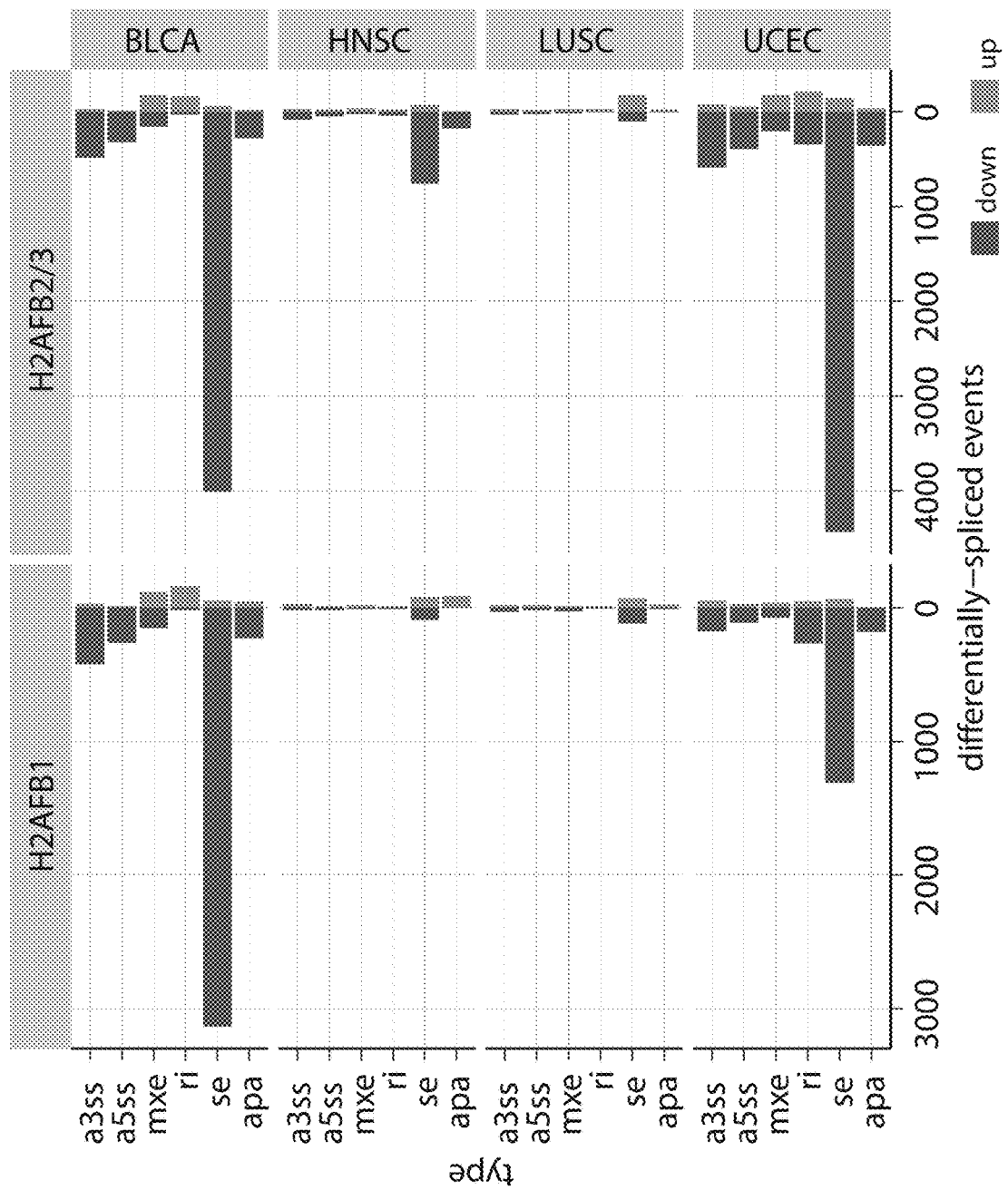
FIGS. 8A to 8F.
Figure 8B:
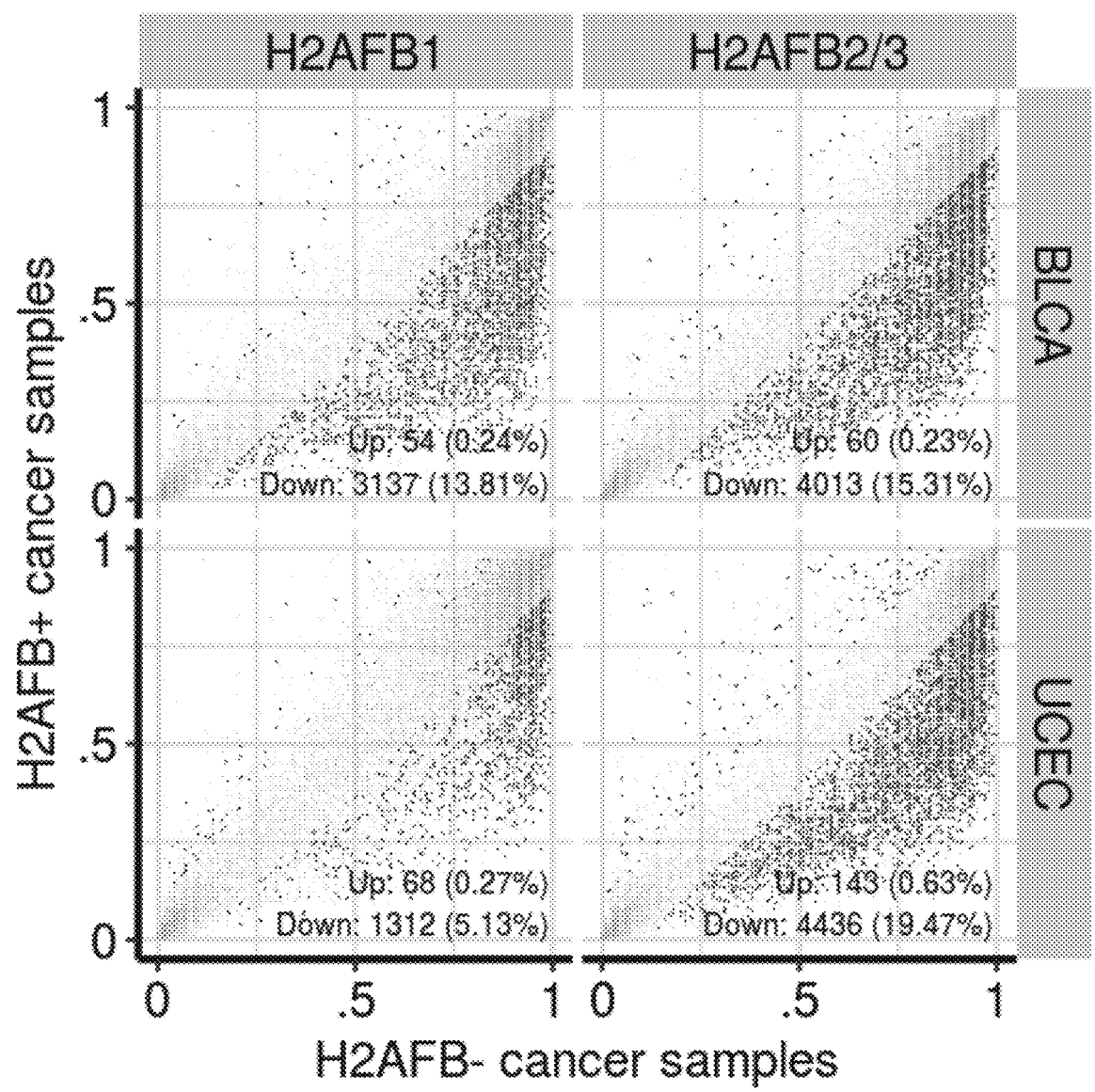
Figure 8C:
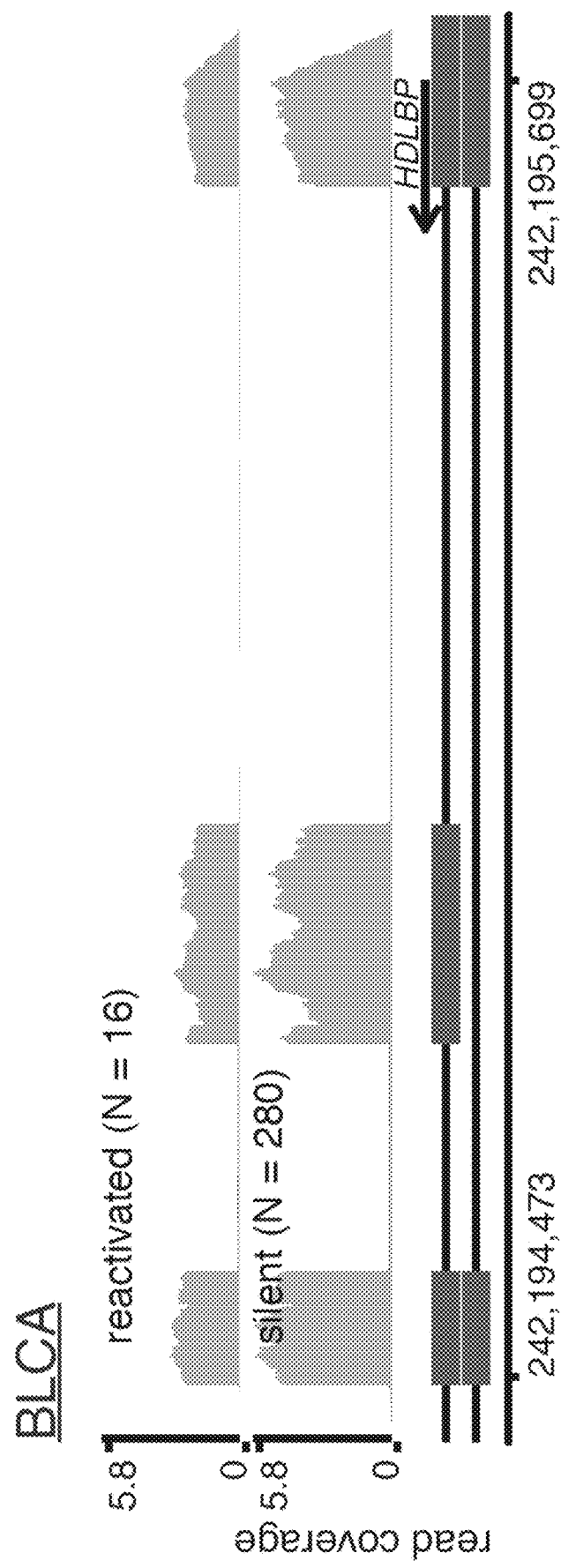
Figure 8D:
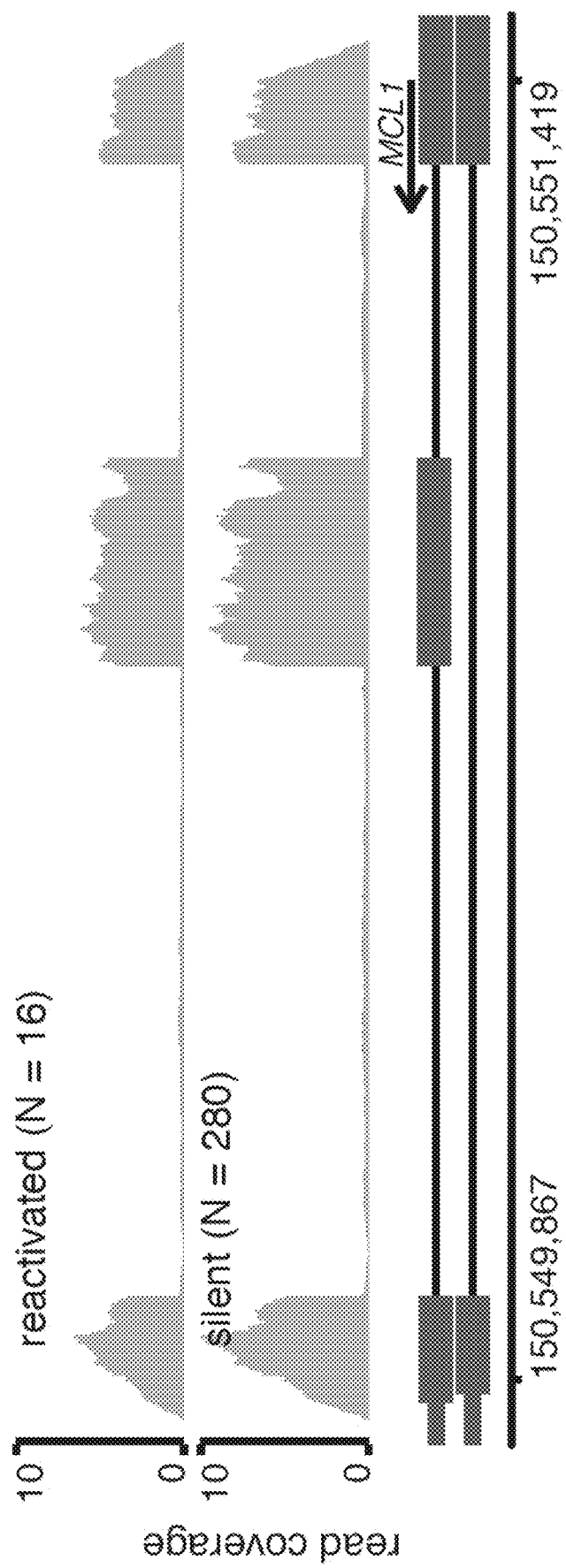
Figure 8E:
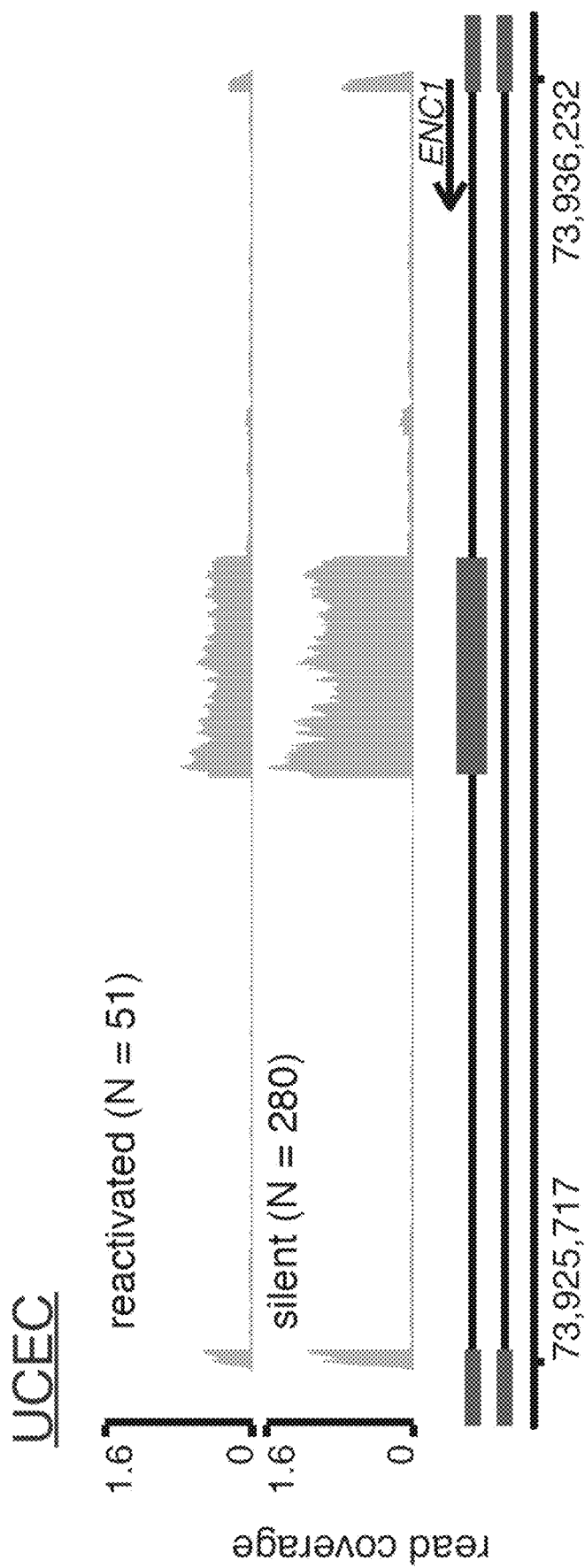
Figure 8F:
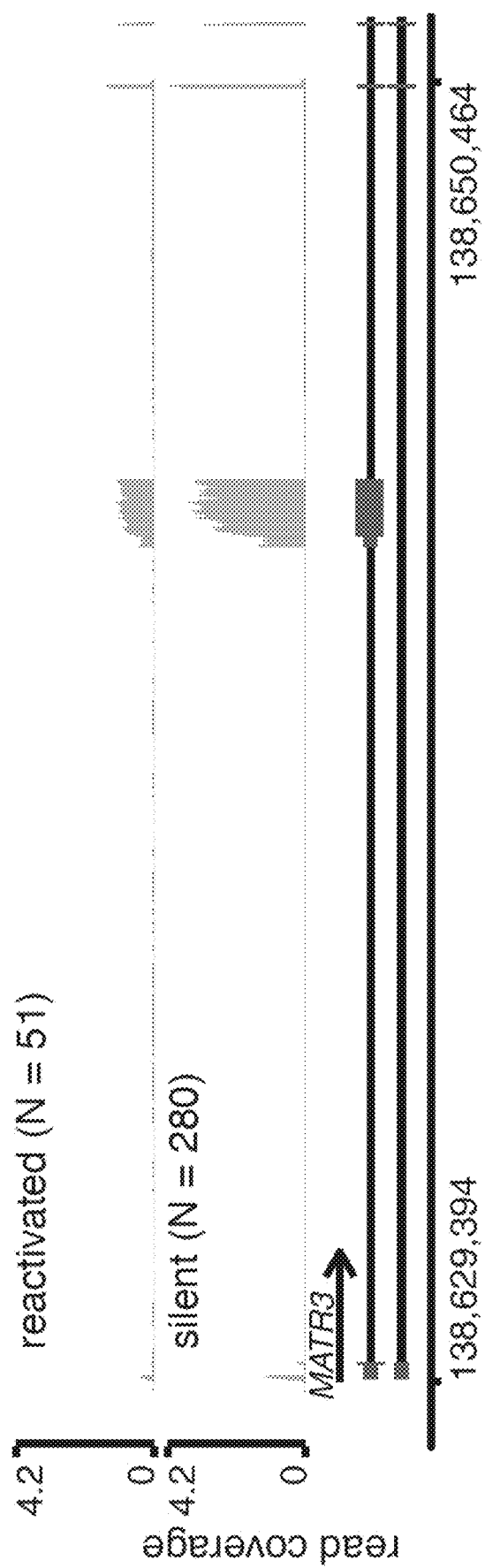

H2A.B has been shown to directly bind RNA and interacts with splicing factors, and H2A.B expression impacts alternative splicing patterns (Tolstorukov, M. Y. et al. Histone variant H2A.Bbd is associated with active transcription and mRNA processing in human cells. *Mol Cell* 47, 596-607 (2012); Anuar, N. D. et al. Gene editing of the multi-copy H2A.B gene and its importance for fertility. *Genome Biol* 20, 23 (2019); Soboleva, T. A. et al. A new link between transcriptional initiation and pre-mRNA splicing: The RNA binding histone variant H2A.B. *PLoS Genet* 13, e1006633 (2017); Hoghoughi, N., Barral, S., Vargas, A., Rousseaux, S. & Khochbin, S. Histone variants: essential actors in male genome programming *J Biochem* 163, 97-103 (2018 Sansoni, V. et al. The histone variant H2A.Bbd is enriched at sites of DNA synthesis. *Nucleic Acids Res* 42, 6405-20 (2014)). To determine if H2A.B expression is associated with splicing dysregulation, all constitutive and alternative splicing events in the transcriptomes of H2A.B-reactivated and silent tumors from the TCGA dataset were annotated and quantified. Thousands of altered splicing events were uncovered between these cancers (FIGS. 4A and 4B). It was found that H2A.B expression is associated with reduced utilization of alternative "cassette exons" (se) and proximal alternative 3' polyadenylation (APA) sites (FIGS. 8A and 8B). These features were particularly prominent in BLCA, SARC and UCEC (FIGS. 4A and 8A). While the changes are individually modest (FIGS. 8C-8F and Supplementary Data 7), they are widespread, i.e., significant changes were observed at thousands of sites across multiple cancer types (FIGS. 4A and 4B). These patterns are not H2A.B paralogue-specific, as similar patterns were observed in specimens expressing either H2AFB1 or H2AFB2/3 (FIGS. 8A and 8B).

Figure 4C:
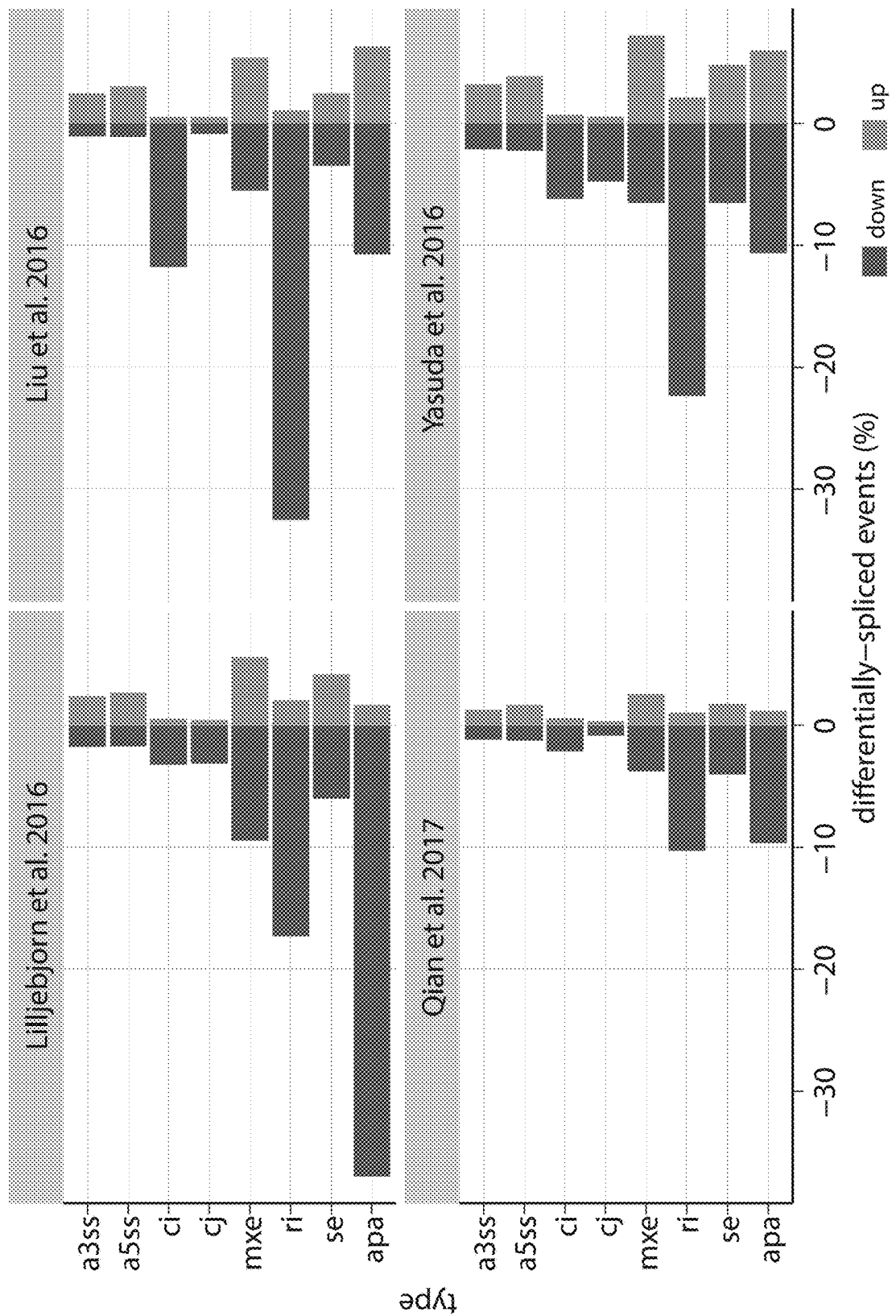

In some embodiments, splicing in the four B-ALL datasets was explored. Unlike in myelodysplastic syndromes and acute myelogenous leukemias (AMLs) (Dvinge, H., Kim, E., Abdel-Wahab, O. & Bradley, R. K. RNA splicing factors as oncoproteins and tumour suppressors. *Nat Rev Cancer* 16, 413-30 (2016)), B-ALLs are not associated with mutations in splicing factors and global splicing dysregulation is not thought to be a major driver of these leukemias. When splicing patterns were compared in the H2A.B-reactivated and silent samples within each dataset, aberrant splicing was observed at a scale similar to that seen in H2A.B-positive TCGA cancers, with reductions in alternative exon and APA usage. However, the most notable feature is a consistent decrease in retained introns "ri" in all four datasets (FIG. 4C). From these observations, it was concluded that H2A.B expression is associated with splicing dysfunction, with some features common among many cancers while others occur in a context-specific manner Discussion The discovery of oncohistone mutations has revealed new insights into the biology of cancer. In this Example, it was disclosed that all mammalian genomes already encode sH2A histone variants that have evolved nucleosome-destabilizing features without any additional coding mutations. These features are important for sH2As' roles in normal testis physiology but result in oncohistone properties when expressed out of context. In this manner, they are similar to CATACOMB/EZHIP (Piunti, A. et al. CATACOMB: An endogenous inducible gene that antagonizes H3K27 methylation activity of Polycomb repressive complex 2 via an H3K27M-like mechanism. *Sci Adv* 5, eaax2887 (2019); Jain, S. U. et al. PFA ependymoma-associated protein EZHIP inhibits PRC2 activity through a H3 K27M-like mechanism. *Nat Commun* 10, 2146 (2019)), another testis-specific oncohistone mimic that inhibits EZH2 in a subset of rare malignancies. Unlike CATACOMB/EZHIP, however, H2A.B expression occurs in many common cancers. The diversity of H2A.B-expressing cancer types suggests that pathological histone dynamics play a more significant role in neoplasia than previously appreciated.

The precise molecular targets of H2A.B expression in cancers are not known. Relatively few genes are commonly-dysregulated across H2A.B-positive malignancies (Supplementary Data 5), implying that H2A.B impacts different genes in different cancers. As nucleosomes protect DNA from inappropriate transcription factor (TF) binding, nucleosome instability may allow oncogenic TFs access to different regulatory elements depending on cancer type (Bennett, R. L. et al. A Mutation in Histone H2B Represents a New Class of Oncogenic Driver. *Cancer Discov* (2019); Sarthy, J. F., Henikoff, S. & Ahmad, K. Chromatin Bottlenecks in Cancer. *Trends Cancer* 5, 183-194 (2019)). Nucleosome destabilization also hastens RNA pol II elongation, which in turn reduces transcription-coupled splicing efficiency (Jimeno-Gonzalez, S. et al. Defective histone supply causes changes in RNA polymerase II elongation rate and cotranscriptional pre-mRNA splicing. *Proc Natl Acad Sci USA* 112, 14840-5 (2015)). Alternative exons and proximal polyadenylation sequences are preferentially impacted by inefficient splicing due to their weaker splice signals, resulting in a splicing phenotype similar to those observed in several H2A.B-positive cancers (Jimeno-Gonzalez, S. et al. Defective histone supply causes changes in RNA polymerase II elongation rate and cotranscriptional pre-mRNA splicing. *Proc Natl Acad Sci USA* 112, 14840-5 (2015)). As some alternative exons promote mRNA degradation by targeting them for nonsense mediated decay, even modest reductions in alternative splicing can increase oncogene expression (Thomas, J. D. et al. RNA isoform screens uncover the essentiality and tumor-suppressor activity of ultraconserved poison exons. *Nat Genet* 52, 84-94 (2020)). H2A.B may operate at the *nexus* of several processes that cooperate to drive oncogenesis.

The relationship between histone dynamics, transcription and splicing may also explain our inability to detect a splicing phenotype in DLBCLs despite high frequency H2A.B expression. Many chromatin proteins are deranged in DLBCLs including Myc, p300, H1 linker and core histones, each of which can also impact alternative splicing (Chapuy, B. et al. Molecular subtypes of diffuse large B cell lymphoma are associated with distinct pathogenic mechanisms and outcomes. *Nat Med* 24, 679-690 (2018); Koh, C. M. et al. MYC regulates the core pre-mRNA splicing machinery as an essential step in lymphomagenesis. *Nature* 523, 96-100 (2015); Siam, A. et al. Regulation of alternative splicing by p300-mediated acetylation of splicing factors. *RNA* 25, 813-824 (2019); Glaich, O., Leader, Y., Lev Maor, G. & Ast, G. Histone H1.5 binds over splice sites in chromatin and regulates alternative splicing. *Nucleic Acids Res* 47, 6145-6159 (2019). Whether potential similarities between HFD-mutant cancers and H2A.B-expressing cancers extend to prognoses and vulnerabilities merits further investigation particularly in the context of DLBCL where larger data sets are needed to dissect these relationships. Several cell lines show sensitivity to H2AFB/-gRNAs in the Sanger Cancer Dependency Map, with lymphoma-derived cell lines SU-DHL-8 and IM9 being among the most sensitive to H2AFB1 disruption (Behan, F. M. et al. Prioritization of cancer therapeutic targets using CRISPR-Cas9 screens. Nature 568, 511-516 (2019)). Better characterization of histone mutations and H2A.B expression across cancer cell lines is needed in order to probe for similarities between H2A.B-expressing cancers and histone mutant cancers. Finally, sH2A-derived short peptides that bind human leukocyte antigen (HLA) molecules (Supplementary Data 6) may be useful immunotherapy targets, and global splicing dysregulation can also generate highly immunogenic neoantigens (Shen, L., Zhang, J., Lee, H., Batista, M. T. & Johnston, S. A. RNA Transcription and Splicing Errors as a Source of Cancer Frameshift Neoantigens for Vaccines. *Sci Rep* 9, 14184 (2019)). Thus, our discovery of sH2A-expressing cancers may open new avenues of study and treatment for hundreds of thousands of cancer cases worldwide.

Methods

Alignments of sH2A Sequences sH2A and other H2A sequences were retrieved from Histone DB v2 (Draizen, E. J. et al. HistoneDB 2.0: a histone database with variants—an integrated resource to explore histones and their variants. *Database (Oxford)* 2016 (2016)) and previously published work (Molaro, A., Young, J. M. & Malik, H. S. Evolutionary origins and diversification of testis-specific short histone H2A variants in mammals. *Genome Res* 28, 460-473 (2018)). Predicted protein sequences from annotated CDS were aligned using ClustalW and manually curated. For primate alignments, sequences were arranged according to the accepted species phylogeny.

Genome annotation, RNA-seq read mapping, and gene and isoform expression estimation. RNA-seq reads from TCGA were downloaded from CGHub. Reads were processed for gene expression and splice isoform ratio quantification as previously described (Katz, Y., Wang, E. T., Airoldi, E. M. & Burge, C. B. Analysis and design of RNA sequencing experiments for identifying isoform regulation. *Nat. Methods* 7, 1009-1015 (2010)). Briefly, read alignment and expression estimation were performed with RSEM v1.2.443 (Li, B. & Dewey, C. N. RSEM: accurate transcript quantification from RNA-Seq data with or without a reference genome. *BMC Bioinformatics* 12, 323 (2011)), Bowtie v1.0.044 (Langmead, B., Trapnell, C., Pop, M. & Salzberg, S. L. Ultrafast and memoryefficient alignment of short DNA sequences to the human genome. *Genome Biol.* 10, R25 (2009).), and TopHat v2.1.145 (Trapnell, C., Pachter, L. & Salzberg, S. L. TopHat: discovering splice junctions with RNA-Seq. *Bioinformatics* 25, 1105-1111 (2009)), using the hg19/GRCh37 assembly of the human genome with a gene annotation that merges the UCSC known Gene gene annotation (Meyer, L. R. et al. The UCSC Genome Browser database: extensions and updates 2013. *Nucleic Acids Res.* 41, D64-D69 (2013)), Ensembl v71.1 gene annotation (Flicek, P. et al. Ensembl 2013. *Nucleic Acids Res.* 41, D48-D55 (2013)), and MISO v2.0 isoform annotation (Katz, Y., Wang, E. T., Airoldi, E. M. & Burge, C. B. Analysis and design of RNA sequencing experiments for identifying isoform regulation. *Nat. Methods* 7, 1009-1015 (2010)). MISO v2.038 was used to quantify isoform ratios. The trimmed mean of M values (TMM) method (Robinson, M. D. & Oshlack, A. A scaling normalization method for differential expression analysis of RNA-seq data. *Genome Biol.* 11, R25 (2010)), as applied to coding genes, was used to normalize gene expression estimates across all of TCGA.

Data analysis and visualization. Data analysis was performed in the R programming environment and relied on Bioconductor (Huber, W. et al. Orchestrating high-throughput genomic analysis with Bioconductor. *Nat. Methods* 12, 115-121 (2015)), dplyr (Wickham, H., Francois, R., Henry, L., Muller, K. dplyr: A G 0.7.6 https://CRAN.R-project.org/package=dplyr. (2018)), and ggplot2 (Wickham, H. ggplot2: Elegant Graphics for Data Analysis., (Springer-Verlag, New York, N.Y., 2016))

RNA-seq coverage plots. RNA-seq coverage plots (i.e., FIGS. 8C to 8F) were made using the ggplot2 package in R, and represent reads normalized by the number of reads mapping to all coding genes in each sample (per million).

Somatic mutation analysis. TCGA somatic mutation calls from the Mutect pipeline (Cibulskis, K. et al. Sensitive detection of somatic point mutations in impure and heterogeneous cancer samples. *Nat. Biotechnol.* 31, 213-219 (2013)), were obtained using the GDCquery_Maf function from TCGAbiolinks (Colaprico, A. et al. TCGAbiolinks: an R/Bioconductor package for integrative analysis of TCGA data. *Nucleic Acids Res.* 44, e71 (2016)). Mutations in the following canonical histones were collated by their class: H2A-HIST1H2A(A/B/C/D/E/G/H/I/J/K/L/M), HIST2H2A (B/C), HIS3H2A; H2B-HIST1H2B (A/B/C/D/E/F/G/H/I/J/K/L/M/N/O), HIST2H2B(E/F), HIST3H2BB. Recurrent mutations (Supplementary Data 3) are defined as occurring at least 5 times across all cancer types in TCGA (e.g. 10 instances of E121Q mutations are found in various H2As across all TCGA samples).

Differential gene expression and splice event analyses. For the purposes of differential analyses, a threshold of >1.5 transcripts-per-million (TPM) was used to determine if H2A.B was expressed in a sample, while a threshold of <0.5 TPM was used to determine if H2A.B was not expressed; samples with an intermediate expression of H2A.B were not used in differential analyses. Statistical significance in differential expression or splicing in H2A.B-positive versus H2A.B-negative cancer samples was determined with a Mann-Whitney test, as implemented in wilcox.test in R.

Prediction of H2A variant candidate T cell epitopes. The amino acid sequence of human H2A.B.1.1_H2AFB2, H2A.B.1.2_H2AFB3, H2A.B.2_H2AFB1, H2A.Q and H2A.P_HYPM were examined for short peptides with the potential to bind to common HLA alleles (Lundegaard, C. et al. NetMHC-3.0: accurate web accessible predictions of human, mouse and monkey MHC class I affinities for peptides of length 8-11. *Nucleic Acids Res.* 36, W509-W512 (2008); Nielsen, M. et al. Reliable prediction of T-cell epitopes using neural networks with novel sequence representations. *Protein Sci.* 12, 1007-1017 (2003). Specifically, the NetPanMHCBA4.0 algorithm of the Immune Epitope Database and Analysis Resource (IEDB) was used to identify peptides of 8, 9, 10 or 11 amino acids long that are predicted to bind with strong affinity (IC50<300 nM) to HLA-A*0101, A*0201, A*0301, A*1101, A*2402, B*0702, B*0801, B*1501, B*1502, B*4001, B*4002, B*4402 or B*4403. Additional IEDB algorithms were employed to confirm predicted HLA binding, whereby binding was predicted by NetPanMHCBA4.0 and at least one other method (including Artificial neural network (ANN), Stabilized matrix method (SMM), PickPocket and NetPanMHCBA4.0) was required for inclusion in Supplementary Data 6.

Example 2

This Example describes that the H2A.B variant is primarily expressed in testis in normal cells, i.e., non-malignant cells.

Figure 9A:
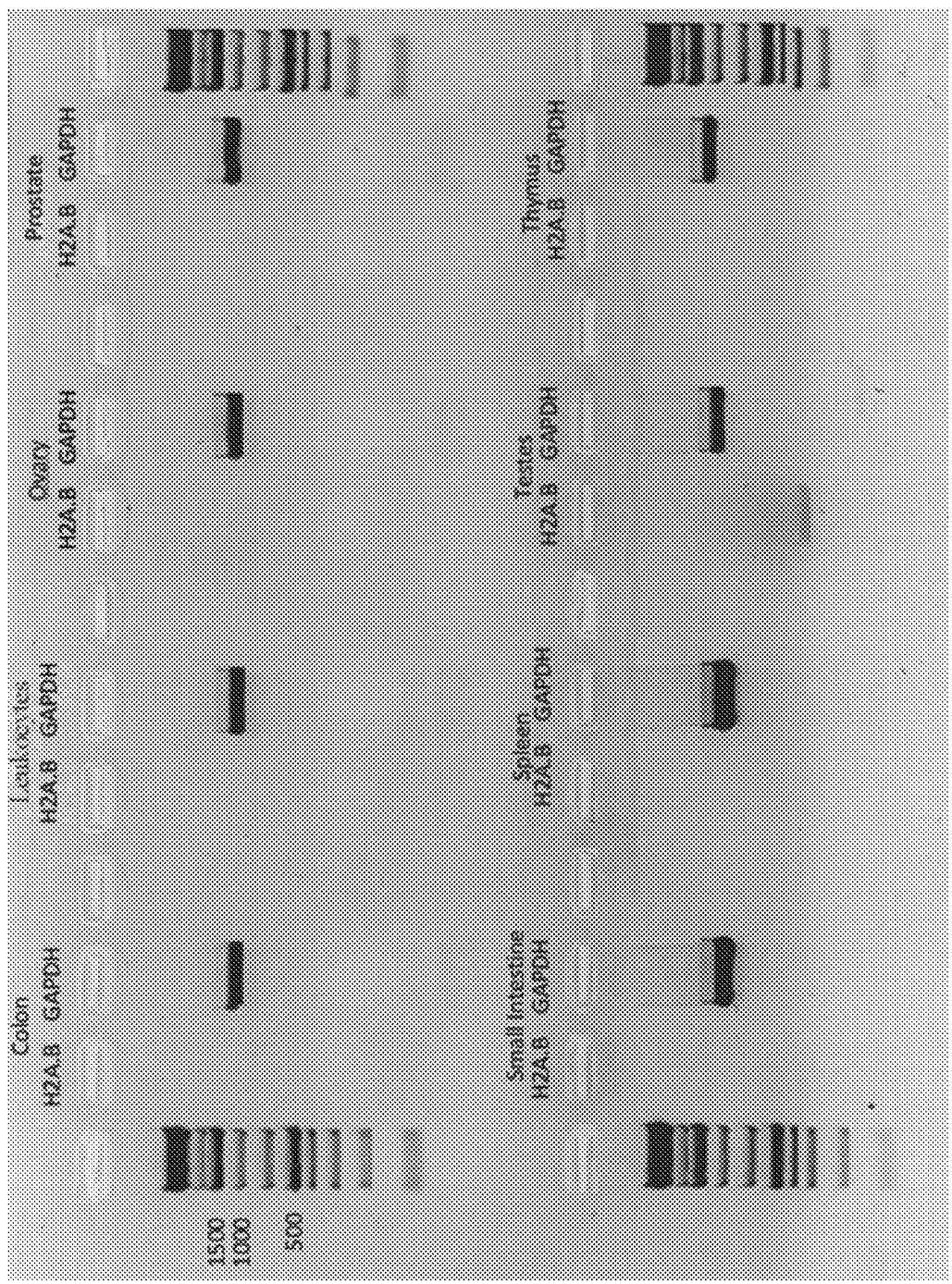
FIGS. 9A to 9B. RT-PCR from Takara Biosciences Multiple Tissue cDNA Panel shows H2A.B expression is restricted to testis in normal cells. GAPDH is shown as PCR control.
Figure 9B:

The H2A.B variant is encoded by three paralogues on the X-chromosome, H2AFB1, H2AFB2, and H2AFB3 (Molaro, A., Young, J. M. & Malik, H. S. Evolutionary origins and diversification of testis-specific short histone H2A variants in mammals. *Genome Res* 28, 460-473 (2018)). By probing large-scale transcriptomic datasets from cancer specimens and healthy controls, it was found that H2A.B is not expressed in normal tissue outside of testis, but is expressed in a broad array of solid and liquid malignancies (Chew, G. L. et al. Short H2A histone variants are expressed in cancer. *Nat Commun* 12, 490 (2021)). The inventors confirmed these findings by using RT-PCR in a panel of healthy tissues (FIGS. 9A and 9B). In some embodiments, H2A.B expression was identified in 50% of diffuse large B-cell lymphomas and 10% of uterine carcinomas in The Cancer Genome Atlas dataset. Given the high prevalence of H2A.B expression in DLBCL, B-acute lymphoblastic lymphoma datasets were then probed and this analysis identified expression in 5-10% of B-ALL specimens (Chew, G. L. et al. Short H2A histone variants are expressed in cancer. *Nat Commun* 12, 490 (2021)). To confirm that H2A.B expression was occurring in cancer cells and not adjacent tissue, a comprehensive analyses of markers associated with immune infiltrates was performed and from this analysis there was no finding of overrepresentation of any marker in H2A.B-positive cancer specimens (Chew, G. L. et al. Short H2A histone variants are expressed in cancer. *Nat Commun* 12, 490 (2021)). In some embodiments, expression in cancer cells was tested by exploring the Cancer Cell Line Encyclopedia (CCLE), where dozens of H2A.B-positive cell lines were found with lymph-derived cancers having highest expression. H2A.B expression was confirmed in L-428, L-1236 HL, SU-DHL-1, SUPM2 ALCL, and SU-DHL-8 DLBCL lines by RT-PCR, including an additional 15 lymphoma cell lines with H2A.B expression >1.5 transcripts per million that will be verified by RT-PCR (data not shown).

Example 3

This Example describes that loss of H2A.B expression inhibits cancer cell proliferation.

Figure 10A:
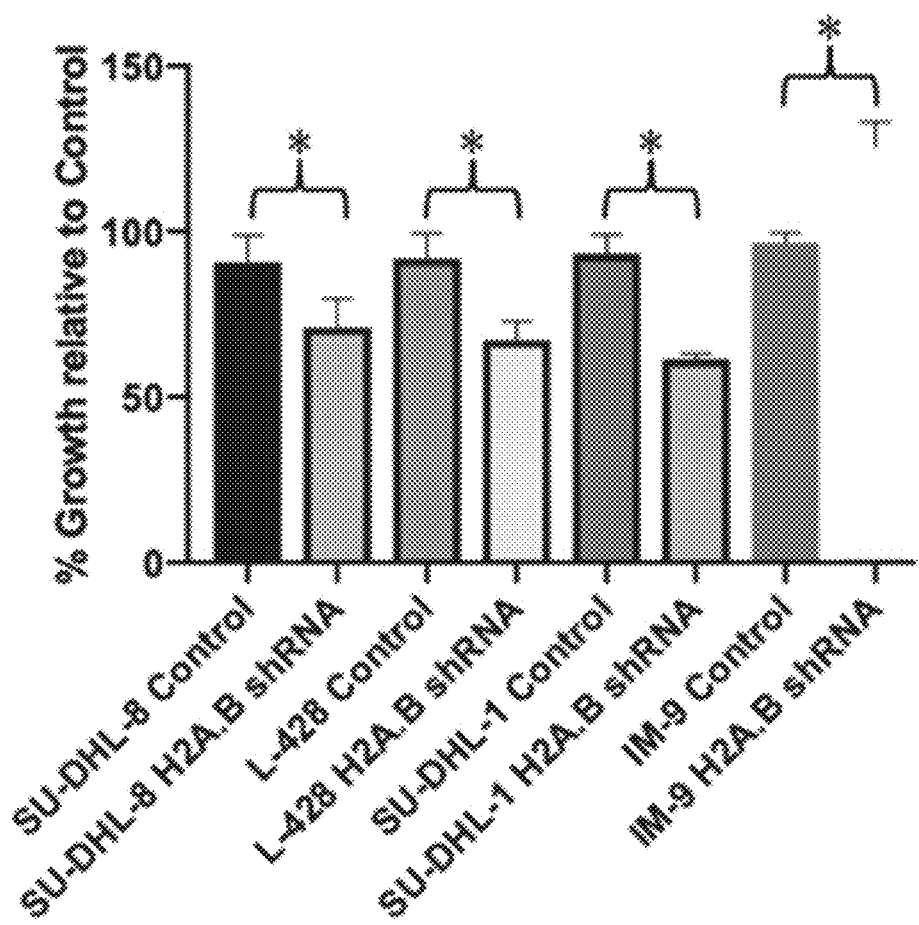
FIGS. 10A to 10B. H2A.B loss inhibits cancer cell proliferation.
Figure 10B:
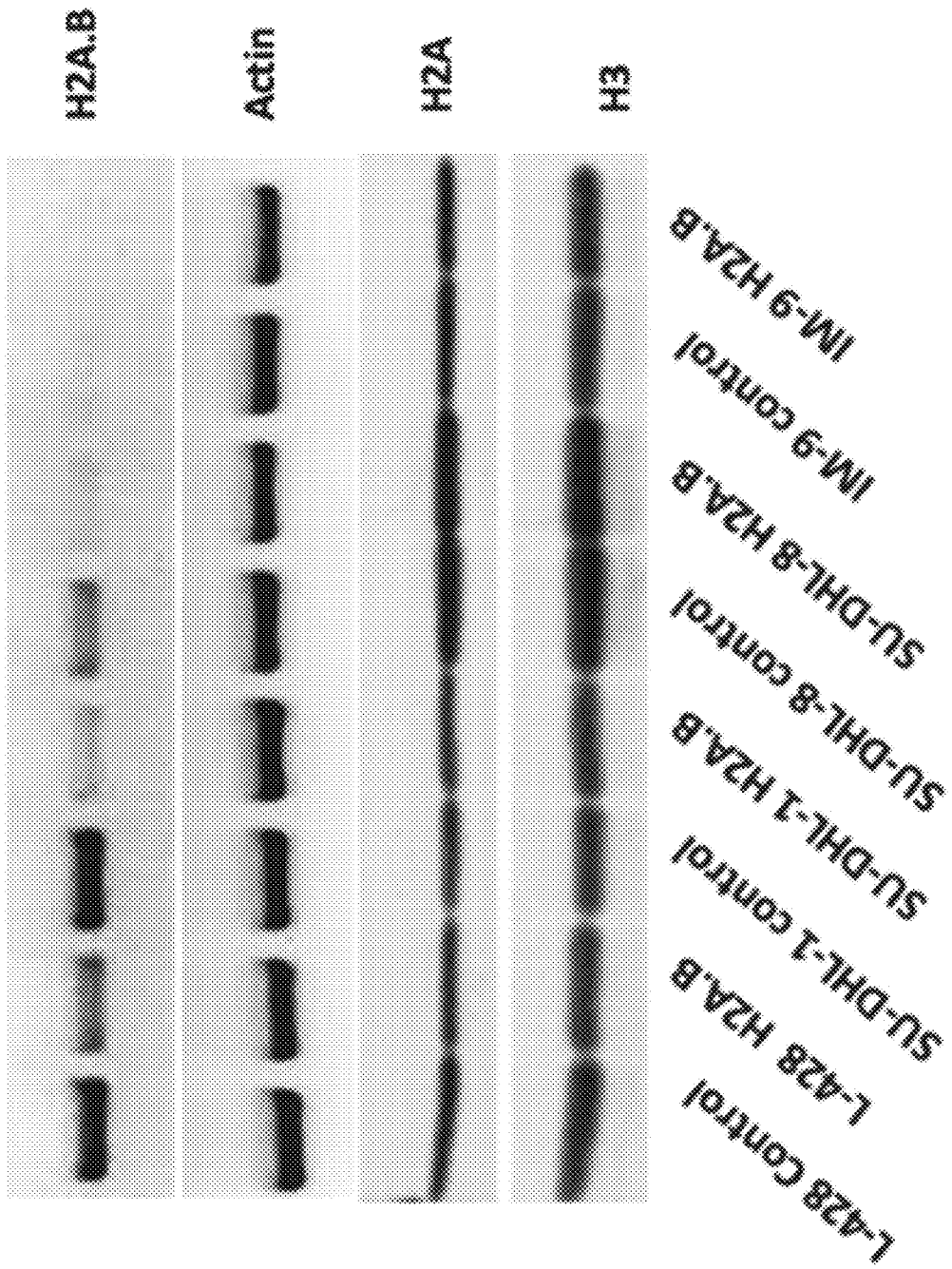

To determine whether H2A.B expression is consequential in cancer cells, two separate genome-wide CRISPR screens were performed to target H2A.B expression (Meyers, R. M. et al. Computational correction of copy number effect improves specificity of CRISPR-Cas9 essentiality screens in cancer cells. *Nat Genet* 49, 1779-1784 (2017); Reddy, A. et al. Genetic and Functional Drivers of Diffuse Large B Cell Lymphoma. *Cell* 171, 481-494 e15 (2017)). In one screen with 323 different cancer cell lines, the cell line with the most significant fitness reduction in response to H2A.B-targeting gRNAs was SU-DHL-8, a diffuse large B-cell lymphoma (DLBCL) cell line (Meyers, R. M. et al. Computational correction of copy number effect improves specificity of CRISPR-Cas9 essentiality screens in cancer cells. *Nat Genet* 49, 1779-1784 (2017)). In a separate DLBCL-specific study, H2A.B-targeting gRNAs were a dependency in several cell lines (Reddy, A. et al. Genetic and Functional Drivers of Diffuse Large B Cell Lymphoma. *Cell* 171, 481-494 e15 (2017)). The only other H2A histone variant that showed similar dependency scores in both studies was H2A.Z, a variant deposited at sites of nucleosome turnover that was previously shown to promote oncogenesis (Valdes-Mora, F. et al. Acetylated histone variant H2A.Z is involved in the activation of neo-enhancers in prostate cancer. *Nat Commun* 8, 1346 (2017); Valdes-Mora, F. et al. Acetylation of H2A.Z is a key epigenetic modification associated with gene deregulation and epigenetic remodeling in cancer. *Genome Res* 22, 307-21 (2012)). Because of the high similarity between H2AFB1, H2AFB2 and H2AFB3, it is possible that the CRISPR results were in part mediated by inducing DNA breaks at all 3 H2A.B-encoding paralogues on the X-chromosome. To bypass this issue, a published shRNA was tested against H2A.B (Tolstorukov, M. Y. et al. Histone variant H2A.Bbd is associated with active transcription and mRNA processing in human cells. *Mol Cell* 47, 596-607 (2012)) and found that shRNA-induced H2A.B loss reduces proliferation in DLBCL, HL and ALCL cell lines (FIGS. 10A and 10B). This reduction in proliferation was not observed when the EBV-transformed lymphoblastoid cell line IM-9 was transduced with the same shRNA. Additionally, no reduction in global H2A levels were observed (FIGS. 10A and 10B)—the most likely off-target candidate. The combination of CRISPR data and shRNA data from this Example demonstrate that H2A.B promotes cancer cell growth.

Example 4

This Example describes that the anthracycline agent, aclarubicin, maximizes apoptosis while minimizing DNA damage in three different cancer cell lines.

Specific embodiments disclosed in this Example illustrate that aclarubicin efficiently kills lymphoma cells as measured by cleaved PARP, while inducing much less DNA damage, as measured by γ-H2A.X, than either doxorubicin or etoposide (FIGS. 11-13).

Figure 11A:
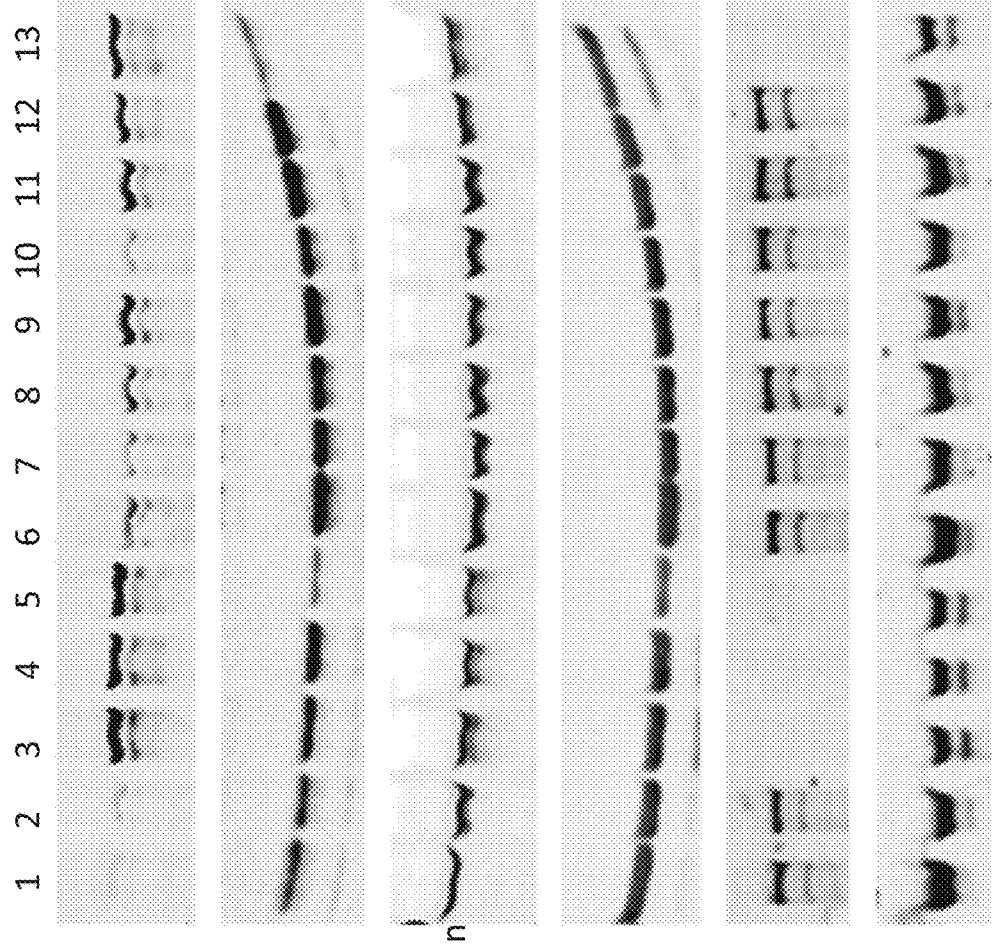
FIGS. 11A to 11B. Aclarubicin maximizes apoptosis while minimizing DNA damage in the Hodgkin's lymphoma cell line (L-1236).
Figure 11B:
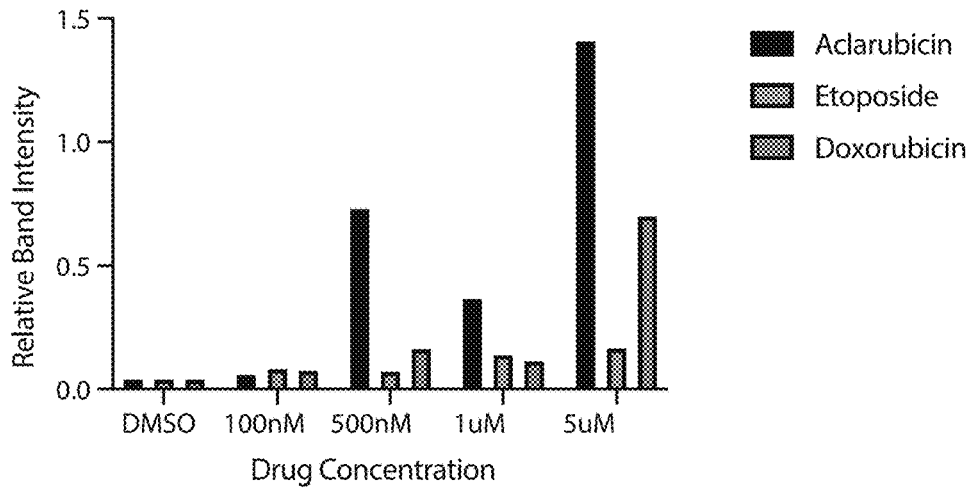
Figure 11B:
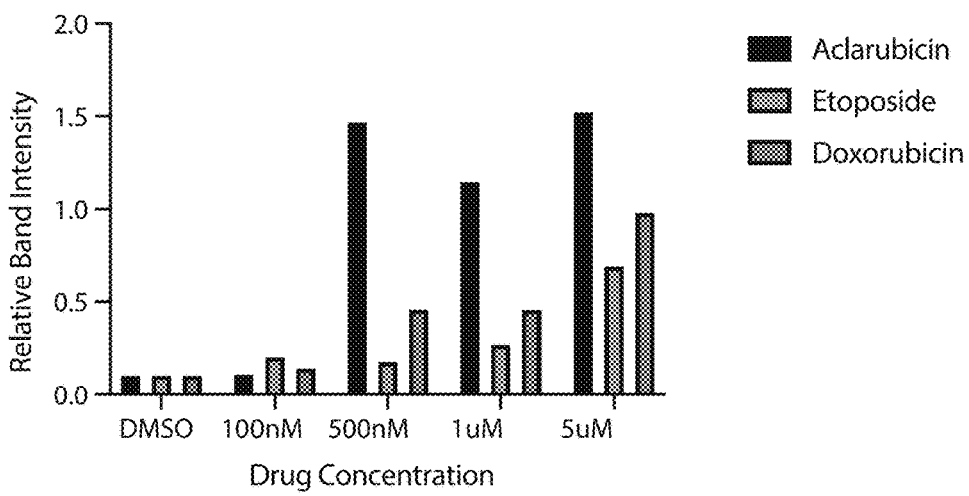
Figure 11B:
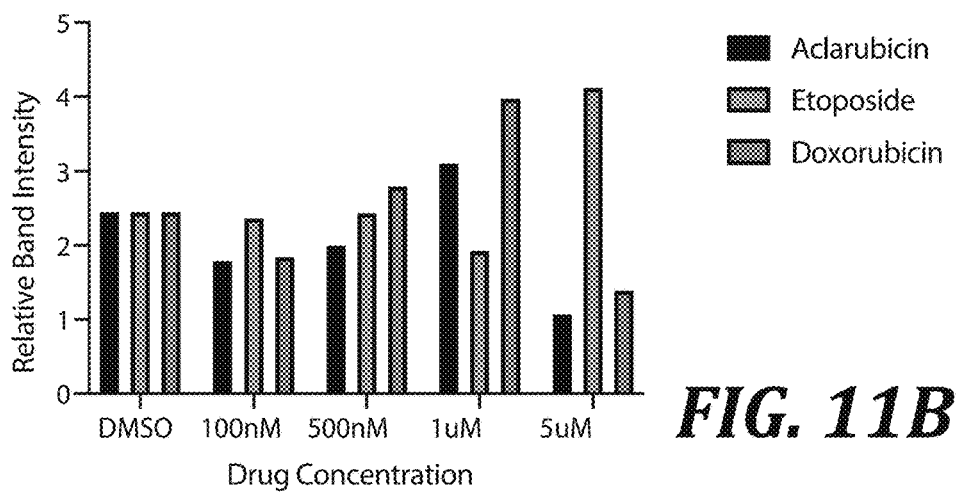
Figure 12A:
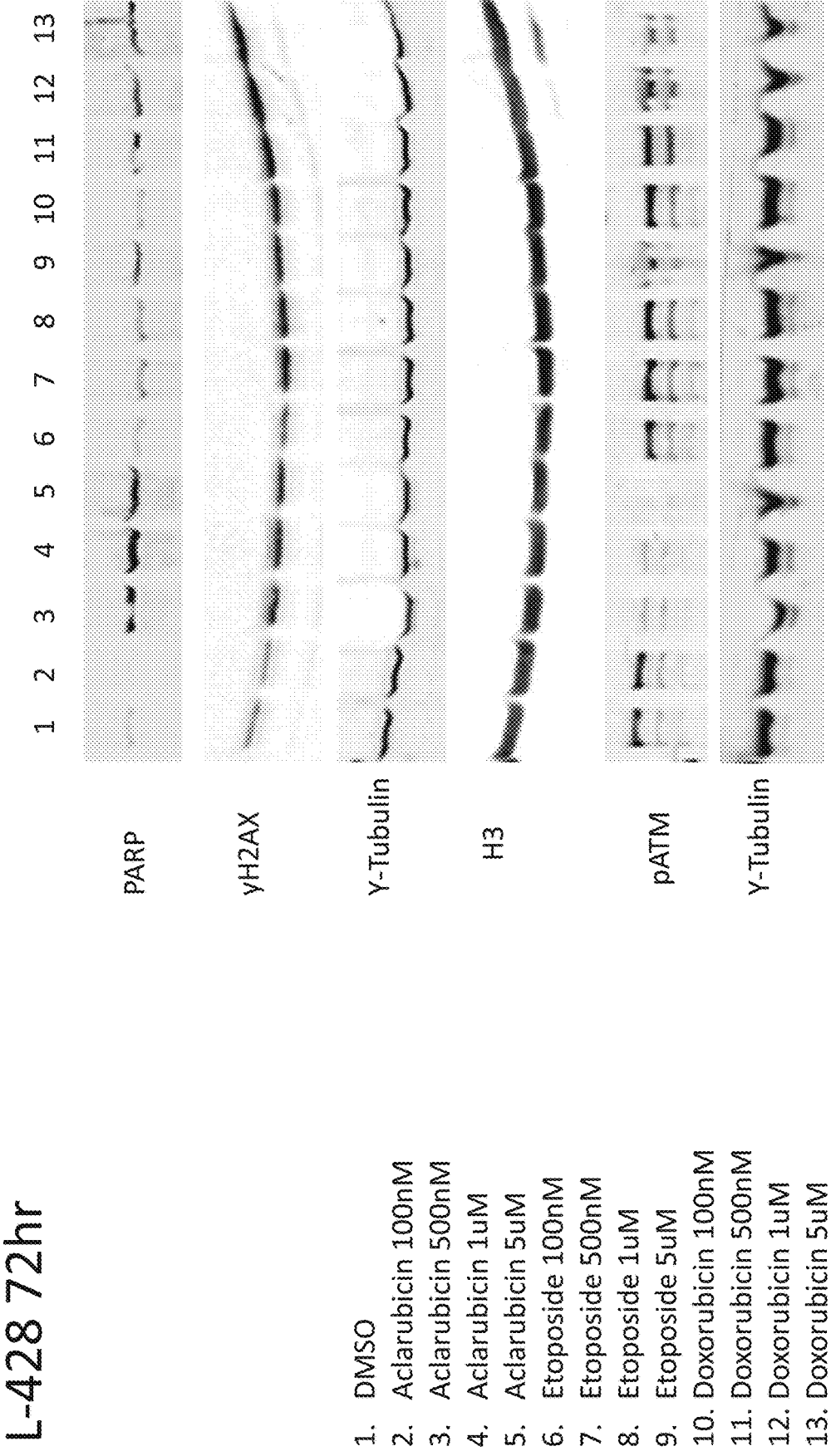
FIGS. 12A to 12B. Aclarubicin maximizes apoptosis while minimizing DNA damage in the Hodgkin's lymphoma cell line (L-428).
Figure 12B:
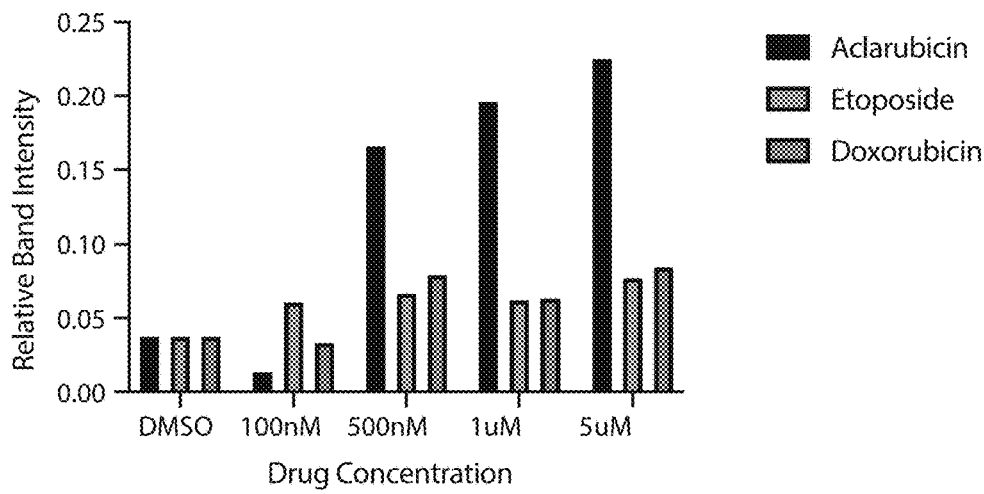
Figure 12B:
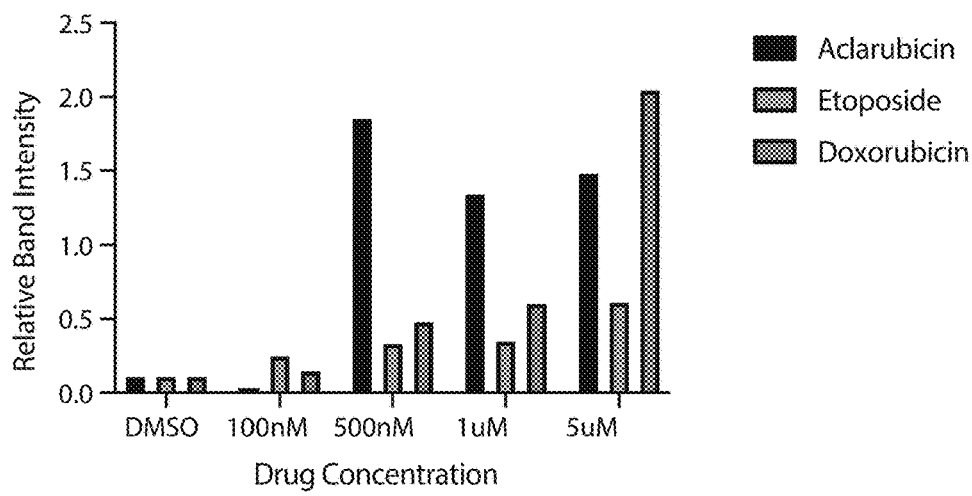
Figure 12B:
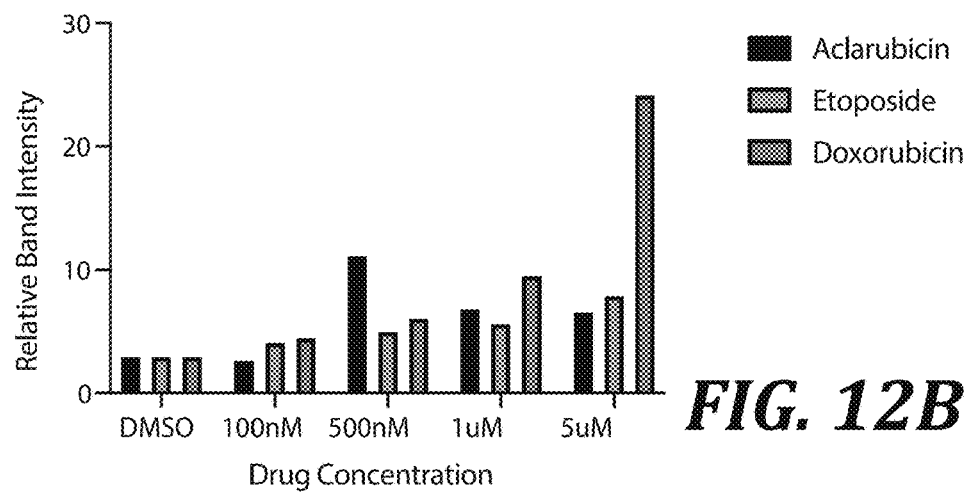
Figure 13A:
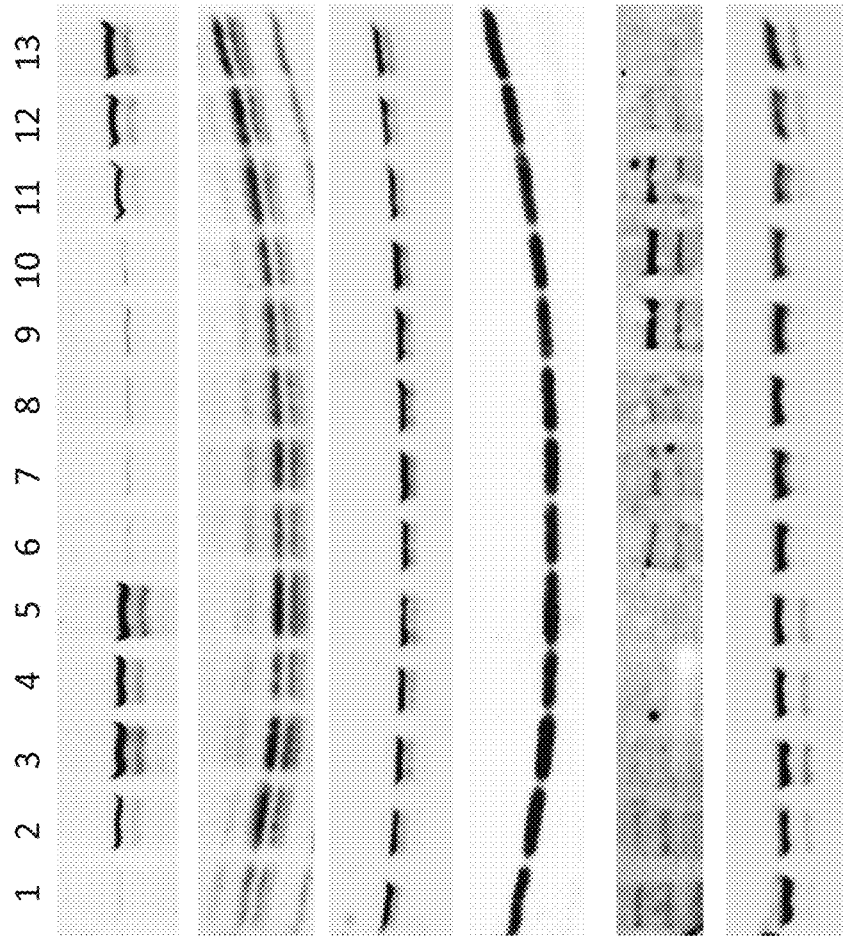
FIGS. 13A to 13B. Aclarubicin maximizes apoptosis while minimizing DNA damage in the diffuse large B-cell lymphoma cell line (A3/Kawakami).
Figure 13B:
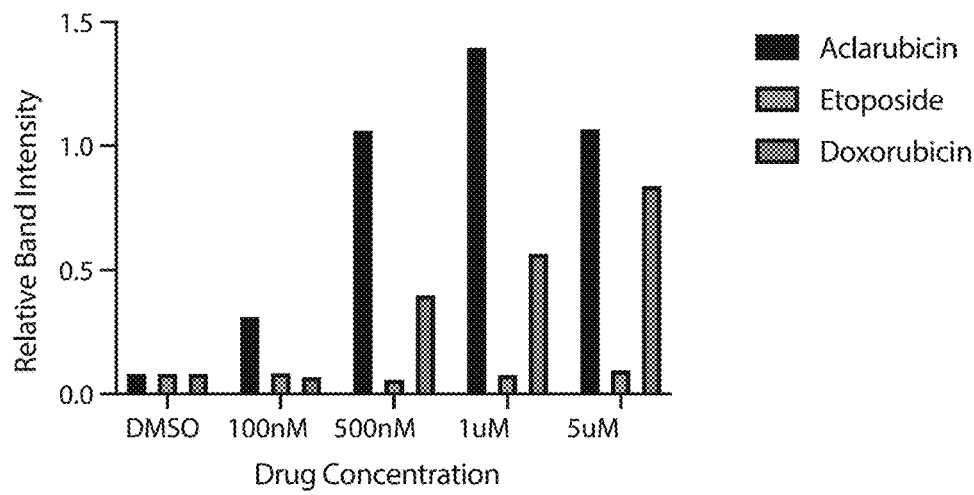
Figure 13B:
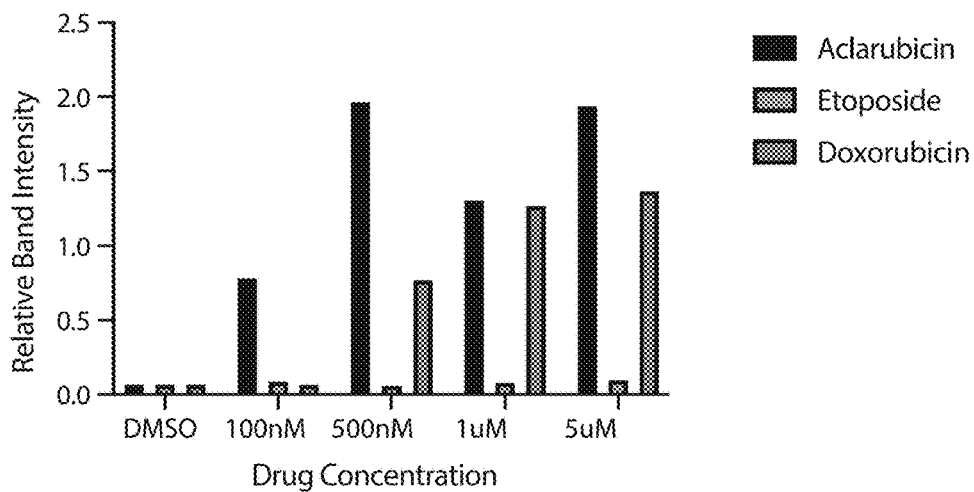
Figure 13B:
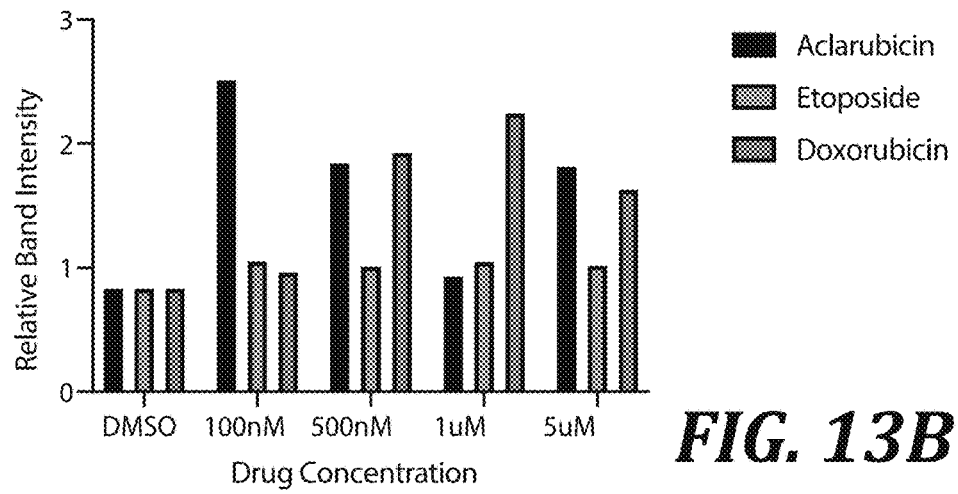

Specifically, as illustrated in FIG. 11A, experiments were performed on a Hodgkin's lymphoma cell line (L-1236) to test the cytotoxicity of aclarubicin (100 nM, 500 nM, 1.0 µM, and 5.0 µM) compared to etoposide (100 nM, 500 nM, 1.0 µM, and 5.0 µM) and doxorubicin (100 nM, 500 nM, 1.0 µM, and 5.0 µM), which are other commonly used cancer therapeutics. FIG. 11A is a Western blot gel assessing expression of the markers listed on the y-axis. The specific cancer therapeutics and the amounts used are indicated by the numbers along the x-axis and the corresponding figure legend. In this Example, aclarubicin's cytotoxicity on lymphoma cells was assessed by determining the amount of cleaved PARP, which was assessed as band intensity (FIG. 11B) from the Western blot (FIG. 11A). In this Example, aclarubicin's corresponding DNA damage was assessed by measuring the amount of γ-H2A.X, which was assessed as band intensity (FIG. 11B) from the Western blot (FIG. 11A). Specifically, as illustrated in FIG. 11B, the relative band intensity of PARP/tubulin, PARP/γ-H2A.X, and γ-H2A.X/Tubulin all indicate that aclarubicin has the best combination of anti-neoplastic activity while having fewer harmful side effects compare to either etoposide or doxorubicin.

In FIGS. 12 and 13, similar experiments were performed to compare the cytotoxicity of aclarubicin to etoposide and doxorubicin in additional lymphoma cell lines. In FIG. 12, the compounds cytotoxicity and side effects were assessed in the Hodgkin's lymphoma cell line, L-428. In FIG. 13, the compounds cytotoxicity and side effects were assessed in the diffuse large B-cell lymphoma cell line, A3/KAW. Similar to FIG. 11, the results from FIGS. 12 and 13 indicate that aclarubicin has the best combination of anti-neoplastic activity while having fewer harmful side effects compare to either etoposide or doxorubicin.

The results from this Example indicate that aclarubicin has a much more favorable side effect profile than doxorubicin and has more anti-neoplastic activity than etoposide. Therefore, lymphoma treatment regimens incorporating aclarubicin as the cytotoxic agent will lead to safer more effective treatment options for patients.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for treating a subject with lymphoma, the method comprising:
   (a) collecting a sample from a subject having or suspected of having lymphoma;
   (b) detecting a short histone H2A variant (sH2A) expression level in the sample collected from the subject;
   (c) administering to the subject a therapeutically effective dose of an anthracycline agent, if the subject has sH2A variant expression level that is detectable,
   wherein the anthracycline agent is selected from the group consisting of daunorubicin, doxorubicin, epirubicin, idarubicin, and aclarubicin.

2. The method of claim 1, wherein the sH2A variant is an H2A.B variant.

3. The method of claim 1, wherein the anthracycline agent is aclarubicin.

4. The method of claim 2, wherein the H2A.B variant comprises a sequence as set forth in SEQ ID NO:3 and/or SEQ ID NO:4.

5. The method of claim 1, wherein the lymphoma is Hodgkin's lymphoma.

6. A method of inducing cytotoxicity in a lymphoma cell expressing a short histone H2A (sH2A) variant, the method comprising administering to a subject in need thereof a pharmaceutical composition comprising a therapeutically effective dose of an anthracycline agent, wherein the anthracycline agent is selected from the group consisting of daunorubicin, doxorubicin, epirubicin, idarubicin, and aclarubicin.

7. The method of claim 6, wherein the subject has Hodgkin's lymphoma.

8. The method of claim 6, wherein the anthracycline agent is aclarubicin.

9. The method of claim 6, wherein the sH2A variant is an H2A.B variant.

10. The method of claim 9, wherein the H2A.B variant comprises a sequence as set forth in SEQ ID NO:3 and/or SEQ ID NO:4.

11. The method of claim 9, wherein the H2A.B variant is a protein encoded by histone H2A-Barr body-deficient type 1 (H2AFB1) (SEQ ID NO:25), H2A-Barr body-deficient type 2 (H2AFB2) (SEQ ID NO:26) and/or H2A-Barr body-deficient type 3 H2AFB3 (H2AFB3) (SEQ ID NO:27).

12. A method to inhibit cancer cell proliferation, the method comprising:
   (a) collecting a sample from a subject having or suspected of having lymphoma;
   (b) detecting a short histone H2A variant (sH2A) expression level in the sample collected from the subject;
   (c) administering to the subject a therapeutically effective dose of an anthracycline agent, if the subject has sH2A variant expression level that is detectable,
   wherein the anthracycline agent is selected from the group consisting of daunorubicin, doxorubicin, epirubicin, idarubicin, and aclarubicin.

13. The method of claim 12, wherein the lymphoma is selected from the group of diffuse large B-cell lymphomas (DLBCL), anaplastic large cell lymphoma (ALCL), and Hodgkin's lymphoma.

14. The method of claim 13, wherein the lymphoma is Hodgkin's lymphoma.

15. The method of claim 12, wherein the sH2A variant is an H2A.B variant.

16. The method of claim 12, wherein the anthracycline agent is aclarubicin.

17. The method of claim 15, wherein the H2A.B variant comprises a sequence as set forth in SEQ ID NO:3 and/or SEQ ID NO:4.

* * * * *